(12) United States Patent
Cattel et al.

(10) Patent No.: US 11,578,035 B2
(45) Date of Patent: *Feb. 14, 2023

(54) CHLORHEXIDINE CRYSTAL FORMS AND USES THEREOF IN MEDICINE

(71) Applicant: Queen Mary University of London, London (GB)

(72) Inventors: Michael Cattel, London (GB); Gleb Sukhorukov, London (GB); Saroash Shahid, London (GB); Dong Luo, London (GB)

(73) Assignee: Queen Mary University of London, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/832,248

(22) Filed: Mar. 27, 2020

(65) Prior Publication Data

US 2020/0290956 A1 Sep. 17, 2020

Related U.S. Application Data

(63) Continuation of application No. 16/085,489, filed as application No. PCT/GB2017/050752 on Mar. 17, 2017, now Pat. No. 10,640,463.

(30) Foreign Application Priority Data

Mar. 18, 2016 (GB) ...................... 1604639

(51) Int. Cl.
*C07C 279/26* (2006.01)
*A61P 31/04* (2006.01)

(52) U.S. Cl.
CPC .......... *C07C 279/265* (2013.01); *A61P 31/04* (2018.01); *C07B 2200/13* (2013.01)

(58) Field of Classification Search
None
See application file for complete search history.

(56) References Cited

U.S. PATENT DOCUMENTS

| | | | |
|---|---|---|---|
| 4,393,219 A | 7/1983 | Inoue et al. | |
| 4,496,322 A | 1/1985 | Sandham et al. | |
| 4,569,837 A | 2/1986 | Suzuki et al. | |
| 4,883,534 A | 11/1989 | Sandham et al. | |
| 2005/0244346 A1 | 11/2005 | Nakao et al. | |
| 2009/0233941 A1 | 9/2009 | Coleman et al. | |
| 2011/0033511 A1 | 2/2011 | Pisula et al. | |
| 2011/0146680 A1 | 6/2011 | Conway | |

FOREIGN PATENT DOCUMENTS

| | | |
|---|---|---|
| CN | 1090904 | 8/1994 |
| CN | 1231929 | 10/1999 |
| CN | 104856889 | 8/2015 |
| DE | 19848849 | 4/2000 |
| EP | 1532971 | 5/2005 |
| WO | 2014184582 | 11/2014 |

OTHER PUBLICATIONS

Cattaneo et al., "Crystal structure resolution of two different chlorhexidine salts", J Molecular Structure, 2016, 1121, pp. 70-73.
Loe and Harald, eds., Journal of Periodontal Research, 1986, Supplement 16, 21, pp. 5-89.
Luo et al., "Novel Formulation of Chlorhexidine Spheres and Sustained Release With Multilayered Encapsulation", ACS Applied Materials and Interfaces, 2016, 8, p. 12652-12660.
Luo et al., "Electrospun poly(lactic acid) fibers containing novel chlorhexidine particles with sustained antibacterial activity", Biomaterials Science, 2017, 5, pp. 111-119.
Musial, "The Deposition of Chlorhexidine on Chemically Modified Thermosensitive PolyNIPA Microgels Assessed By EDXS in Scanning Electron Microscopy", Lat Am J Pharm, 2011, 30(8), pp. 1481-1486.
Shutava et al., "Architectural layer-by-layer assembly of drug nanocapsules with PEGylated polyelectrolytes", Soft Matter, 2012, 8(36), pp. 9418-9427.

*Primary Examiner* — Sudhakar Katakam
*Assistant Examiner* — Jennifer C Sawyer
(74) *Attorney, Agent, or Firm* — Armstrong Teasdale LLP

(57) ABSTRACT

The present invention provides a crystalline salt of chlorhexidine chloride having a spherical morphology under Scanning Electron Microscopy (SEM) comprising a chloride anion and a cation selected from the group consisting of calcium, sodium, potassium, magnesium, zinc, strontium or iron, processes for the preparation of the salt, compositions, pharmaceutical compositions and uses thereof in medicine. Also provided are crystalline forms of the salt and fibres comprising the same.

23 Claims, 34 Drawing Sheets a b a b

C a b

CHLORHEXIDINE CRYSTAL FORMS AND USES THEREOF IN MEDICINE

FIELD OF THE INVENTION

The present invention relates to novel crystal forms of salts of chlorhexidine and uses thereof in medicine and to particles comprising such salts and uses thereof in medicine.

BACKGROUND OF THE INVENTION

Chlorhexidine (N,N'''1,6-Hexanediylbis[N'-(4-chlorophenyl)(imidodicarbonimidic diamide)] or (1E)-2-[6-[[amino-[(E)-[amino-(4-chloroanilino)methylidene]amino]methylidene]amino]hexyl]-1-[amino-(4-chloroanilino) methylidene]guanidine) is a bis-biguanide antiseptic and disinfectant that has bactericidal and bacteriostatic action against a wide range of gram-positive and gram-negative bacteria. Chlorhexidine has been used as a topical, antimicrobial tooth coating for the reduction of tooth decay in permanent teeth. U.S. Pat. No. 4,496,322 describes a dental varnish containing an antimicrobial agent, specifically chlorhexidine diacetate/acetate, a benzoin gum, and an orally-acceptable solvent that, when applied to teeth, dries to a film, that provides sustained release of the antimicrobial agent. An improvement on this technology was described in U.S. Pat. No. 4,883,534 that further provided a sealing composition, applied to the varnish, to extend the length of the antimicrobial protection provided by the varnish.

Chlorhexidine is also used in disinfectants (disinfection of the skin and hands), cosmetics (additive to creams, toothpaste, deodorants, and antiperspirants), and pharmaceutical products (preservative in eye drops, active substance in wound dressings and antiseptic mouthwashes). CN 1231929 has described chlorhexidine diacetate based compositions for use as a deodorizing agent in hosiery and socks. CN 1090904 described the incorporation of chlorhexidine in the preparation of hygiene supplies. US 2011/0146680 has described incorporating chlorhexidine gluconate into silicone catheters.

Benefits related to the addition of chlorhexidine in oral hygiene compositions have been widely reported in various studies. Loe and Harald, eds., In; Supplement No. 16, Vol. 21, 1986 to the Journal of Periodontal Research, presented articles entitled "Chlorhexidine in the Prevention and Treatment of Gingivitis." This Supplement is representative of numerous published reports concerning the inclusion of chlorhexidine in oral hygiene compositions such as dentifrices and rinses. Oral care formulations containing chlorhexidine have also been documented in various patents. For example, U.S. Pat. No. 4,569,837, entitled "Pharmaceutical Preparation for Remedy of Periodontal Disease and Process for Production Thereof," describes films for insertion in the gingival sulcus which contain and release chlorhexidine gluconate.

Efforts to treat periodontal/peri-implant disease have been impeded by several factors. Because the site of the bacterial infections is largely inaccessible to antimicrobial agents used in the oral cavity they are generally ineffective. Administration of antibiotics using controlled delivery devices has been shown to be a useful method of controlling the subgingival flora. However discontinuation of therapy is often associated with the return of the potential pathogens to the pockets. Long-term systemic and local antibacterial therapy has been used, but the potential dangers associated with this form of treatment, which include the development of resistant strains and super-imposed infections, do not warrant its serious consideration. Antibacterial agents such as chlorhexidine and quaternary ammonium salts in the form of mouth rinses have proved to be successful in preventing periodontal diseases. These agents, however, are unable to affect the subgingival flora when administered in this form as they do not penetrate into the pockets produced as a result of periodontitis and peri-implantitis. Hence, they cannot be used in mouth rinses to treat an established periodontal/peri-implant disease. By reacting the chlorhexidine base with acids, a large number of salts that are also sparingly water-soluble can be obtained.

It is important to note that the chlorhexidine products described to date have an immediate or burst release of the drug. There is therefore a need for sustained release formulations of chlorhexidine which enable a controlled delivery of the active substance where a longer term administration would be advantageous.

The present invention provides new crystal forms of salts of chlorhexidine as well as particles comprising such salts whereby the release mechanism can be switched between immediate release and controlled or sustained release. This is achievable by change in pH due to infection or by using external energy such as light, ultrasound or magnetic fields.

SUMMARY OF THE INVENTION

According to a first aspect of the invention, there is provided a crystalline salt of chlorhexidine chloride having a spherical morphology under Scanning Electron Microscopy (SEM) comprising a chloride anion and a cation selected from the group consisting of calcium, sodium, potassium, magnesium, zinc, strontium or iron.

Chlorhexidine is a cationic polybisguanide and the formal IUPAC name is N,N'''1,6-Hexanediylbis[N'-(4-chlorophenyl)(imidodicarbonimidic diamide)]. It is sometimes referred to as 1,6-bis(4-chloro-phenylbiguanido)hexan. Prior art uses as an antibacterial agent have used the dihydrochloride, diacetate and digluconate salt forms.

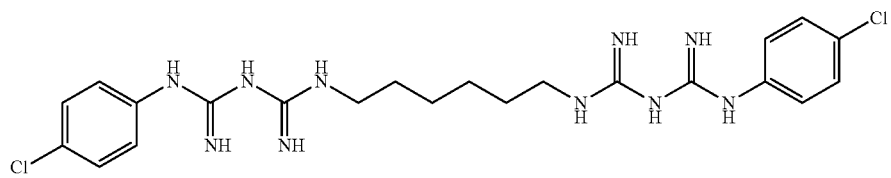 [SMILES: N=C(NCCCCCCNC(=N)NC(=N)Nc1ccc(Cl)cc1)NC(=N)Nc1ccc(Cl)cc1]

References to a cation selected from the group consisting of calcium, sodium, potassium, magnesium, zinc, strontium or iron include references to $Ca^{2+}$, $Na^+$, $K^+$, $Mg^{2+}$ $Zn^{2+}$, $Sr^{2+}$, $Fe^{3+}$ or $Fe^{2+}$.

Examples of a crystalline salt of chlorhexidine chloride of the invention having a spherical morphology under SEM are shown in FIG. 2, panels (a) to (d) and FIG. 7.

Crystals of the crystalline salt of chlorhexidine chloride of the invention having a spherical morphology under SEM are suitably monodisperse in form.

In one embodiment, the cation comprises calcium and the crystalline salt has an X-ray diffraction pattern comprising peaks, in terms of 2-theta, at about 8.5°, about 13.4°, about 15.9°, about 20.9°, about 23.7', and about 26.6°.

In one embodiment, the crystalline salt where the cation comprises calcium has X-ray diffraction pattern comprises peaks, in terms of 2-theta, at about 8.5°, about 12.7°, about 13.4°, about 15.9°, about 20.9°, about 23.7°, about 26.6', and about 34.4°.

In one embodiment, the crystalline salt where the cation comprises calcium has X-ray diffraction pattern comprises peaks, in terms of 2-theta, at about 8.5°, about 12.7°, about 13.4°, about 15.9°, about 20.9°, about 23.7°, about 26.6°, about 34.4° and about 35.5°.

In another embodiment, the crystalline salt where the cation comprises calcium has an X-ray diffraction (XRD) pattern as shown in FIG. 4, panels (e) and (f). The peaks may be as shown in Table 2 below.

Examples of a crystalline salt of chlorhexidine chloride of this embodiment of the invention having a spherical morphology under SEM are shown in FIG. 3, panels (c), (d), (e) and (f).

Suitably, the X-ray diffraction analysis may be performed on samples from values of 5 to 70° 2θ, suitably with a step size of 0.0334° and a count time of 200.03 s. Flat plate θ/θ geometry and Ni-filtered Cu—$K_a$ radiation ($K_{a1}$=0.15406 nm and $K_{a2}$=0.15444 nm) may be used. The XRD pattern for the chlorhexidine chloride of the invention may be compared to that for chlorhexidine diacetate.

The XRD indicates clear crystal structural differences in the crystalline salt of chlorhexidine chloride of the invention compared to chlorhexidine diacetate. The differences may be seen in the peak broadening in the XRD pattern, as well as smaller particle size for the crystalline salt of chlorhexidine chloride in comparison to chlorhexidine diacetate.

Crystalline chlorhexidine chloride of the invention may have a particle size distribution of a mean (SD) diameter of from about 15 to about 30 μm, suitably of from about 15 to about 25 μm, or from about 18 to about 22 μm.

Crystalline chlorhexidine chloride of the invention may suitably have a value of 8.5 wt % measured under thermogravimetric analysis when carried out at 10° C./min in a nitrogen atmosphere, over a temperature range of 50-800° C. Thermogravimetric analysis (TGA) is a method of thermal analysis in which changes in physical and chemical properties of materials are measured as a function of increasing temperature (with constant heating rate), or as a function of time (with constant temperature and/or constant mass loss).

The decomposition temperature of the crystalline chlorhexidine chloride of the invention may be about 210° C.

Fourier transform infrared (FTIR) spectra of crystalline chlorhexidine chloride of the invention may suitably show a band shift for C=N from 1610 $cm^{-1}$ to 1621 $cm^{-1}$. The FTIR spectra may also show peaks at 3118, 3303 and 3190 $cm^{-1}$ for the groups Alkyl-NH-Aryl, (Alkyl)$_2$NH and =NH. FTIR spectroscopy may be performed from 4000 to 600 $cm^{-1}$ at 2 $cm^{-1}$ resolution. The FTIR spectrum of the crystalline chlorhexidine chloride of the invention may suitably be compared to the spectrum of chlorhexidine diacetate.

Crystalline forms of chlorhexidine in accordance with the present invention provide controlled release or delayed (slow) release forms of chlorhexidine.

According to a second aspect of the invention, there is provided a process for the preparation of monodispersed crystals comprising chlorhexidine chloride salts of the invention, comprising
(i) mixing an aqueous solution of chlorhexidine diacetate with an aqueous solution of metal chloride of the formula (MCl$_x$), where x is equal to 1 or 2, at a concentration of 0.1M to 1.0M;
(ii) allowing the chlorhexidine chloride salt to precipitate;
(iii) centrifuging the precipitate formed in (ii) to obtain a solid mass of precipitated salt crystals; and
(iv) washing the precipitated solid mass of (iii).

The concentration of the metal chloride may be from 0.25M to 0.75M, suitably 0.33M. The concentration of the aqueous chlorhexidine acetate may be 5 mg/ml to 50 mg/ml, 10 mg/ml to 40 mg/ml, suitably 15 mg/ml. In one embodiment, the concentration of the metal chloride may be 0.33M and the concentration of the aqueous chlorhexidine acetate may be 15 mg/ml. Calcium chloride (CaCl$_2$) may be a suitable metal chloride salt for use in this process.

Crystalline chlorhexidine chloride prepared by this process may have a particle size distribution of a mean (SD) diameter of from about 15 to about 30 μm, suitably of from about 15 to about 25 μm, or from about 18 to about 22 μm.

The present invention therefore also provides a crystalline chlorhexidine chloride salt prepared by a process of the invention as defined above. In such a process, controlling crystallisation (nucleation and crystal growth) of the chlorhexidine chloride salts (particles) during the process can be achieved by the introduction of nuclei in the form of; emulsions, colloids, micro and nano-scale inorganic/metallic oxides, in order to change the size, number and morphology of the synthesized particles. This process allows controlled nucleation and therefore controlled chlorhexidine chloride particle size and volume fraction.

According to a third aspect of the invention, there is provided a cement composition comprising a crystalline chlorhexidine chloride salt of the invention and a phosphate cement, a polycarboxylate cement, a phenolate cement or a resin cement.

The cement is suitably a dental cement composition. The dental cement may be a resin cement or an acid-base cement (e.g. a glass ionomer cement (GIC)). A phosphate cement may comprise zinc phosphate ($Zn_3(PO_4)_2$). A polycarboxylate cement may comprise zinc polyacrylate (polycarboxylate). A phenolate cement may comprise zinc oxide-eugenol and 2-ethoxybenzoic acid (o-ethoxybenzoic acid (EBA)). A resin cement may comprise a polymer matrix composed of monomers of acrylate or methacrylate. Metal oxide or silicate fillers may be included as appropriate in a salt matrix. A glass ionomer cement (GIC) may be formed from silicate glass powder and polyalkenoic acid.

According to a fourth aspect of the invention, there is provided a pharmaceutical composition comprising a crystalline chlorhexidine chloride salt of the invention.

The pharmaceutical compositions of the invention may be administered in any effective, convenient manner effective for treating a patient's disease including, for instance, administration by oral, topical, intravenous, intramuscular, intranasal, or intradermal routes among others. In therapy or as a prophylactic, the active agent may be administered to an individual as an injectable composition, for example as a sterile aqueous dispersion, preferably isotonic.

For administration to mammals, and particularly humans, it is expected that the daily dosage of the active agent will be from 0.01 mg/kg up to 10 mg/kg body weight, typically around 1 mg/kg. The physician in any event will determine the actual dosage which will be most suitable for an individual which will be dependent on factors including the age, weight, sex and response of the individual. The above dosages are exemplary of the average case. There can, of course, be instances where higher or lower dosages are merited, and such are within the scope of this invention.

The pharmaceutical compositions of the invention may be employed in combination with pharmaceutically acceptable carrier or carriers. Such carriers may include, but are not limited to, saline, buffered saline, dextrose, liposomes, water, glycerol, ethanol and combinations thereof.

According to a fifth aspect of the invention, there is provided crystalline chlorhexidine chloride salts according of the invention as defined above for use in medicine. Medical uses in accordance with the present invention extend to and include use in a method of treatment of a disease or medical condition as defined herein. Such methods of treatment comprise the step of administering a composition of the invention to a subject in need thereof. The invention also includes uses in the manufacture of a medicament for use in the treatment of such diseases or conditions.

According to an sixth aspect of the invention, there is provided a metal or metal oxide particle of mean average particle diameter size 10 to 50 nm comprising crystalline chlorhexidine chloride salts of the invention as defined above.

According to a seventh aspect of the invention, there is provided a composition comprising crystalline chlorhexidine chloride salts of the invention as defined above encapsulated or dispersed in a polyelectrolyte, or a polymerizable methacrylate monomer, for example a methacrylate monomer. The polymerizable methacrylate monomer may be hydroxyethyl methacrylate (HEMA)-urethane dimethacrylate (HEMA-UDMA), or polymethylmethacrylate (PMMA). The polymer may also comprise a photoinitiator. Such polymers may be cured through the action of visible or UV light, or heat or allowed to cure without further input ("self-cure").

References herein and throughout the specification to polymerization therefore include self-polymerization, light polymerization and dual or dual cure polymerization.

According to an eighth aspect of the invention, there is provided a composition comprising a metal or metal oxide particle of the invention as defined above encapsulated in a polyelectrolyte, and/or a polymerizable monomer. In some embodiments, the metal or metal oxide particles are magnetic, i.e. capable of being influenced by a magnetic field, including substances that are ferromagnetic (e.g. iron, nickel, cobalt and alloys as well as rare earth elements). The particle may be encapsulated in multiple layers of the polyelectrolyte and/or polymer containing a crystalline chlorhexidine chloride salt of the invention.

The advantages of the aspects of the invention where polymers or metal/metal oxide particles are present is that it allows a burst release of the drug compound when using a dental light curing unit and movement of the particles using a magnetic field, via a tailored magnetic instrument. Magnetic movement of the particles allows the drug to be moved to the site of infection, allowing functionalized chlorhexidine compounds through the resin to create a graduated structure and to control chlorhexidine release at the surface. These compounds can be utilised in the clinical layering of dental or manufactured composites/polymers in order to ensure burst or slow release tailored to certain clinical conditions and treatments and removable/fixed prosthesis.

Consequently, it is also envisaged that such metal/metal oxide particles comprising crystalline chlorhexidine chloride salts of the invention as defined above may be formulated in a polymer as defined herein also. The polymer coated particle may comprise multiple layers of polymer and/or polyelectrolyte containing a crystalline chlorhexidine chloride salt of the invention.

According to a ninth aspect of the invention, there is provided a composition comprising polylactic acid (PLA) and crystalline chlorhexidine chloride salts of the invention as defined above.

According to a tenth aspect of the invention, there is provided a composition comprising a bioactive glass composed of at least two or more selected from the group consisting of: $SiO_2$, $CaO$, $CaF_2$, $SrF_2$, $SrO$, $Na_2O$, $MgO$, $ZnO$, $K_2O$, $B_2O_3$, $PO_3$, $P_2O_5$, $NaF$, $CaCl_2$ and $NaCl$ and a crystalline form of a chlorhexidine chloride salt of the invention as defined above.

The composition may further comprise silica, for example pyrogenic silica, e.g. from 1-90%. Pyrogenic silica is produced by burning silica in a flame and consists of microscopic droplets of amorphous silica fused into branched, chainlike, three-dimensional secondary particles which then agglomerate into tertiary particles. The pyrogenic (pyrolytic) silica may silanised or non-silanised. Bioactive glasses are surface reactive biomaterials. Alternatively, the silica may be quartz.

Examples of bioactive glasses are:
- 47.32 mol % $SiO_2$, 7.01 mol % $CaO$, 5.52 mol % $CaF_2$, 5.52 mol % $SrF_2$, 3.4 mol % $SrO$, 31.23 mol % $MgO$.
- 47.32 mol % $SiO_2$, 7.01 mol % $CaO$, 5.52 mol % $CaF_2$, 5.52 mol % $SrF_2$, 3.4 mol % $SrO$, 30.23 mol % $MgO$, 1.0 mol % $ZnO$.
- 47.32 mol % $SiO_2$, 5.91 mol % $CaO$, 5.52 mol % $CaF_2$, 5.52 mol % $SrF_2$, 4.5 mol % $SrO$, 29.23 mol % $MgO$, 2.0 mol % $ZnO$.
- 47.32 mol % $SiO_2$, 5.2 mol % $CaO$, 5.52 mol % $CaF_2$, 5.52 mol % $SrF_2$, 5.21 mol % $SrO$, 28.23 mol % $MgO$, 3.0 mol % $ZnO$.

Other possible bioactive glass compositions also include:
- 46.1 mol % $SiO_2$, 26.9 mol % $CaO$, 24.4 mol % $Na_2O$ and 2.5 mol % $P_2O_5$.
- 60 mol % $SiO_2$, 36 mol % $CaO$ and 4 mol % $P_2O_5$.
- 70 mol % $SiO_2$, 30 mol % $CaO$.
- 53 mol % $SiO_2$, 23 mol % $Na_2O$, 20 mol % $CaO$ and 4 mol % $P_2O_5$.

The composition with respect to this aspect of the invention may further comprise a metal or a metal oxide particle, a polyelectrolyte, PLA or a polymerizable monomer. The composition may comprise multiple layers of polymer and/or polyelectrolyte containing a crystalline chlorhexidine chloride salt of the invention.

Particle size for the fillers may be in the range of from 1-5 µm (microns) ($D_{50}$). The bioactive glasses may be ground to a particle size of 3-10 µm (microns). The bioactive glasses may be mixed into a suitable polymer as described herein in the ratio of 3:2.

According to an eleventh aspect of the invention, there is provided a metal or metal oxide particle of the invention as defined above or a composition of the invention as defined above for use in medicine. Medical uses in accordance with the present invention extend to and include use in a method of treatment of a disease or medical condition as defined herein. Such methods of treatment comprise the step of administering said compositions to a subject in need thereof.

The invention also includes uses in the manufacture of a medicament for use in the treatment of such diseases or conditions.

The metal or metal oxide particle may be magnetic. Thus the invention provides for a process of moving functionalised chlorhexidine particles and fillers/glasses and bioactive glasses through a polymeric material under the control of a magnet, so that a magnetic field can be utilised to create graduated microstructures to influence wear, strength and antimicrobial activity. This may be advantageous in a clinical setting.

Methods of treatment in accordance with this aspect of the invention, therefore comprise the steps of: administering a polymeric material comprising a salt or composition of the invention (for example chlorhexidine particles and fillers/glasses and bioactive glasses as defined herein) to a subject, and subsequently applying a magnetic field to the polymeric material in situ in the subject. The application of the magnetic field causes the chlorhexidine particles to move so as to construct a graduated microstructure within the polymeric material.

In one embodiment of the invention, the method of treatment may comprise the steps of: administering a polymeric material comprising a salt or composition of the invention which further comprises a photoinitiator to a subject, and subsequently applying visible or UV light to the polymeric material in situ in the subject. The application of the visible or UV light causes the polymeric material comprising the salt or composition to be cured and thereby hardened.

According to a twelfth aspect of the invention, there is provided a natural or synthetic fibre further comprising crystalline chlorhexidine chloride salt of the invention as defined above. The natural or synthetic fibre may be selected from the group consisting of cellulose, cotton, polyurethane and nylon. These fibres can be used to produce wound dressings, socks, clothes, gloves, catheters, contact lenses, blood bags, packaging and polymer films for wider biomedical and commercial applications. The fibre may comprise multiple layers of polymer and/or polyelectrolyte containing a crystalline chlorhexidine chloride salt of the invention.

The present invention provides compositions for use in medicine as described above as well as pharmaceutical compositions as defined above. However, compositions comprising crystalline chlorhexidine salt of any aspect of the invention as defined may also be used for non-medical uses, i.e. cosmetic uses.

The present invention relates to a novel method for producing chlorhexidine compounds of controlled morphology and composition, which exhibit different chlorhexidine release. These compounds can be synthesized from various salts combined with chlorhexidine diacetate to form needles, flakes or spherical chlorhexidine compounds. These powder compounds can be incorporated in various polymeric delivery devices or materials for the controlled released of chlorhexidine and other ions for dental, medical or other uses. The new chlorhexidine compounds can also be functionalised using gold, silver or iron nano-particles and encapsulated or introduced into electrospun PLA fibres.

It is then possible to activate these compounds and affect a burst chlorhexidine release using ultrasonic, light curing or magnetic fields. The said compounds can be incorporated into polymerizable dental/medical polymers which can then be coated onto human bone or exposed dental implant surfaces. They can also be used; as a tooth/root canal filling material, to fabricate denture bases or polymerized using various methods to produce a solid polymer system. The polymerized polymer will provide a matrix for the controlled release of chlorhexidine from the compounds.

Furthermore, powdered compounds produced can be incorporated in other natural and synthetic fibres such as cellulose, cotton, polyurethane and nylon to produce wound dressings, socks, catheters, contact lenses, blood bags, packaging and polymer films for wider biomedical, veterinary and commercial applications. The fibres may be electrospun into the form of a mat, web, or other substrate suitable for use.

There is also the opportunity to incorporate powdered compounds into surgical gloves, profi (prophy or prophylaxis) pastes, mouthwashes, toothpastes and light activated fissure sealants and gels for dental applications.

The compounds described herein can be incorporated into polymerizable dental/medical polymers which can then be applied onto human bone or exposed dental implant surfaces. They can also be used as a tooth/root canal filling material, to fabricate denture bases or polymerized using various methods to produce a solid polymer system.

Encapsulation of these novel chlorhexidine crystals with polyelectrolyte multilayers overcomes the current drug delivery problems encountered in dentistry. Layer by layer (LbL) encapsulation alters the morphology of drug colloids, and prolongs the chlorhexidine release kinetics. The combination of chlorhexidine co-precipitation and LbL techniques has created new chlorhexidine formulations, morphology and encapsulation. Further modification to the chlorhexidine polymorph structure is possible to achieve both sustained and stimuli responsive release, which will enhance its clinical performance for uses in medicine and dentistry.

Preferred features for the second and subsequent aspects of the invention are as for the first aspect mutandis mutandis.

The invention will now be described by way of reference only with reference to the following Examples which are present for the purposes of reference only.

BRIEF DESCRIPTION OF THE FIGURES

In the Examples the following figures are present in which:

FIG. 3, panel (g): shows SEM image showing the morphology of chlorhexidine diacetate. FIG. 3, panel (h): shows size distribution of chlorhexidine chloride compounds formed with 0.5, 0.33, 0.25, and 0.125 M $CaCl_2$) solutions.

FIG. 4, panel (b) shows calibration curve of chlorhexidine absorption peak versus concentration. FIG. 4, panel (c) shows FTIR spectra of chlorhexidine diacetate and the spherical chlorhexidine chloride compound. FIG. 4, panels (d)-(f) show the XRD spectrum and peak fitting of plots generated by Panalytical's X'Pert HighScore software for panel (d) Chlorhexidine Diacetate (X8657) and panel (e) Spherical chlorhexidine chloride compound (X8968), panel (f) Overlapped XRD patterns for FIG. 4, panels (d) and (e).

FIG. 10, panels (b) and (c) show SEM results of spherical chlorhexidine chloride compounds functionalised with iron oxide and respective particle size diameter distribution FIG. 10, panel (b)).

FIG. 11, panel (b) shows SEM photomicrograph of spherical chlorhexidine chloride compound after surface layer by layer assembly of PAH and PSS. FIG. 11, panel (c) shows release curve of chlorhexidine from encapsulated and uncoated spherical chlorhexidine chloride particles (CHXP) in $H_2O$. FIG. 11, panel (d) shows release curve of chlorhexidine from encapsulated chlorhexidine chloride particles in phosphate buffered saline.

FIG. 12, panel (b) shows confocal image of rhodamine B (TRITC, Sigma) labelled encapsulated spherical chlorhexidine chloride compound in the HEMA-UDMA polymer.

FIG. 14, panel (b) shows chlorhexidine release curve of chlorhexidine compounds with different morphology.

FIG. 17, panel (b) shows SEM photomicrograph of electrospun PLA fibres containing spherical chlorhexidine chloride compounds after water storage (37° C.). FIG. 17, panel (c) shows the chlorhexidine release curve of chlorhexidine chloride compounds from the PLA fibre at different temperatures.

Figure 34:
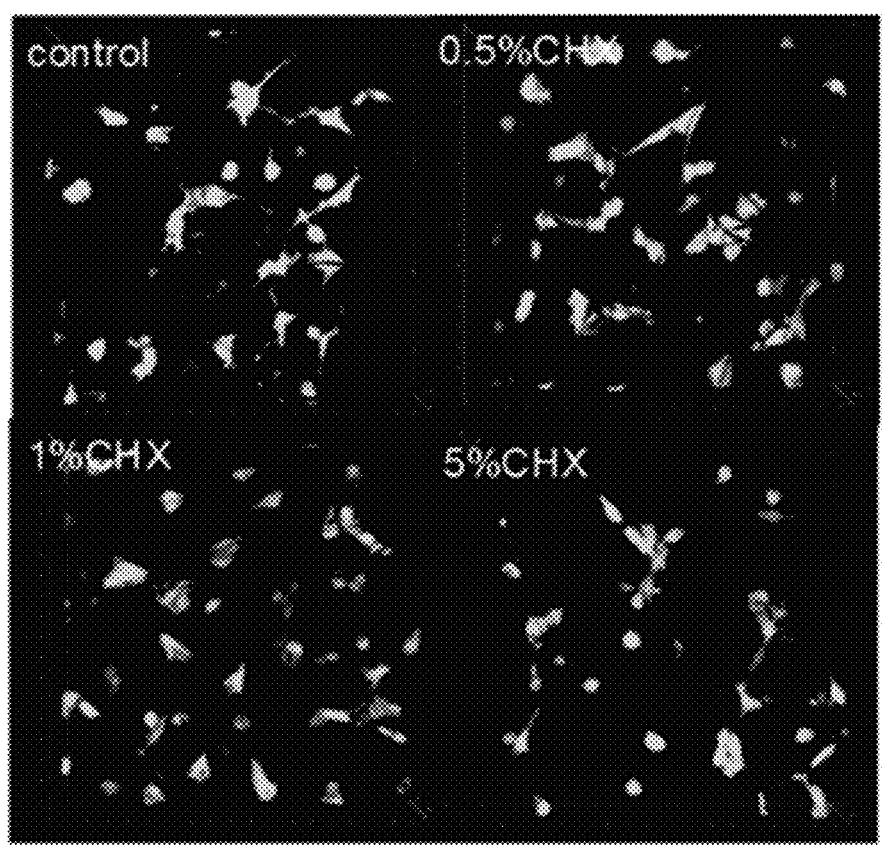

FIG. 34 shows 3D images of fibroblast adhesion on PLA fibres containing uncoated chlorhexidine particles with chlorhexidine loading ratio at 0.5, 1 and 5% (wt/wt).

Figure 35:
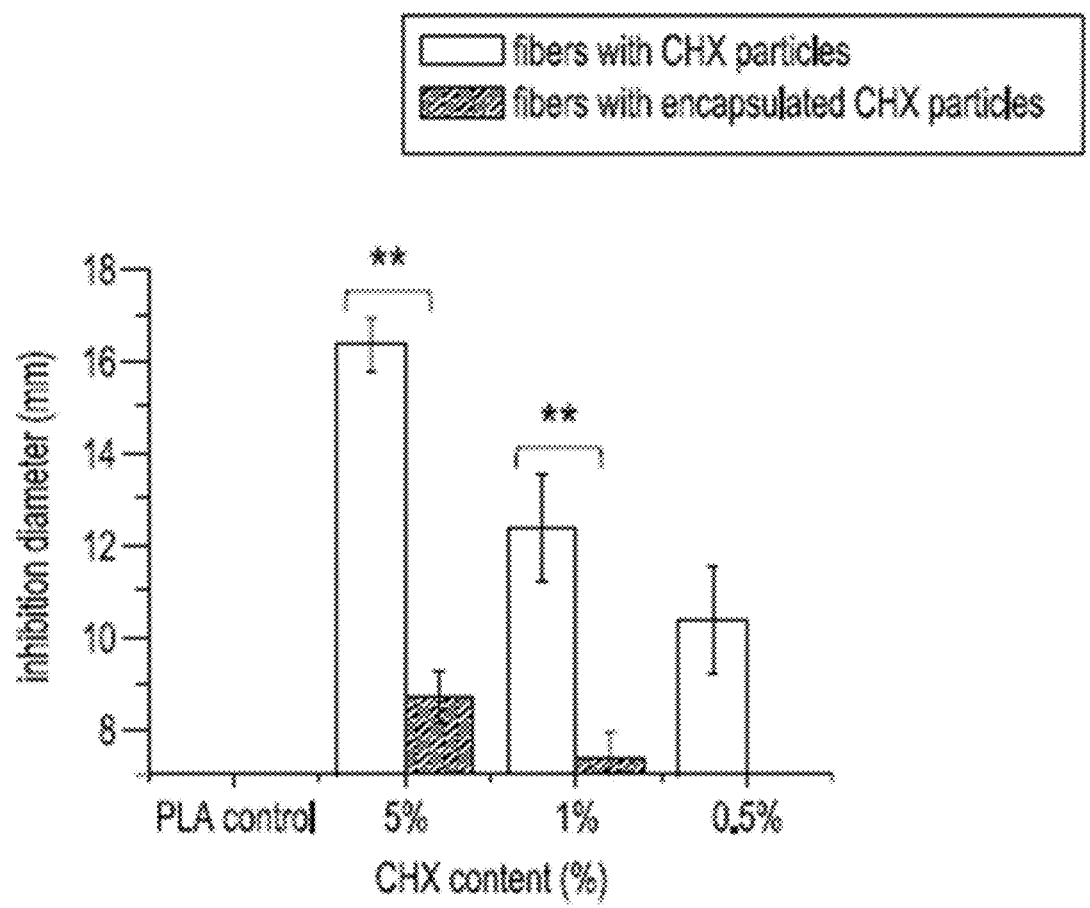

FIG. 35 shows in vitro inhibition of chlorhexidine containing fibres against *E. coli* using an agar diffusion assay. PLA fibres containing uncoated chlorhexidine particles (white) and encapsulated chlorhexidine particles (grey), and fibres without chlorhexidine were used as a control, **p<0.01 indicates statistical differences between the two types of fibres (n=3).

DETAILED DESCRIPTION OF THE INVENTION

Example 1

Chlorhexidine diacetate (Sigma-Aldrich, C-6143, Lot: 19H0417) solution with a concentration of 15 mg/ml was used. The salt solutions of $Na_2CO_3$ (Sigma, 22353-0, Lot: 090M0112V), $NaHCO_3$ (BDH, 251, Lot: K18257716), $Na_2HPO_4$ (Sigma, S5136, Lot: 077K01281), $Na_2SO_4$ (Sigma, 23859-7, Lot: 09619JH278), NaBr (Sigma, 71329, Lot: BCBH7389V) and KI (Sigma, 60400, Lot: BCBB9119) were prepared with the anion concentration fixed at the range from 0.2 M to 2M. The chlorhexidine diacetate solution was mixed using a pipette (Eppendorf, Germany) with these salt solutions at a ratio of 1:1 by volume. The mixture was shaken for 1 min, and then centrifuged to a turbid mixture at 2000 rpm for 1 min (Eppendorf centrifuge 5417C, Germany). The sediment was washed with deionized water (three stage Millipore Milli-Q 185 water purification system, Millipore, USA) three times. For storage, the formed product was freeze dried (ScanVac Cool Safe Freeze Drying, Denmark) at −107° C., 0.009 mBar for 1 day.

Figure 1:
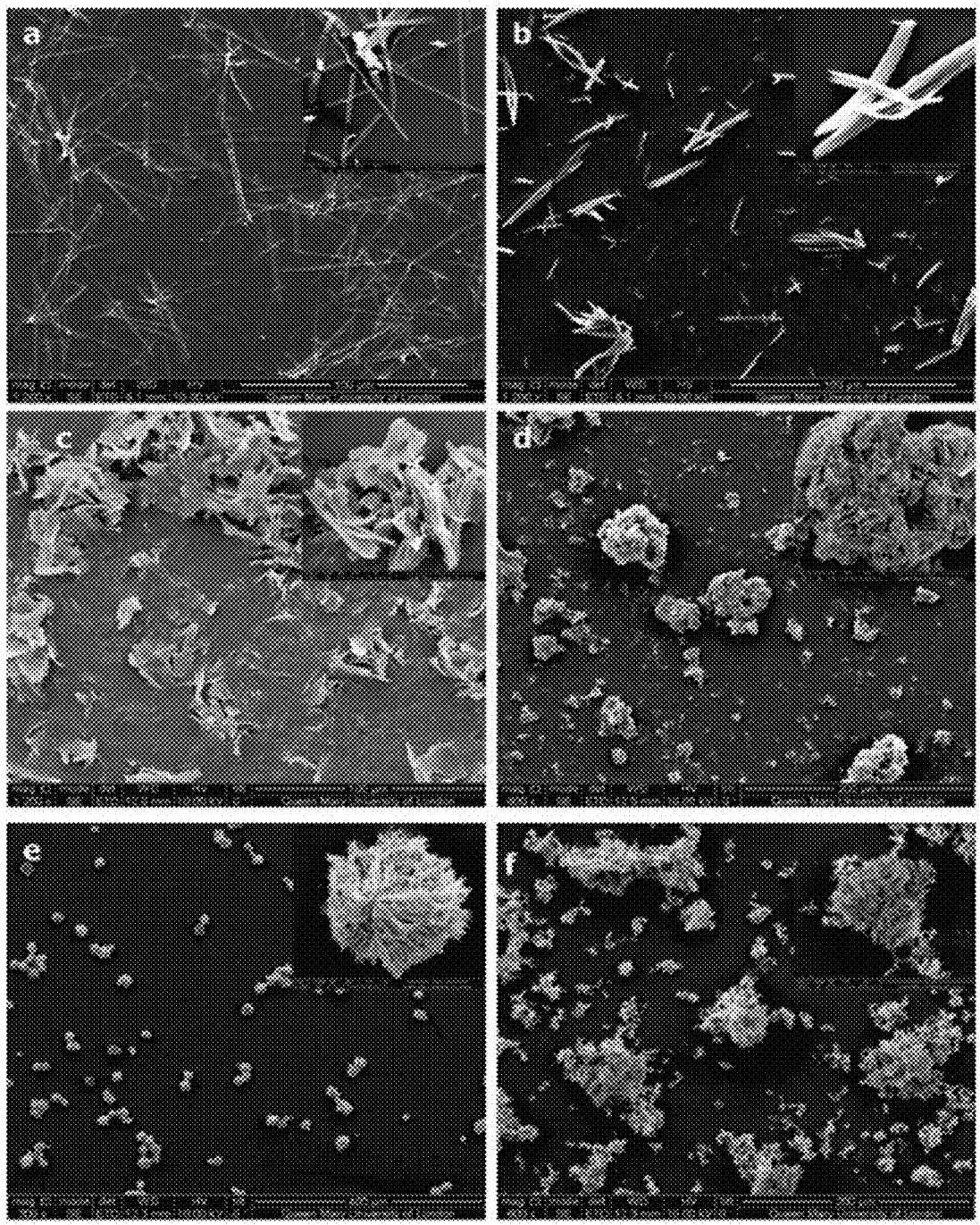
FIG. 1, panels (a)-(f) show SEM images of chlorhexidine compounds panel (a): $Na_2CO_3$, panel (b): $Na_2HPO_4$, panel (c): $NaHCO_3$, panel (d): $Na_2SO_4$, panel (e): NaBr, panel (f): KI).

The morphology of these sediments was characterised using scanning electron microscopy (FEI inspect-F, USA) at an accelerating voltage of 10 kv (spot size of 3.5 and working distance of 10 mm) and results are shown in FIG. 1, panels (a)-(f). Chlorhexidine diacetate formed irregular fibres when mixed with 0.33M $Na_2CO_3$ FIG. 1, panel (a)) and 0.66 M $NaHCO_3$ FIG. 1, panel (b)), the length of which was from 10 μm to 60 μm. Flake clusters were formed with 0.66M $Na_2HPO_4$ FIG. 1, panel (c)) and 0.33 M $Na_2SO_4$ FIG. 1, panel (d)) when mixed with chlorhexidine diacetate. However the halogenous salts formed more fibrous structures with chlorhexidine diacetate. With 0.66 M NaBr solution mixed with Chlorhexidine diacetate, individual particles were formed FIG. 1, panel (e)), which were approximately 10 to 20 μm sized fibrous spheres, and there were signs of agglomeration. 0.66 M KI mixed with chlorhexidine diacetate led to a more fibrous structure FIG. 1, panel (f)).

Example 2(a)

Chlorhexidine diacetate concentration was fixed at 15 mg/ml and $CaCl_2$ (Sigma-Aldrich, C8106, Lot: SLBF7416V) concentrations from 2M, 1M, 0.5M, 0.33M, 0.25M to 0.125M, were mixed using a pipette at the volume ratio of 1:1.

Other chloride salts, 0.66M NaCl (Sigma, S7653, Lot: BCBH3643V), 0.66M KCl (Sigma, P5406, Lot: 066K0054), 0.33 M $MgCl_2$ (Sigma, M8266, Lot: 081M0003V) and 0.33M $ZnCl_2$ (Sigma, 96468, Lot: BCBG2194V) were also mixed using a pipette with chlorhexidine diacetate (15 mg/ml) at a volume ratio of 1:1. The mixtures were shaken for 1 min and centrifuged at 2000 rpm for 1 min (Eppendorf centrifuge 5417C, Germany). All mixtures were washed with deionized water (three stage Millipore Milli-Q 185, Millipore, USA) three times. The $CaCl_2$/Chlorhexidine diacetate mixture can alternatively be washed three times in 0.33 M $CaCl_2$ solution, to reduce the dissolution of the particles.

Figure 3:
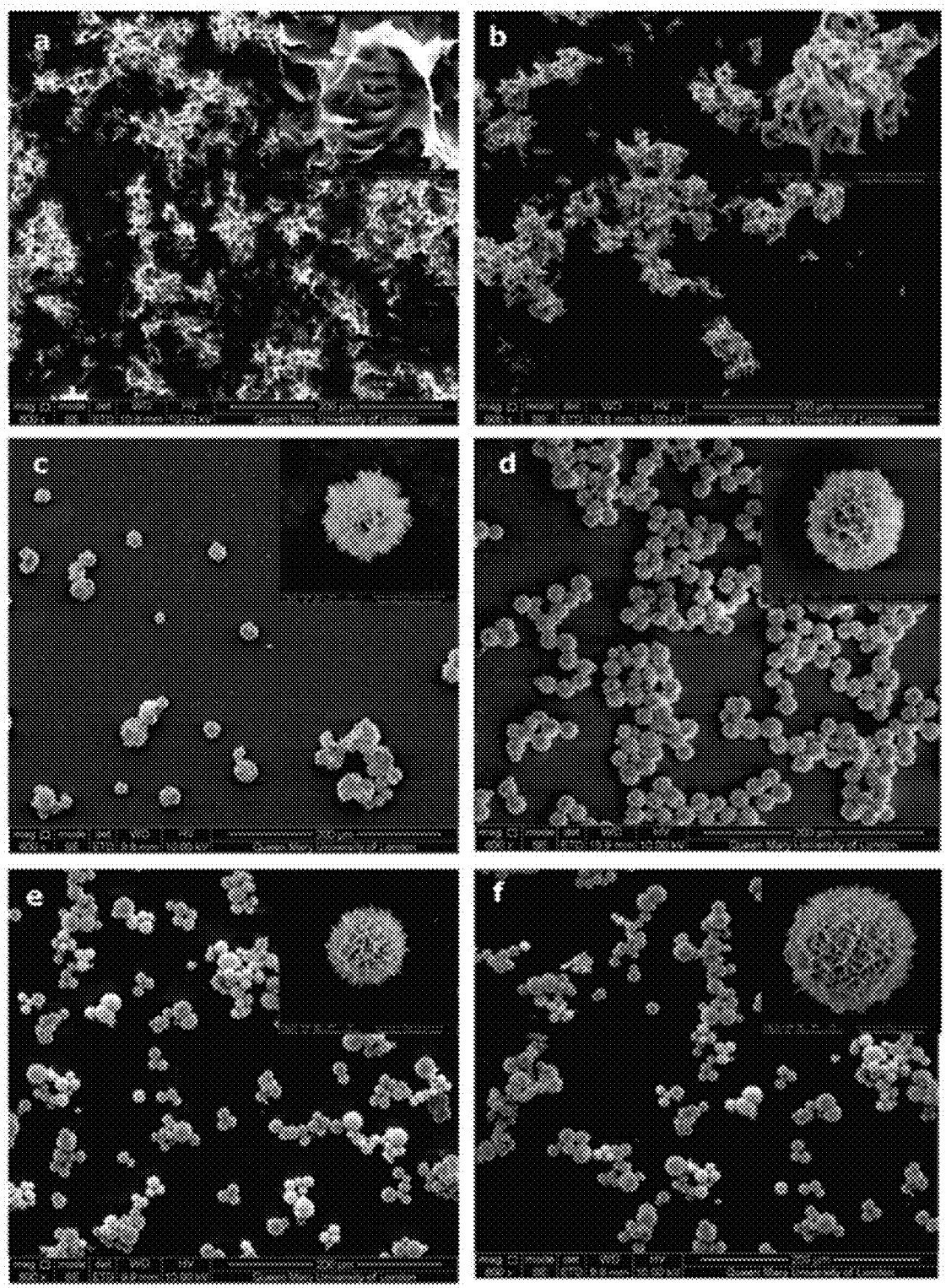
FIG. 3, panels (a)-(f) show chlorhexidine compounds forming from different concentrations of ($CaCl_2$) solutions; panel (a) 2 M, panel (b) 1 M, panel (c) 0.5 M, panel (d) 0.33 M, panel (e) 0.25, panel (f) 0.125 M $CaCl_2$) solutions.
Figure 3:
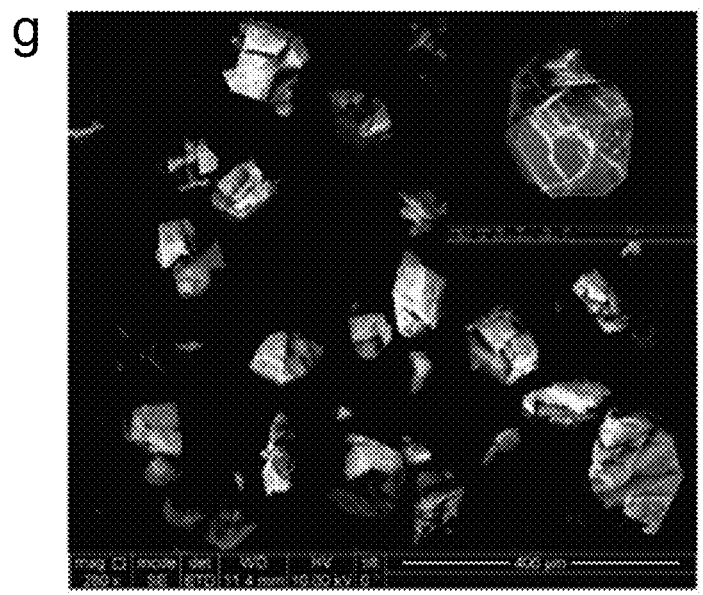
Figure 3:
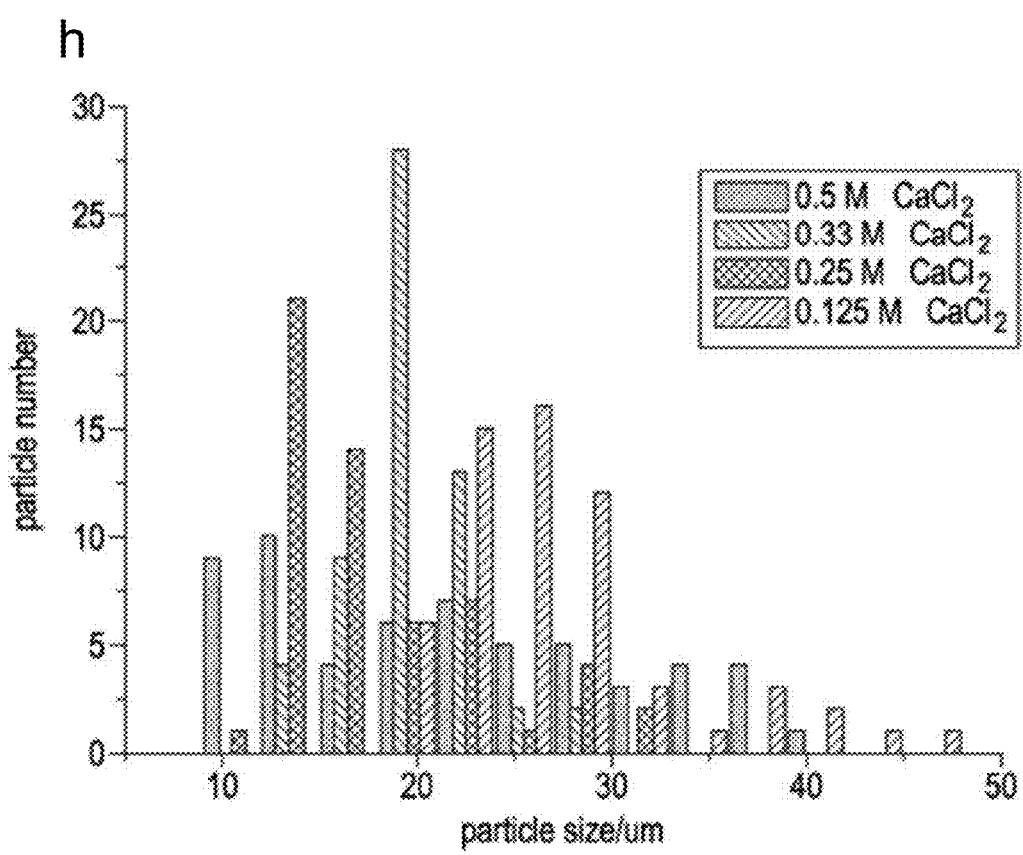

Chlorhexidine chloride compound formation with spherical morphology was a concentration dependent process (as shown in FIG. 3, panels (a)-(f)). $CaCl_2$) solution with a concentration of 2 M resulted in irregular sediments (FIG. 3, panel (a)). When the concentration was reduced to 1 M a similar structure was present (FIG. 3, panel (b)). The 0.5 M $CaCl_2$) solution led to precipitation of individual particles, most of which were spherical/semi spherical with a high porosity (FIG. 3, panel (c)). When the $CaCl_2$ solution was 0.33 M more regular spheres were produced (FIG. 3, panel (d)). Reducing the $CaCl_2$) concentration to 0.25 M and 0.125 M resulted in the synthesis of particle morphology with a more spherical and compact structure (FIG. 3, panels (e)-(f)). The size distribution of the chlorhexidine compounds formed with different $CaCl_2$ concentrations is shown in FIG. 3, panel (h) and Table 1. Particles formed with 0.125M $CaCl_2$) had a wide size distribution and larger Mean particle size (26.8 μm). The 0.33 M group had the narrowest size distribution (Table 1), with a Mean (SD) diameter of 19.9 (3.1) μm. The chlorhexidine compound from this group was used in all the following encapsulation and chlorhexidine release studies (Examples 4 and 5-9).

Figure 2:
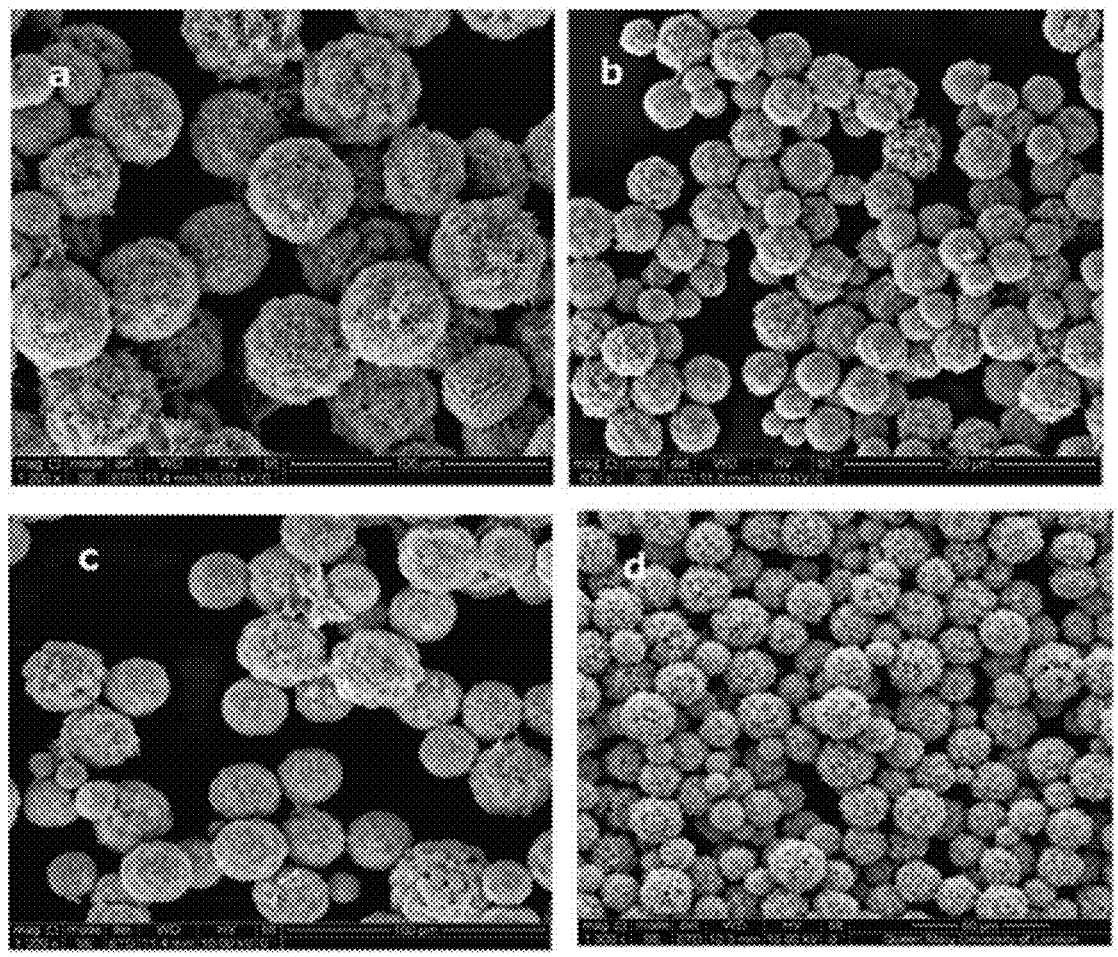
FIG. 2, panels (a)-(d) show chlorhexidine compounds formed with; panel (a) NaCl, panel (b) KCl, panel (c) $MgCl_2$ and panel (d) $ZnCl_2$.

The original morphology of chlorhexidine diacetate is also shown in FIG. 3, panel (g) as a comparison with the new chlorhexidine chloride compounds. The other chloride salts (NaCl, KCl, $ZnCl_2$, and $MgCl_2$) mixed with chlorhexidine diacetate also led to the formation of spherical compounds (FIG. 2, panels (a)-(d)).

The crystallisation (nucleation and crystal growth) of the chlorhexidine chloride compounds (particles) can be controlled by the introduction of nuclei in the form of; emulsions, colloids, micro and nano-scale inorganic/metallic oxides, in order to change the size, number and morphology of the synthesized particles. This allows a wide range of crystallite sizes from 30 μm to <50 nm, and control of the volume fraction.

The content of chlorhexidine in the compound, made from 0.33M $CaCl_2$ and 15 mg/ml chlorhexidine diacetate, was determined by UV-Vis absorption (Lambda 35, Perkin Elmer, USA). Initially, a series of chlorhexidine diacetate solutions with standard concentrations of 0.25, 0.5, 1, 2, 3, 4, 5, 10, 20, 40 ppm were prepared, and the absorption was measured FIG. 4, panel (a)). The absorption peak at 254 nm and the reference concentration had a linear relationship, and the standard curve of absorption verses concentration was established (FIG. 4, panel (b)). The chlorohexidine proportion in the spheres (0.33M $CaCl_2$ group) was calculated to be 90%-99.9% when they were co-precipitated from 15 mg/ml chlorhexidine diacetate solution.

Figure 19:
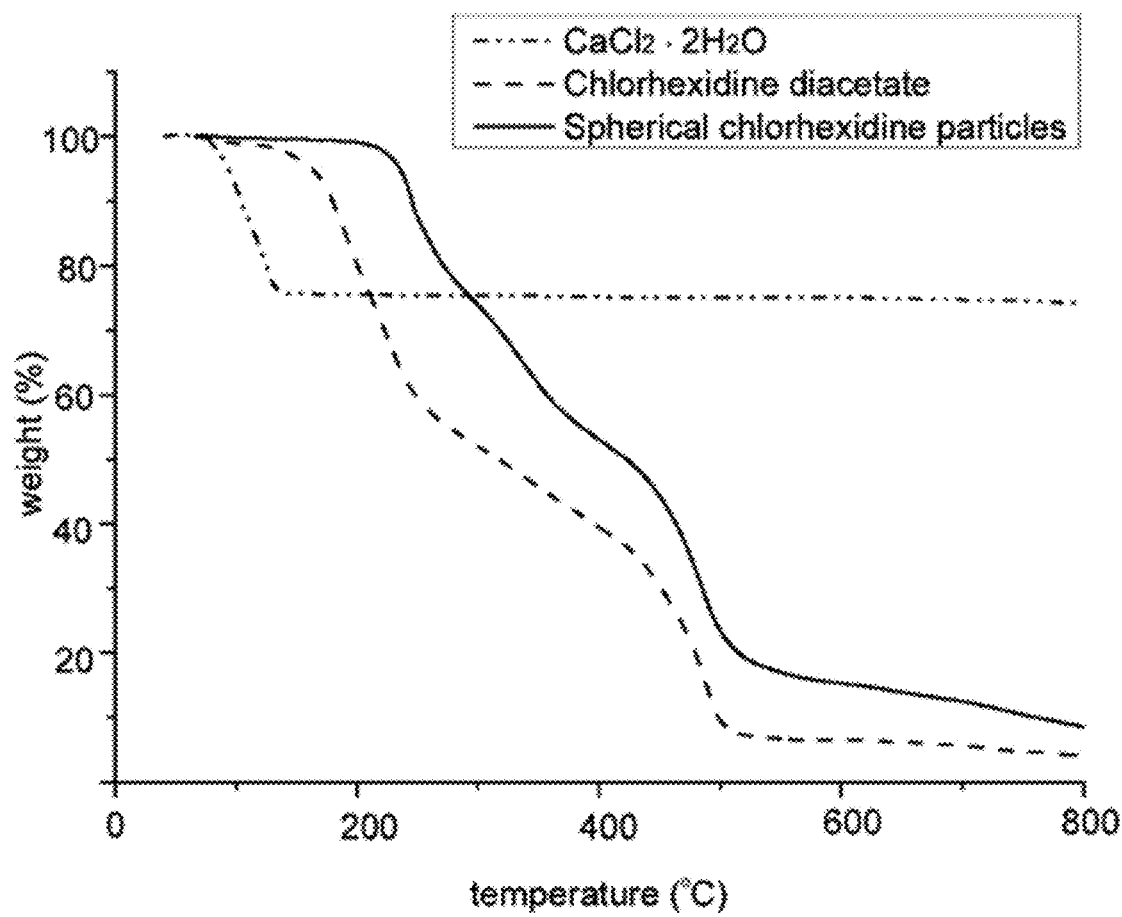
FIG. 19 shows the TGA results for the spherical chlorhexidine chloride compound, chlorhexidine diacetate and $CaCl_2$ powders.

The chlorhexidine chloride spheres (0.33M $CaCl_2$ group) were analysed by Thermo-gravimetric analysis (TGA Q50, USA). Chlorhexidine diacetate crystals and $CaCl_2$ powder (Sigma-Aldrich, C8106, Lot: SLBF7416V) were tested as comparisons. TGA was carried out at 10° C./min in a nitrogen atmosphere, over a temperature range of 50-800° C. The chlorhexidine proportion was further confirmed by the TGA result. As shown in FIG. 19, the $CaCl_2$ powder had 74 wt % at 800° C., chlorhexidine diacetate had only 4 wt % at 800° C. and the spherical chlorhexidine chloride particles (Example 2(a)) had 8.5 wt %. The decomposition temperature of the chlorhexidine chloride spheres (210° C.) was higher than the chlorhexidine diacetate crystals (120° C.).

FTIR spectra of spherical chlorhexidine chloride compounds and chlorhexidine diacetate were performed from 4000 to 600 cm$^{-1}$ at 2 cm$^{-1}$ resolution (Bruker Tensor 27, UK), and compared to the spectrum of chlorhexidine diacetate which was used for particle synthesis. The typical band of C=N for chlorhexidine was shifted from 1610 cm$^{-1}$ to 1621 cm$^{-1}$. A distinct intensity increase at 3118, 3303 and 3190 cm$^{-1}$, were assigned to stretching vibration N-H of the groups Alkyl-NH-Aryl and (Alkyl)$_2$NH and the group =NH (FIG. 4, panel (c)). The band shift and intensity change was due to the electron density change for=NH group, which further predicated that the biguanides of chlorhexidine may have coordinated with Ca$^{2+}$.

Structural analysis was carried out using X-ray diffraction (XRD) using an X'Pert Pro X-ray diffractometer (Panalytical, Almelo, The Netherlands). The spherical chlorhexidine chloride compounds from Example 2 (FIG. 3, panel (d)), and the chlorhexidine diacetate powder (FIG. 3, panel (g)) were analysed. Specimens were run from 5 to 70° 2θ with a step size of 0.0334° and a count time of 200.03 s. Flat plate θ/θ geometry and Ni-filtered Cu-Ka radiation (K$_{a1}$=0.15406 nm and K$_{a2}$=0.15444 nm) were used.

Figure 4:
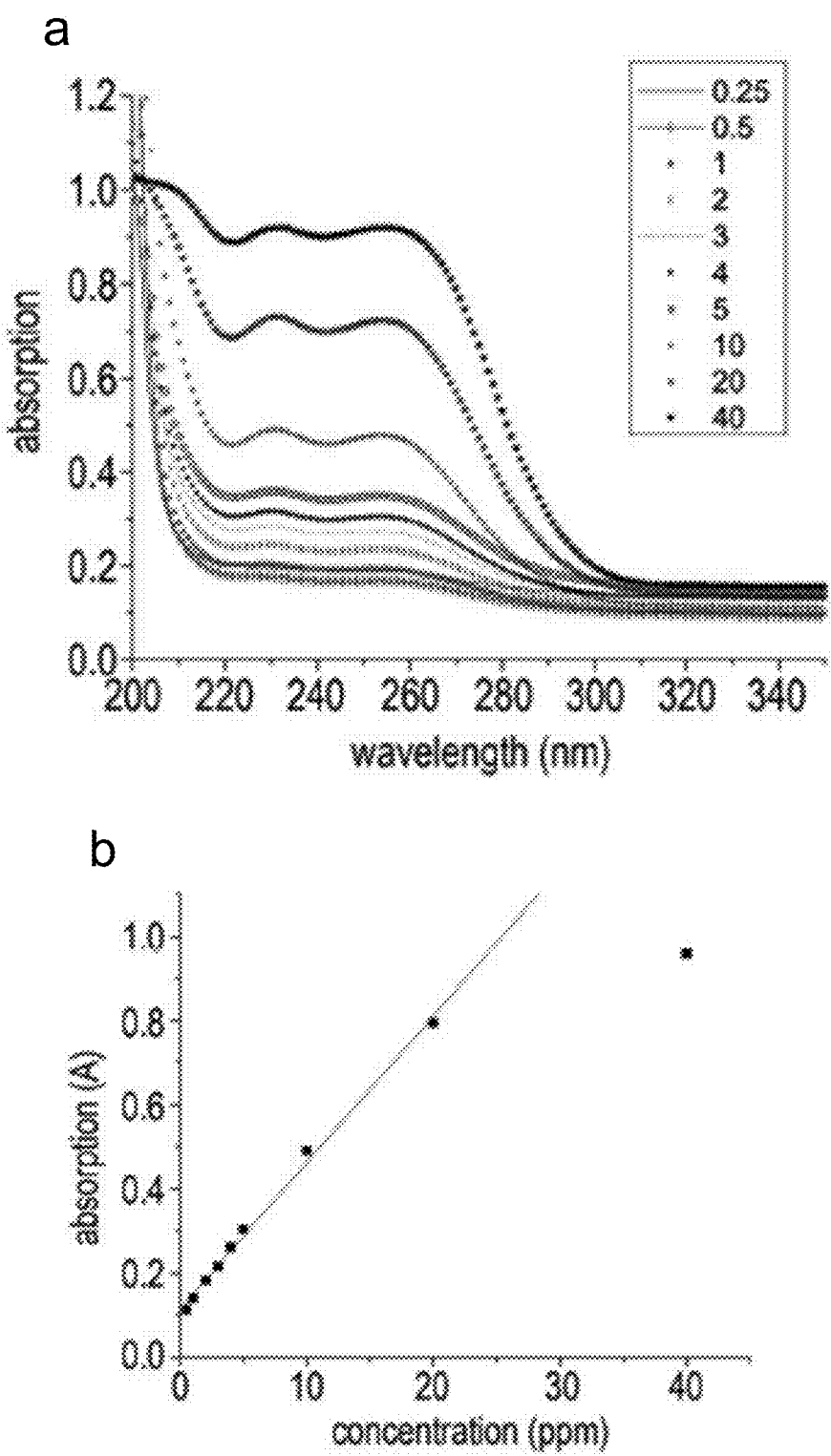
FIG. 4, panel (a) shows absorption of chlorhexidine solutions with various concentrations.
Figure 4:
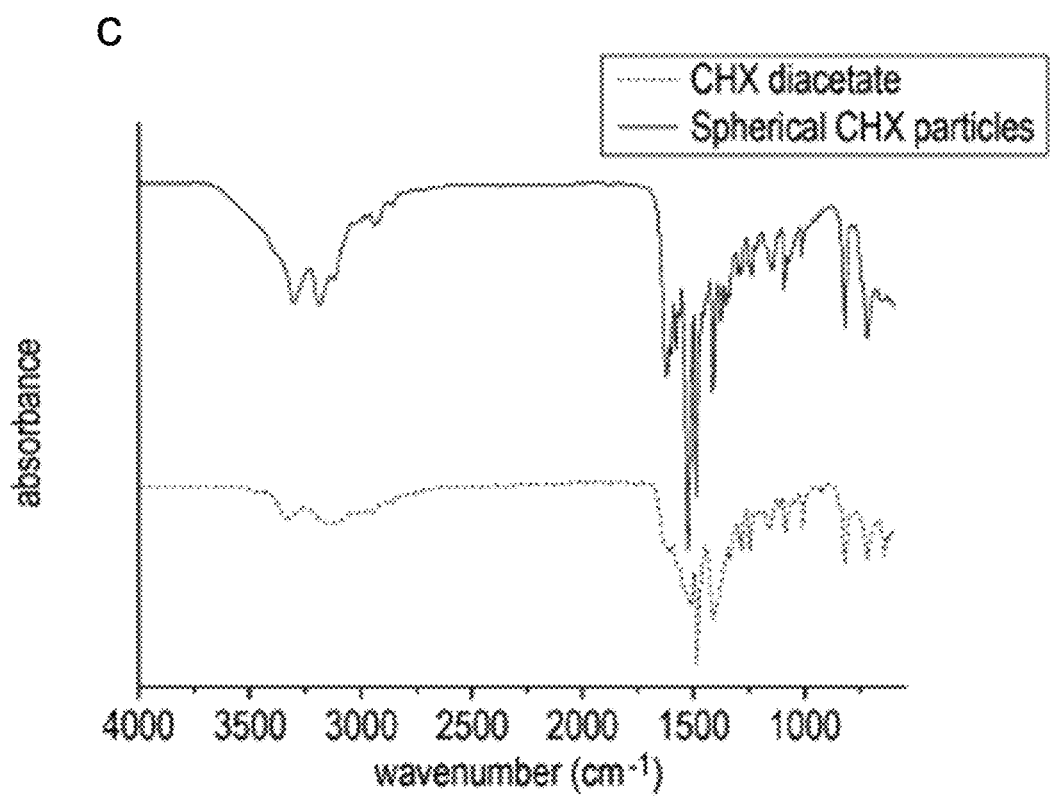
Figure 4:
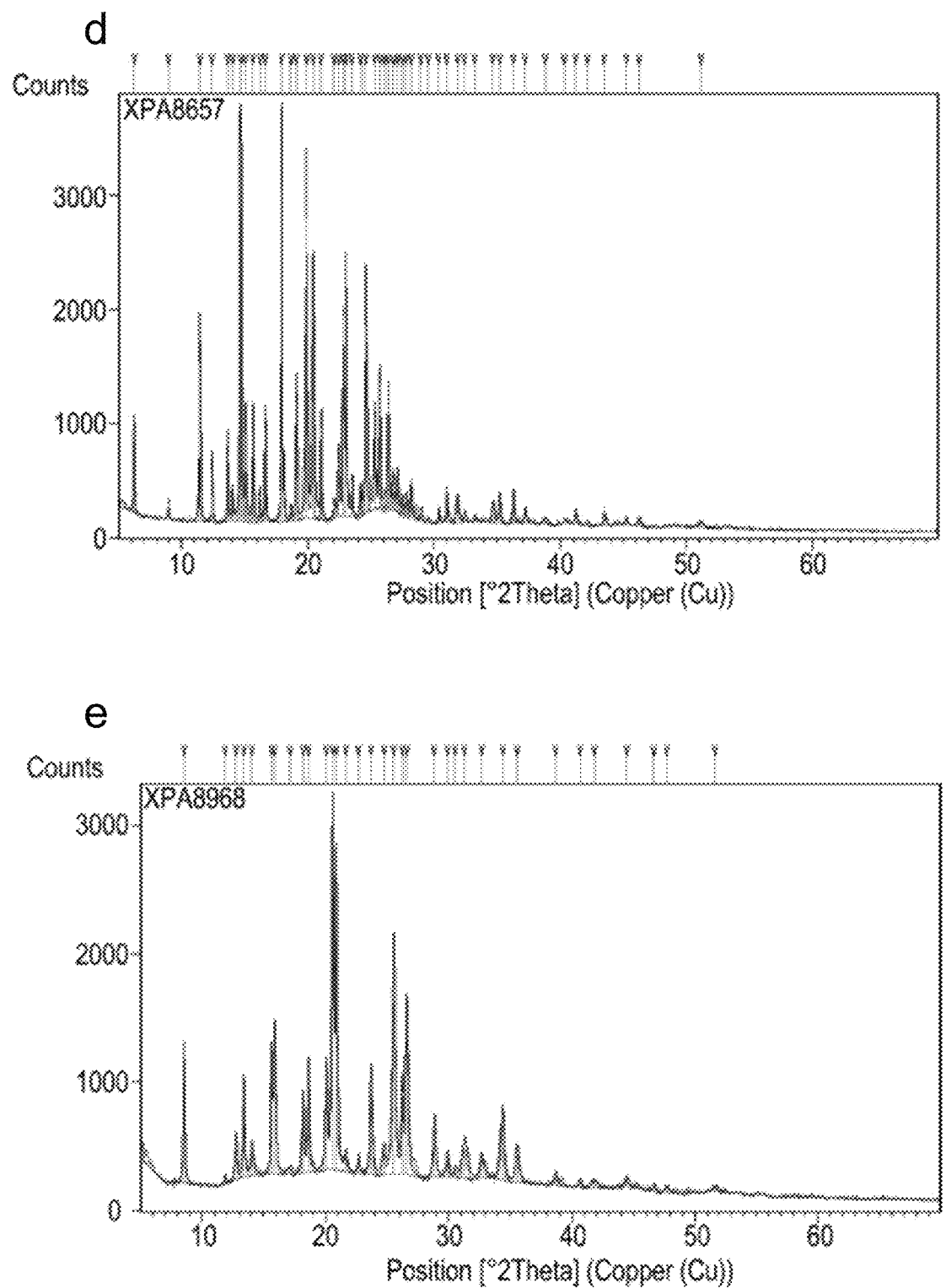
Figure 4:
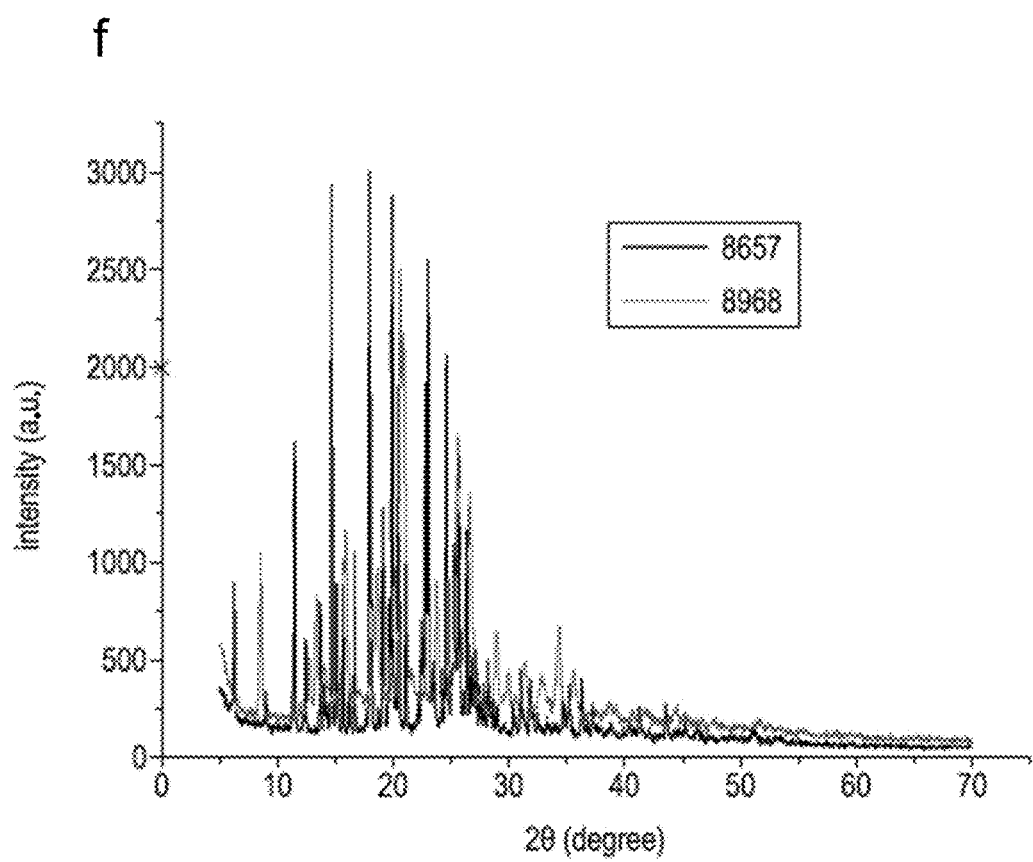

There was a clear change in the 2 theta positions (missing peaks, peak shifts, peak broadening) and the peak intensities when the chlorhexidine chloride compounds were compared to the chlorhexidine diacetate powder (FIG. 4, panels (d)-(f)). XRD peak fitting and plots generated by Panalytical's X'Pert HighScore software (FIG. 4, panels (d)-(e)) and the resultant data can be seen in Tables 2-3. The data for the chlorhexidine diacetate and the spherical chlorhexidine chloride compound was overlapped to further illustrate these distinct differences in peaks/peak positions. The XRD indicates clear crystal structural differences in the new spherical compounds (FIG. 4, panels (d)-(g), Tables 2-3) and the peak broadening (FIG. 4, panel (e)) is in agreement with the smaller particle size (FIG. 3, panel (d), Table 1), for the Spherical chlorhexidine chloride particles in comparison to chlorhexidine diacetate (FIG. 3, panel (g)).

Table 1 shows size distribution of the porous chlorhexidine chloride particles at different CaCl$_2$ (M) concentration (CHX=Chlorhexidine Diacetate).

TABLE 1

| Compounds | Particle Diameter Range/μm | Mean (SD) Particle Diameter (μm) |
|---|---|---|
| 0.5M CaCl$_2$/CHX | 9.8-41.3 | 21.8 (8.9) |
| 0.33M CaCl$_2$/CHX | 12.7-28.4 | 19.9 (3.1) |
| 0.25M CaCl$_2$/CHX | 11.9-30.4 | 18.0 (5.1) |
| 0.125M CaCl$_2$/CHX | 19.1-46.4 | 26.8 (5.9) |

Table 2 shows XRD data for the spherical chlorhexidine chloride compound (X8968) of the invention from peak fit in FIG. 4, panel (e)).

TABLE 2

| No. | Pos. [°2Th.] | FWHM Left [°2Th.] | Area [cts * °2Th.] | Derivation | Backgr. [cts] | d-spacing [Å] | Height [cts] | Rel. Int. [%] |
|---|---|---|---|---|---|---|---|---|
| 1 | 8.5284 | 0.1624 | 125.84 | KA1 + KA2 | 222.06 | 10.36826 | 785.71 | 36.77 |
| 2 | 11.8562 | 0.1299 | 6.69 | KA1 + KA2 | 217.04 | 7.46451 | 52.22 | 2.44 |
| 3 | 12.7439 | 0.1948 | 49.93 | KA1 + KA2 | 250.56 | 6.94647 | 259.78 | 12.16 |
| 4 | 13.3831 | 0.1624 | 89.61 | KA1 + KA2 | 267.95 | 6.61611 | 559.51 | 26.18 |
| 5 | 14.0627 | 0.2273 | 41.72 | KA1 + KA2 | 280.07 | 6.29788 | 186.06 | 8.71 |
| 6 | 15.6231 | 0.1299 | 87.5 | KA1 + KA2 | 293.31 | 5.67217 | 682.94 | 31.96 |
| 7 | 15.8765 | 0.1948 | 162.5 | KA1 + KA2 | 294.45 | 5.58223 | 845.53 | 39.57 |
| 8 | 17.132 | 0.4546 | 18.11 | KA1 + KA2 | 289.53 | 5.17587 | 40.37 | 1.89 |
| 9 | 18.1846 | 0.1624 | 76.13 | KA1 + KA2 | 301.61 | 4.87855 | 475.32 | 22.24 |
| 10 | 18.608 | 0.1624 | 105.86 | KA1 + KA2 | 307.79 | 4.76849 | 660.95 | 30.93 |
| 11 | 20.0646 | 0.1948 | 117.23 | KA1 + KA2 | 323.86 | 4.42549 | 609.95 | 28.54 |
| 12 | 20.581 | 0.1624 | 342.24 | KA1 + KA2 | 324.93 | 4.31561 | 2136.89 | 100 |
| 13 | 20.8828 | 0.1624 | 293.87 | KA1 + KA2 | 323 | 4.25392 | 1834.83 | 85.86 |
| 14 | 21.6598 | 0.1948 | 22.42 | KA1 + KA2 | 312.21 | 4.10305 | 116.63 | 5.46 |
| 15 | 22.676 | 0.1299 | 15.55 | KA1 + KA2 | 299.44 | 3.92141 | 121.34 | 5.68 |
| 16 | 23.7094 | 0.2273 | 138.79 | KA1 + KA2 | 290.44 | 3.75279 | 619 | 28.97 |
| 17 | 24.7554 | 0.2598 | 39.04 | KA1 + KA2 | 288.42 | 3.59654 | 152.35 | 7.13 |
| 18 | 25.539 | 0.2598 | 344.99 | KA1 + KA2 | 295.67 | 3.48794 | 1346.26 | 63 |
| 19 | 26.2153 | 0.0974 | 61.89 | KA1 + KA2 | 292.84 | 3.39947 | 644.07 | 30.14 |
| 20 | 26.5833 | 0.2273 | 227.73 | KA1 + KA2 | 289.41 | 3.35324 | 1015.64 | 47.53 |
| 21 | 28.8482 | 0.2273 | 79.71 | KA1 + KA2 | 272.22 | 3.09493 | 355.51 | 16.64 |
| 22 | 29.929 | 0.1948 | 28.27 | KA1 + KA2 | 273.91 | 2.98558 | 147.12 | 6.88 |
| 23 | 30.5457 | 0.1948 | 10.38 | KA1 + KA2 | 267.02 | 2.92669 | 54 | 2.53 |
| 24 | 31.314 | 0.5196 | 114.91 | KA1 + KA2 | 257.91 | 2.85661 | 224.22 | 10.49 |
| 25 | 32.6717 | 0.3247 | 43.35 | KA1 + KA2 | 258.1 | 2.74094 | 135.34 | 6.33 |
| 26 | 34.3648 | 0.2922 | 121.44 | KA1 + KA2 | 247.31 | 2.60968 | 421.23 | 19.71 |
| 27 | 35.544 | 0.2922 | 61.08 | KA1 + KA2 | 227.81 | 2.52576 | 211.88 | 9.92 |
| 28 | 38.6824 | 0.2598 | 22.42 | KA1 + KA2 | 199.99 | 2.32776 | 87.5 | 4.09 |
| 29 | 40.6513 | 0.2598 | 13.04 | KA1 + KA2 | 186.68 | 2.21945 | 50.88 | 2.38 |
| 30 | 41.8311 | 0.5196 | 23.23 | KA1 + KA2 | 185.91 | 2.15954 | 45.33 | 2.12 |
| 31 | 44.489 | 0.3247 | 20.37 | KA1 + KA2 | 188.91 | 2.0365 | 63.61 | 2.98 |
| 32 | 46.6755 | 0.1948 | 9.89 | KA1 + KA2 | 154.03 | 1.94607 | 51.46 | 2.41 |
| 33 | 47.7001 | 0.3897 | 14.91 | KA1 + KA2 | 142.74 | 1.90663 | 38.79 | 1.82 |
| 34 | 51.6347 | 0.5196 | 15.93 | KA1 + KA2 | 153.07 | 1.77022 | 31.09 | 1.45 |

Table 3 shows XRD data for the commercially available chlorhexidine diacetate (X8657) from peak fit in FIG. 4, panel (d)).

TABLE 3

| No. | Pos. [°2Th.] | FWHM Left [°2Th.] | Area [cts * °2Th.] | Derivation | Backgr. [cts] | d-spacing [Å] | Height [cts] | Rel. Int. [%] |
|---|---|---|---|---|---|---|---|---|
| 1 | 6.2234 | 0.0974 | 60.89 | KA1 + KA2 | 224.23 | 14.20235 | 633.66 | 21.16 |
| 2 | 8.9532 | 0.0974 | 13.42 | KA1 + KA2 | 165.08 | 9.87725 | 139.65 | 4.66 |
| 3 | 11.4494 | 0.0974 | 137.62 | KA1 + KA2 | 145.27 | 7.72879 | 1432.06 | 47.82 |
| 4 | 12.4233 | 0.0974 | 45.08 | KA1 + KA2 | 139.87 | 7.12503 | 469.13 | 15.67 |
| 5 | 13.646 | 0.0974 | 57.45 | KA1 + KA2 | 142.87 | 6.48924 | 597.86 | 19.96 |
| 6 | 14.0112 | 0.0974 | 21.49 | KA1 + KA2 | 148.06 | 6.3209 | 223.59 | 7.47 |
| 7 | 14.66 | 0.1299 | 356.8 | KA1 + KA2 | 145.76 | 6.04258 | 2784.71 | 92.99 |
| 8 | 15.0586 | 0.0974 | 76.91 | KA1 + KA2 | 138.72 | 5.88353 | 800.3 | 26.72 |
| 9 | 15.6439 | 0.1299 | 103.03 | KA1 + KA2 | 130.01 | 5.66469 | 804.1 | 26.85 |
| 10 | 16.1844 | 0.0974 | 22.5 | KA1 + KA2 | 138.29 | 5.47669 | 234.15 | 7.82 |
| 11 | 16.621 | 0.0974 | 78.81 | KA1 + KA2 | 141.68 | 5.33382 | 820.11 | 27.39 |
| 12 | 17.9333 | 0.0974 | 287.78 | KA1 + KA2 | 138.71 | 4.94637 | 2994.71 | 100 |
| 13 | 18.6659 | 0.0974 | 10.27 | KA1 + KA2 | 143.93 | 4.75384 | 106.88 | 3.57 |
| 14 | 19.0893 | 0.0974 | 102.75 | KA1 + KA2 | 148.82 | 4.64935 | 1069.28 | 35.71 |
| 15 | 19.8791 | 0.0974 | 259.33 | KA1 + KA2 | 168.86 | 4.46638 | 2698.67 | 90.11 |
| 16 | 20.4133 | 0.1948 | 326.74 | KA1 + KA2 | 167.91 | 4.35068 | 1700.05 | 56.77 |
| 17 | 21.04 | 0.0974 | 78.33 | KA1 + KA2 | 160.88 | 4.2225 | 815.16 | 27.22 |
| 18 | 22.0836 | 0.1299 | 16.01 | KA1 + KA2 | 172.63 | 4.02526 | 124.94 | 4.17 |
| 19 | 22.4239 | 0.1299 | 63.26 | KA1 + KA2 | 183.68 | 3.96494 | 493.7 | 16.49 |
| 20 | 22.7781 | 0.0649 | 114.62 | KA1 + KA2 | 188.21 | 3.90407 | 1789.16 | 59.74 |
| 21 | 22.9936 | 0.0974 | 192.26 | KA1 + KA2 | 189.67 | 3.86797 | 2000.75 | 66.81 |
| 22 | 23.5057 | 0.0974 | 30.35 | KA1 + KA2 | 182.74 | 3.78484 | 315.85 | 10.55 |
| 23 | 24.1865 | 0.0974 | 21.06 | KA1 + KA2 | 185.22 | 3.67983 | 219.18 | 7.32 |
| 24 | 24.6119 | 0.1624 | 268.9 | KA1 + KA2 | 218.71 | 3.61718 | 1678.94 | 56.06 |
| 25 | 25.2928 | 0.0974 | 80.16 | KA1 + KA2 | 251.9 | 3.52133 | 834.15 | 27.85 |
| 26 | 25.6954 | 0.0974 | 107.75 | KA1 + KA2 | 259.44 | 3.46707 | 1121.3 | 37.44 |
| 27 | 26.0834 | 0.1299 | 10.08 | KA1 + KA2 | 259.03 | 3.41637 | 78.68 | 2.63 |
| 28 | 26.3604 | 0.1299 | 115.65 | KA1 + KA2 | 256.54 | 3.38109 | 902.64 | 30.14 |
| 29 | 26.7433 | 0.1299 | 34.79 | KA1 + KA2 | 246.56 | 3.33354 | 271.55 | 9.07 |
| 30 | 27.1024 | 0.1624 | 47.26 | KA1 + KA2 | 229.47 | 3.29019 | 295.06 | 9.85 |
| 31 | 27.4738 | 0.1299 | 16.45 | KA1 + KA2 | 205.15 | 3.24654 | 128.36 | 4.29 |
| 32 | 27.7944 | 0.1299 | 21.45 | KA1 + KA2 | 190.13 | 3.20982 | 167.44 | 5.59 |
| 33 | 28.1548 | 0.0974 | 29.27 | KA1 + KA2 | 184.1 | 3.16955 | 304.57 | 10.17 |
| 34 | 28.9676 | 0.1624 | 15.82 | KA1 + KA2 | 149.5 | 3.08244 | 98.79 | 3.3 |
| 35 | 29.5084 | 0.1948 | 7.62 | KA1 + KA2 | 128.91 | 3.02716 | 39.65 | 1.32 |
| 36 | 30.3379 | 0.0974 | 13.2 | KA1 + KA2 | 130.48 | 2.94626 | 137.34 | 4.59 |
| 37 | 31.0052 | 0.0974 | 27.34 | KA1 + KA2 | 135.83 | 2.88436 | 284.47 | 9.5 |
| 38 | 31.8492 | 0.1948 | 37.11 | KA1 + KA2 | 131.56 | 2.80983 | 193.09 | 6.45 |
| 39 | 32.4188 | 0.1299 | 10.57 | KA1 + KA2 | 138.35 | 2.76175 | 82.46 | 2.75 |
| 40 | 33.2274 | 0.0974 | 6.75 | KA1 + KA2 | 145.77 | 2.69636 | 70.29 | 2.35 |
| 41 | 34.6577 | 0.1948 | 28.35 | KA1 + KA2 | 135.49 | 2.58829 | 147.53 | 4.93 |
| 42 | 35.2027 | 0.1299 | 30.78 | KA1 + KA2 | 129.65 | 2.54946 | 240.26 | 8.02 |
| 43 | 36.268 | 0.1299 | 35.52 | KA1 + KA2 | 125.68 | 2.47698 | 277.19 | 9.26 |
| 44 | 37.202 | 0.1624 | 19.1 | KA1 + KA2 | 132.77 | 2.41691 | 119.24 | 3.98 |
| 45 | 38.775 | 0.5196 | 20.98 | KA1 + KA2 | 116.32 | 2.32241 | 40.94 | 1.37 |
| 46 | 40.3343 | 0.1948 | 7.11 | KA1 + KA2 | 122.89 | 2.23616 | 37 | 1.24 |
| 47 | 41.2135 | 0.1299 | 15.94 | KA1 + KA2 | 119.76 | 2.19046 | 124.37 | 4.15 |
| 48 | 42.1225 | 0.2598 | 9.04 | KA1 + KA2 | 100 | 2.14527 | 35.28 | 1.18 |
| 49 | 43.4935 | 0.0974 | 15.84 | KA1 + KA2 | 106.58 | 2.08078 | 164.88 | 5.51 |
| 50 | 45.2416 | 0.1299 | 7.88 | KA1 + KA2 | 113 | 2.00436 | 61.53 | 2.05 |
| 51 | 46.2599 | 0.1948 | 12.11 | KA1 + KA2 | 106.15 | 1.96258 | 63 | 2.1 |
| 52 | 51.1614 | 0.3897 | 14.99 | KA1 + KA2 | 92.68 | 1.78548 | 38.99 | 1.3 |

Example 2(b)

To evaluate the influence of temperature on spherical chlorhexidine chloride particle formation, 15 mg/ml chlorhexidine diacetate and 0.33 M $CaCl_2$ solutions were kept in ice bath and the temperature of solutions were monitored. At 1, 5, 10, 15, 20 and 25° C. specifically, the solutions were mixed and the sedimentation were washed with corresponding $CaCl_2$ solution three times (the same as Example 2), and then characterized with SEM. The particle size of spherical chlorhexidine chloride compounds prepared at different temperatures was analysed according to the SEM images using a particle size analyser (Nano Measurer, 1.2).

Figure 5:
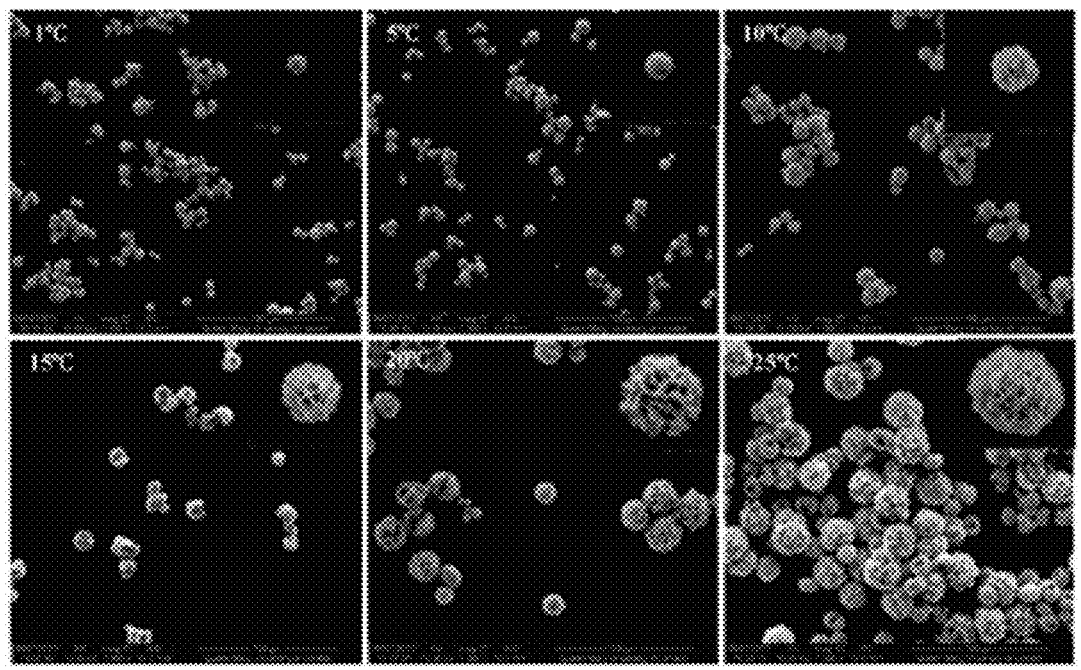
FIG. 5 shows the influence of temperature on the morphology and Mean diameter (SD) of chlorhexidine chloride spheres.
Figure 6:
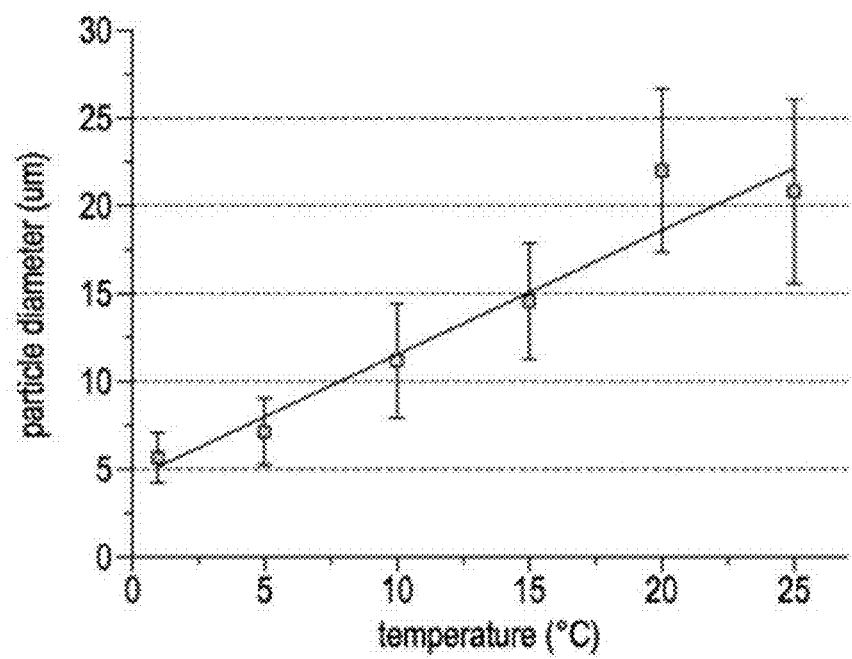
FIG. 6 shows a correlation between Mean (SD) particle diameter and temperature.

FIG. 5 shows the influence of temperature on the morphology and mean diameter (SD) of chlorhexidine chloride spheres. As the temperature increased the size of chlorhexidine chloride particles also increased (FIG. 6). At 1° C., very small particles with Mean diameter (SD) of 5.6 (1.5) μm were observed, and with a similar spherical microstructure seen in Example 2. The spheres grew as the temperature increased, until 25° C. when the highly porous particles had a Mean (SD) diameter of 20.8 (5.3) μm. Comparing the particles morphology/diameter at different temperatures, the average particles diameter did have a linear relation ($r^2$=0.948) with temperature (FIG. 6).

Example 2(c)

When Substituting $CaCl_2$ with $SrCl_2$ (Sigma-Aldrich, 255521, Lot: MKBC8822V) the same spherical structure as in Examples 2 and 3 could be formed (FIG. 7, panel (a)). As in Example 2, the Chlorhexidine diacetate concentration was fixed at 15 mg/ml and concentrations of $SrCl_2$ was fixed at 0.33M, and they were mixed using a pipette at the volume ratio of 1:1. The mixtures were shaken for 1 min, and then centrifuged at 2000 rpm for 1 min (Eppendorf centrifuge 5417C, Germany), and washed three times in 0.33 M $SrCl_2$ solution, to reduce the dissolution of the particles. Morphology of compounds was characterized with SEM and presence of strontium was confirmed with energy dispersive spectrometer (EDX).

Figure 7:
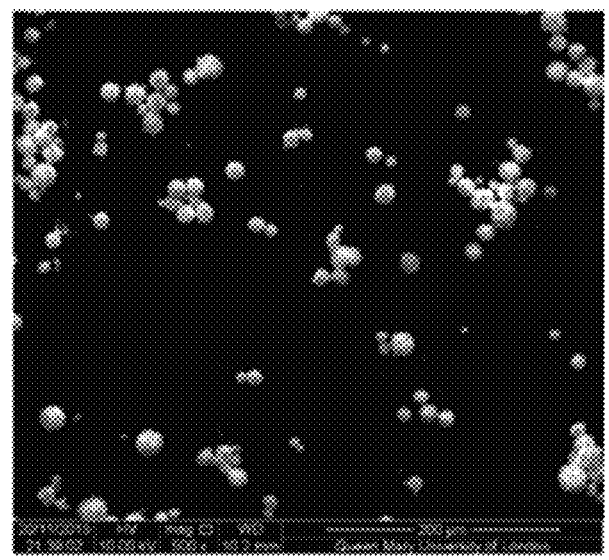
FIG. 7, panels (a)-(b) show SEM results of substituting $CaCl_2$ with $SrCl_2$ FIG. 7, panel (a)) and the respective particle size diameter distribution FIG. 7, panel (b)).
Figure 7:
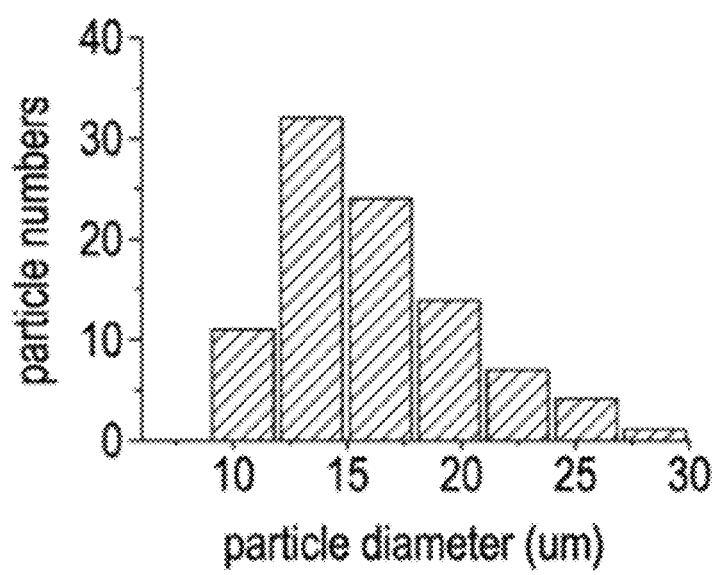
Figure 8:
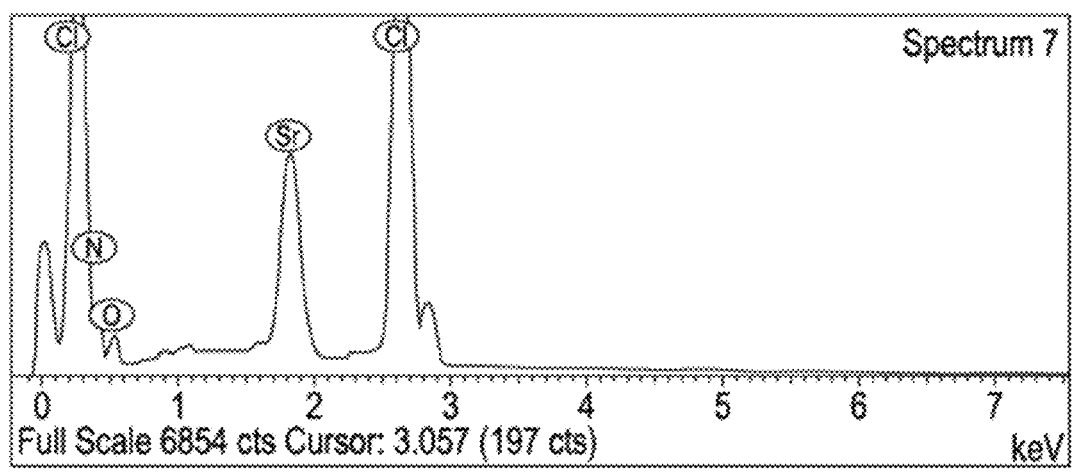
FIG. 8 shows the EDX spectrum for the chlorhexidine chloride ($SrCl_2$) salt formed.

The morphology of chlorhexidine compound made from $SrCl_2$ is showed in FIG. 7, panel (a), and a similar porous structure was observed. The particle size diameter distribution is shown in FIG. 7, panel (b). The Mean (SD) diameter of 16.2 (4.2) μm, was found for the $SrCl_2$/chlorhexidine compound. According to the EDX spectrum, strontium was contained within the chlorhexidine sphere structure, as a strong peak for strontium was identified (FIG. 8). Strontium has been shown to be anti-bacterial in nature and promotes bone proliferation by stimulating osteoblast cells, which makes it particularly useful in the treatment of implant associated infections. Strontium has also been shown to impart radiopacity to materials allowing them to be clinically detected using radiographs.

Example 3

Magnetic nano-particles and gold nano-particles (Mean diameter=20 nm, sigma, 741965, Lot: MKBH7375V) were incorporated into the chlorhexidine chloride compounds (Example 2, precipitated with 0.33 M $CaCl_2$). Iron oxide nano-particles ($Fe_3O_4$) were synthesized by mixing 2.35 g $FeCl_3$ (Fluka, 44944, Lot: 30607125) and 0.86 g $FeCl_2$ (Fluke, 44939, Lot: 24606139) in 40 ml $H_2O$ in a three-neck flask, which was placed in an oil bath and heated up to 80° C. in an argon atmosphere. The mixture was next stirred using a magnetic stirrer (VWR Stirrer, USA), at a rate of 800 rpm, whilst 5 ml $NH_4OH$ (Sigma, 320145) was added slowly with a syringe. Heating was then maintained at 80° C. for 30 mins and then 2 ml of 0.5 g/ml citric acid (Sigma, 27490, Lot: 23405C03) was introduced. The temperature was next raised to 95° C. and held for 90 mins. The magnetic nano-particles were dialysed against $H_2O$ in a 14 kDa cut-off membrane (Sigma, D9527) for one week. Nano-particles specifically, 200 ul of $Fe_3O_4$ or the Au nano-particle suspensions were mixed with 1 ml of 0.33 M of $CaCl_2$ solution, and then the mixture was added to 1 ml of chlorhexidine diacetate. The following steps were the same as the synthesis of the chlorhexidine chloride particles in Example 2. The mixture was shaken for 1 min, and then centrifuged at 2000 rpm for 1 min (Eppendorf centrifuge 5417C, Germany), followed by washing the sediment three times in 0.33 M $CaCl_2$ solution, to reduce the dissolution of the particles.

Figure 9:
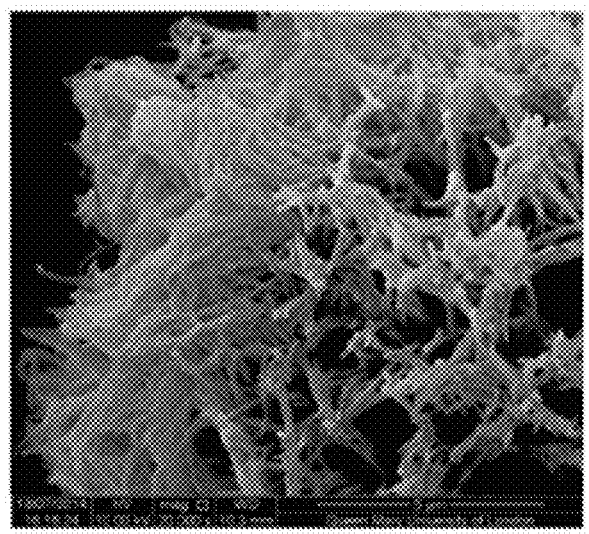
FIG. 9 shows SEM image of spherical chlorhexidine chloride compounds functionalised with gold nano-particles.
Figure 10:
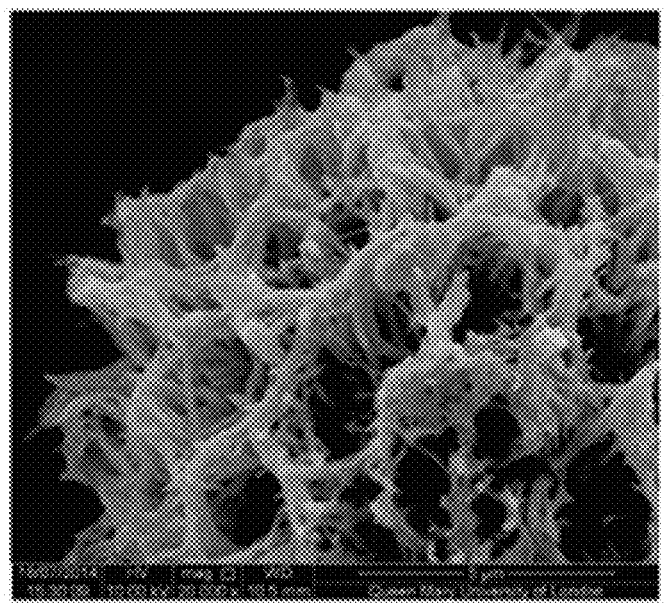
FIG. 10, panel (a) shows SEM photomicrograph of spherical chlorhexidine chloride compounds functionalised with iron oxide nano-particles.
Figure 10:
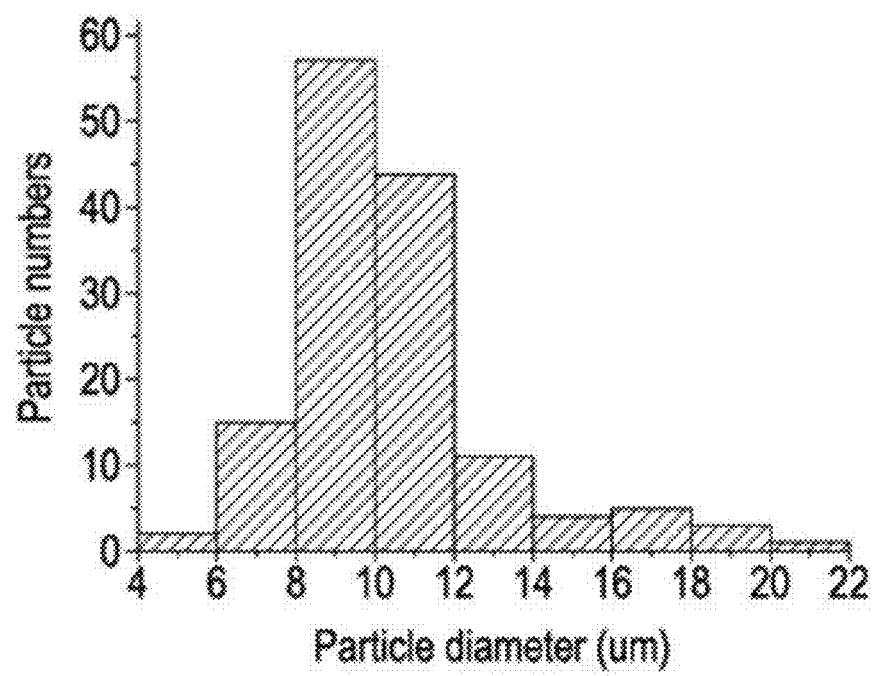
Figure 10:
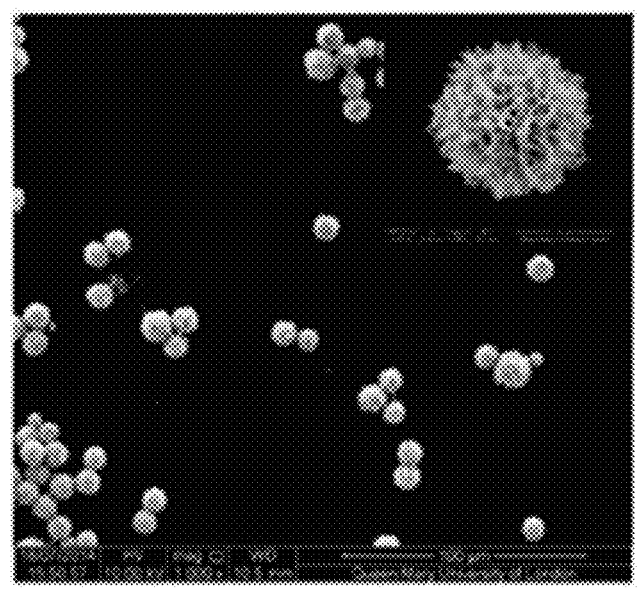

The morphology of the $Fe_3O_4$ and Au nano-particle loaded chlorhexidine chloride compounds are shown in FIGS. 9 and 10 (panels (a)-(c)). The nano-particle loaded chlorhexidine chloride compounds had a similar structure and size to the chlorhexidine chloride compounds in Example 2 FIG. 3, panel (d)). The addition of gold and $Fe_3O_4$ nano-particles affected the nucleation of the chlorhexidine chloride compounds as there was a statistically significant (p<0.001) reduction in the average (SD) particle diameter to 10.4 (2.6) μm FIG. 10, panels (b) and (c)) compared with Example 2(a) (19.9 (3.1) μm, without the dispersion of $Fe_3O_4$ nano-particles. SEM photomicrographs indicated Au nano-particles (FIG. 9) and $Fe_3O_4$ nano-particles (FIG. 10, panel (a)) clustered at the outer edges of the crystallite structures.

Example 4

Poly (allylamine hydrochloride) (PAH, 70 kDa) (Sigma-Aldrich, 283223, Lot: MKBJ4274V) and Poly (styrene-sulfonate sodium salt) (PSS, 70 kDa) (Sigma-Aldrich, 243051, Lot: BCBF6120V) were assembled on the chlorhexidine chloride compounds surface (Example 2, precipitated with 0.33 M $CaCl_2$) via electrostatic interaction. Specifically the chlorhexidine chloride compounds were synthesized as in Example 2. The mixtures were shaken for 1 min, suspended in a 2 ml tube and centrifuged at the speed of 2000 rpm for 1 min, and then 2 ml PAH solution with a concentration of 2 mg/ml was added as the first layer. The mixture was re-suspended with a pipette and shaken (Vortex-Genie 2, Germany) for 10 min. Then the mixture was centrifuged (2000 rpm) and washed with 0.33 M $CaCl_2$ solution (3 times) to remove the excess PAH. The second PSS layer was assembled using the same procedure. After assembling 8 layers, the encapsulated chlorhexidine compound with the structure Chlorhexidine/$(PAH/PSS)_4$ was produced. To prevent dissolution all the assembly and wash steps were carried out in a solution of 0.33 M $CaCl_2$.

Figure 11:
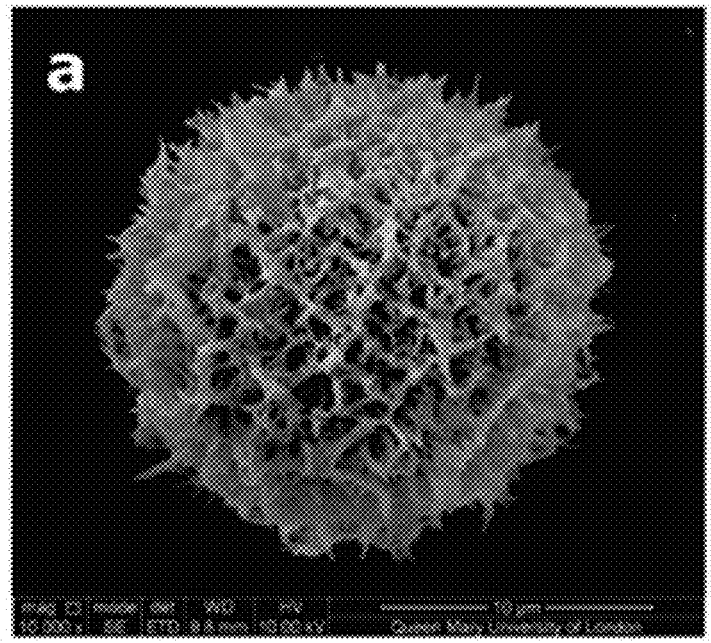
FIG. 11, panel (a) shows SEM photomicrograph of spherical chlorhexidine chloride compound before encapsulation.
Figure 11:
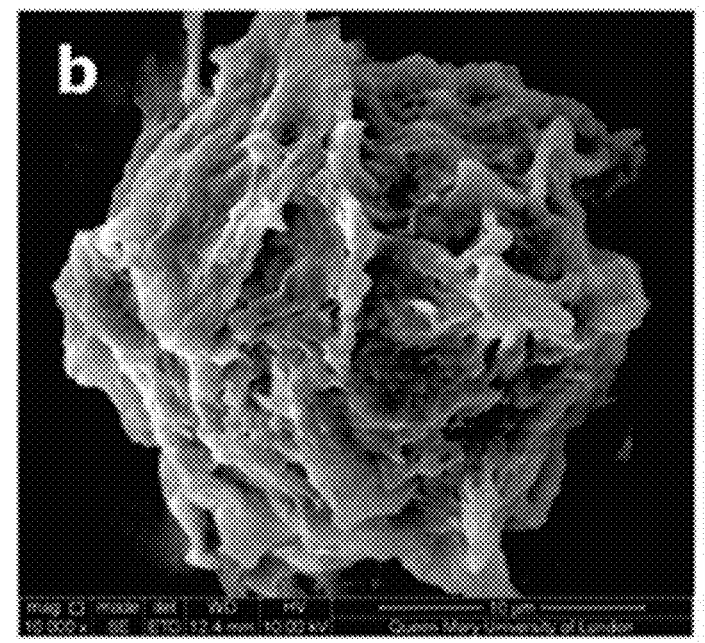
Figure 11:
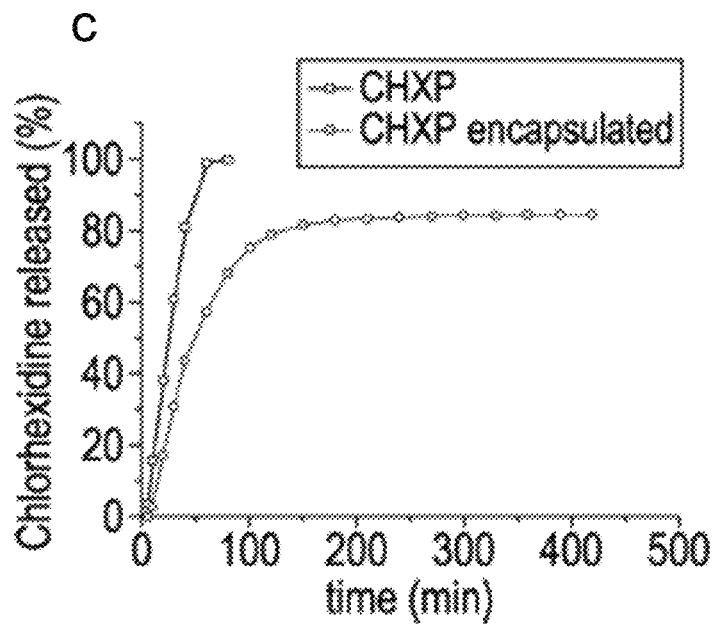
Figure 11:
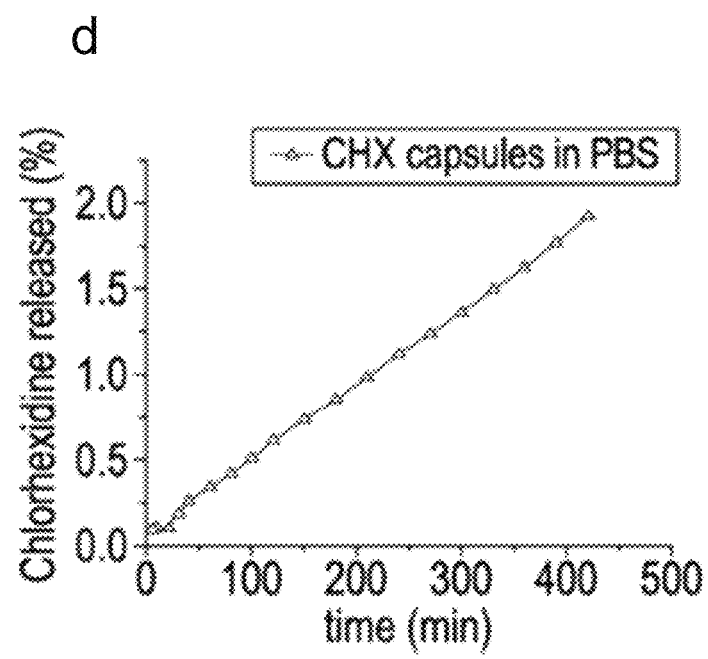

The spherical chlorhexidine compound before and after being encapsulated with polyelectrolytes is shown in FIG. 11, panels (a) and (b). Before encapsulation, individual chlorhexidine chloride particles/precipitates were spherical and had a porous inter-connected surface morphology (FIG. 11, panel (a)). However, after encapsulation polyelectrolyte flakes could be seen on the surface, with the original structure covered (FIG. 11, panel (b)). Polyelectrolyte shells stabilize the particles and slow down the release of chlorhexidine in $H_2O$ as shown in FIG. 11, panel (c). In order to measure chlorhexidine release over 400 mins, samples were water stored and agitated (Vortex-Genie 2, Germany) for the whole time period. The uncoated particles resulted in dissolution within 1 hour, however the encapsulated particles gave sustained chlorhexidine release after 7 hours FIG. 11, panel (c)). Replacing the $H_2O$ with artificial saliva (PBS) resulted in a lower release rate, linear release kinetics and prolonged release process (2% chlorhexidine released after 7 hours). There was a linear relationship between chlorhexidine release and time (r2=0.99, FIG. 11, panel (d)). The encapsulation process demonstrated shows a viable method of controlling release in the new chlorhexidine compounds.

Example 5

HEMA-UDMA resin was prepared by mixing 64% urethane dimethacrylate (UDMA) (Esschem UK, Lot: 591-22) and 36% hydroxyethyl methacrylate (HEMA) (Aldrich, 128635, Lot: STBC7495V), 0.08% of N,N-dimethyl-P-toluidine (Acros Organics, Lot: A0207283001) and 0.05% dimethylamino ethyl methacrylate (Aldrich, 234907, Lot: BCBF8391V) were added. The mixture was then stirred for 15 min (800 rpm, VWR Stirrer, USA). Finally, camphorquinone (Aldrich, 12, 489-3, Lot: 2338141) was added at the proportion of 0.1%. The mixture was stirred for another 15 min (VWR Stirrer, USA), and then the viscous liquid resin was prepared. Freeze dried chlorhexidine chloride compounds produced in Example 2 (precipitated with 0.33 M $CaCl_2$)) were weighed and incorporated within the resin at a loading level of 5% by weight. To explore the effect of different morphology on the release kinetics, chlorhexidine compounds with spherical, needle and flake morphology (from Example 1, FIG. 1, panels (b) and (c)) were incorporated into the resin. Incorporation of the chlorhexidine compounds within the resin was carried out by rotating the mixture contained in a 1 ml tube for 15 s in a Rotomix (120V/60 Hz, 2850 rotations/min) (ESPE RotoMix, USA). Chlorhexidine diacetate was also incorporated in the prepared resin in the same way, with loading rates of 5%, 10% and 15% (weight %). The filled resin was then placed into a Teflon mould (10 mm in diameter×2 mm thick) and cured through a Mylar film with a curing light (Bluedent LED pen, Bulgaria) (430-490 nm, 600 mW/sq.cm) for 30s. Then the discs were next weighed on a microbalance (Salter Ander-180A weighing scale, UK), and chlorhexidine content in each disc was calculated.

For fluorescent imaging, chlorhexidine diacetate was labelled with Rhodamine B Isothiocyanate dye (TRITC, Sigma, 283924). Chlorhexidine diacetate was dissolved in 45 ml of 0.1 M boric acid (sigma, B6768, Lot: 119K0067) buffer at concentration of 15 mg/ml. Then 5 ml of 1 mg/ml dye ethanol solution was added to the mixture and reacted for 1 day. 100 µl of TRITC labelled chlorhexidine diacetate was mixed with 900 µl of 15 mg/ml unlabelled chlorhexidine diacetate, and then 1 ml of $CaCl_2$ (0.33M) was added using the same procedure in Example 2 and then mixed with the resin as described previously.

Figure 12:
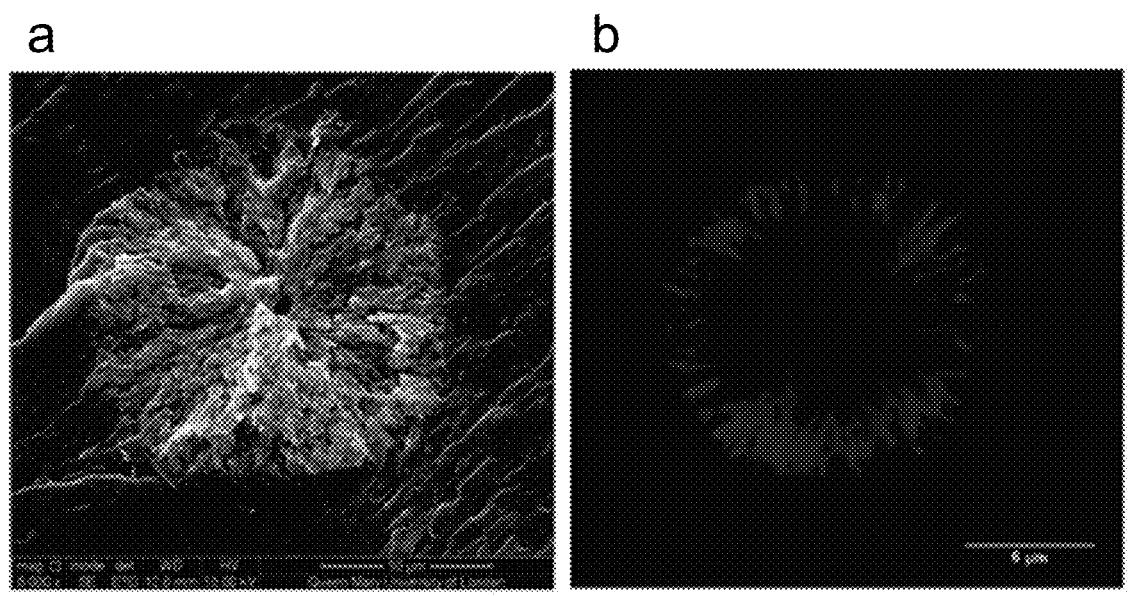
FIG. 12, panel (a) shows SEM photomicrograph of spherical chlorhexidine chloride particles in a HEMA-UDMA polymer.

A cross-section of the chlorhexidine compound doped resin disc is shown in FIG. 12, panel (a). The porous surface morphology allowed liquid resin to penetrate and there was good coherence at the resin/particle interface and minimal cracks or voids were present. Labelled compounds (TRITC) in the resin were demonstrated in FIG. 12, panel (b). Confocal images (Leica TS confocal scanning system, Germany) showed similarly an intact particle with (indicated by red labelling) no evidence of leakage at the particle polymer interface FIG. 12, panel (b)).

Example 6

For the release study, all sample resin discs (HEMA-UDMA) containing chlorhexidine chloride compounds or chlorhexidine diacetate powder prepared in Example 5 were kept in cuvettes containing 3 ml deionized water, and kept at room temperature. And at each time point, solutions were collected for UV absorption tests (Lambda 35, Perkin Elmer, USA) and replaced with fresh deionized water.

For the chlorhexidine chloride compound doped discs (Example 5) chlorhexidine content was fixed at 5%, and ultrasound was exerted. Four groups (five discs in each group) were repetitively treated with ultrasound for 0s, 10s, 20s, 30s, accordingly, by contacting the ultrasound probe (Piezon Master 400, Swiss, 60 Hz, 45VA) on the disc surface at time points of 1h, 3h, 5h, 15h, 25h, 40h, 65h, 95h, 140h, 205h. After that, no ultrasound was carried out for all the groups, but release was carried on until the 650 hour time point. The UDMA-HEMA discs containing needle and flake chlorhexidine compounds and chlorhexidine diacetate FIG. 1, panels (b) and (c), and FIG. 3, panel (g)) were also tested (UV absorption tests) at the same time points (same sample numbers) but without ultrasound treatment. For the chlorhexidine diacetate powder doped discs chlorhexidine content of 5%, 10% and 15% were also analysed, and no ultrasound treatment was carried out.

Figure 13:
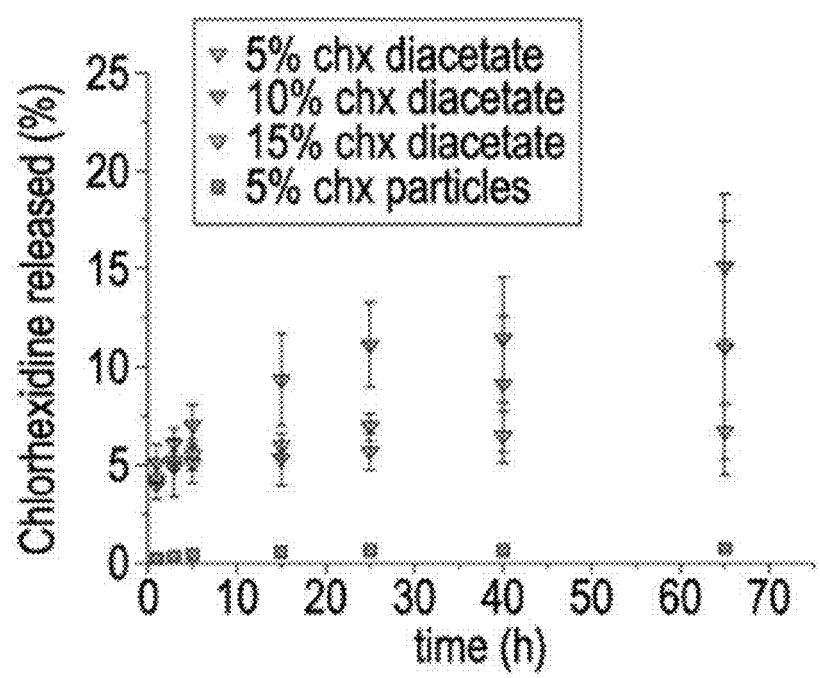
FIG. 13 shows chlorhexidine release curve of chlorhexidine chloride compounds and chlorhexidine diacetate loaded resin discs.

The Release process of the chlorhexidine chloride compound from the resin was much slower and less variable than that of chlorhexidine diacetate (FIG. 13). Within 65 hours, the 0 s group (Example 2, 0.33 M $CaCl_2$) of chlorhexidine chloride compound released only 0.76% chlorhexidine by weight, whereas the 5% chlorhexidine diacetate group released 6.7% (FIG. 13). As the chlorhexidine diacetate content increased the release rate increased to 11.0% and 15.1% for groups containing 10% and 15% chlorhexidine diacetate.

Figure 14:
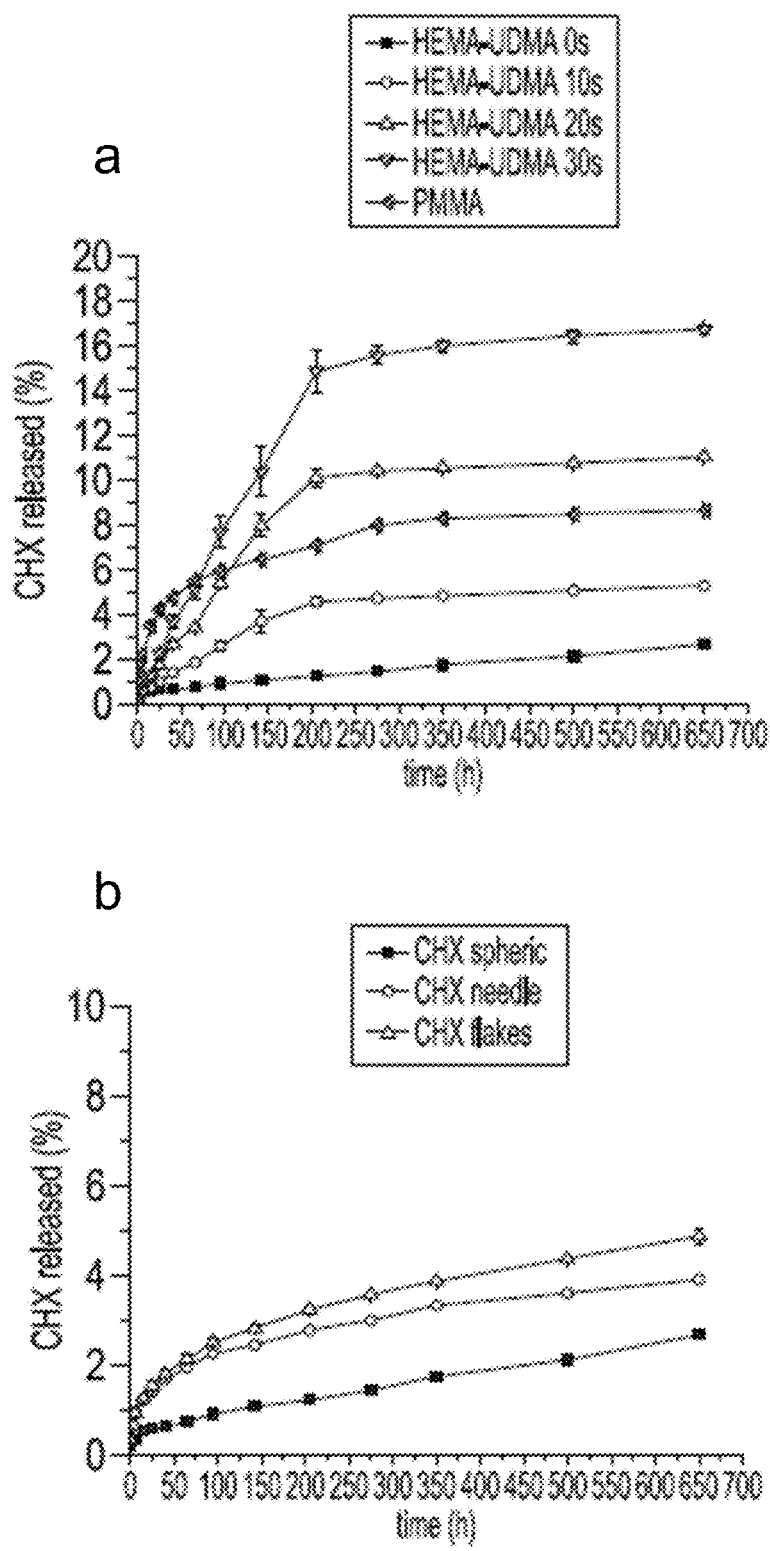
FIG. 14, panel (a) shows chlorhexidine release curve of chlorhexidine chloride compounds loaded in the resin discs and treated with ultrasound for 0s, 10s, 20s and 30s.

The Release of chlorhexidine from the chlorhexidine chloride compound doped resin was accelerated using ultrasound FIG. 14, panel (a)). The longer ultrasound duration led to a higher chlorhexidine release, which by 205 hours was 4.6% (10s), 10.1% (20s) and 14.9% (30s) (FIG. 14, panel (a)). The control group without ultrasound treatment had a release rate of 1.2%. Once sonication was stopped after 205 hours, the release levelled off immediately for the treated groups. The control group (0s) had an increasing release tendency and reached approximate 2.7% chlorhexidine release after 650 hours. This demonstrates the ability to produce a burst or slow controlled/graduated release with the chlorhexidine chloride compound within a resin. According to FIG. 14, panel (b), the different morphology of chlorhexidine compounds in HEMA-UDMA resin had an effect on the release kinetics. Overall, all of the spherical, needle-like and flake compounds could be released slowly, and only 2.7%, 3.9% and 4.8% of chlorhexidine was released after 650 hours, respectively. This clearly indicates that the differing chlorhexidine compound morphology and their distribution were related to different chlorhexidine release kinetics. These differing morphologies and their unique release kinetics can be applied to specific applications to take advantage of these structure-property relations. In particular the flake compositions may be advantageous in Dental composite to prevent carries or for atraumatic restorative treatment applications because of the increased surface area of the flake morphology and increased chlorhexidine release. Needle compositions may be useful for aligning in catheters where its needle aspect ratio would be advantageous.

Example 7

The PMMA resin system was also tested for the release kinetics of spherical chlorhexidine chloride compounds. Specifically, PMMA resin was prepared by mixing the Simplex Rapid Liquid and powder (Kemdent, Lot: 920 758) at a weight ratio of 1:2. The self-cure process took about 15 min. and after which the mixture was filled into a Teflon mould in the same way and pressed (Mestra, Mod.030350). To incorporate the spherical chlorhexidine chloride compounds, they were previously mixed with the Simplex Rapid powder (5% weight of mixture), and the liquid was added.

Compared with the spherical chlorhexidine chloride compounds in HEMA-UDMA, the compounds in PMMA resin had a higher release rate, and after 650 hours, 8% of chlorhexidine was released FIG. 14, panel (a)). There was an initial burst release (100 hours) followed by a gradual chlorhexidine release. This result reveals that spherical chlorhexidine chloride compounds can be released in other resin systems, including the more hydrophilic PMMA system can benefit from the chlorhexidine release. For the more cross linked heat cure PMMA with less residual monomer a reduced chlorhexidine release is expected.

Example 8

$Fe_3O_4$ nanoparticle functionalized spherical chlorhexidine chloride compounds (Example 3) were also incorporated into a HEMA-UDMA resin. The resin composition was the same as described in Example 5. $Fe_3O_4$ nanoparticle functionalized chlorhexidine chloride compounds were incorporated at 5% by weight in the same way as the standard unfunctionalised spherical compounds (Example 5). For the magnetic field treated group, the mixing procedure was the same, but before filling the mixture into the Teflon mould (10 mm in diameter×2 mm thick), a magnet (MACS, Miltenyi Biotech) was placed under the mould. The mould was next filled and left for 10 mins, followed by light curing (Bluedent LED pen, Bulgaria) (430-490 nm, 600 mW/sq.cm) through a Mylar film for 60 s. Then the discs were next weighed on a microbalance (Salter ANDER-180A weighing scale, UK), and the chlorhexidine content in each disc was calculated. A release study of the resin discs containing magnetic chlorhexidine chloride compounds was carried out using the same procedure as in Example 6 (without ultrasonic treatment).

Figure 15:
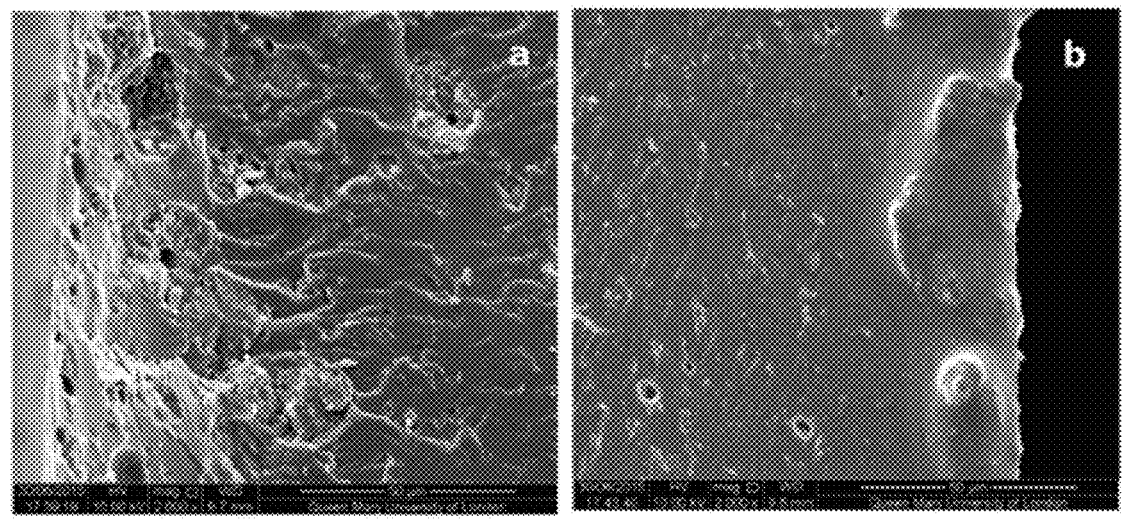
FIG. 15, panels (a)-(b) show SEM photomicrograph of cross-section of magnetic spherical chlorhexidine chloride compounds in HEMA-UDMA with magnetic field treatment of the magnet placed side (panel (a)) and the opposite side (panel (b)).
Figure 16:
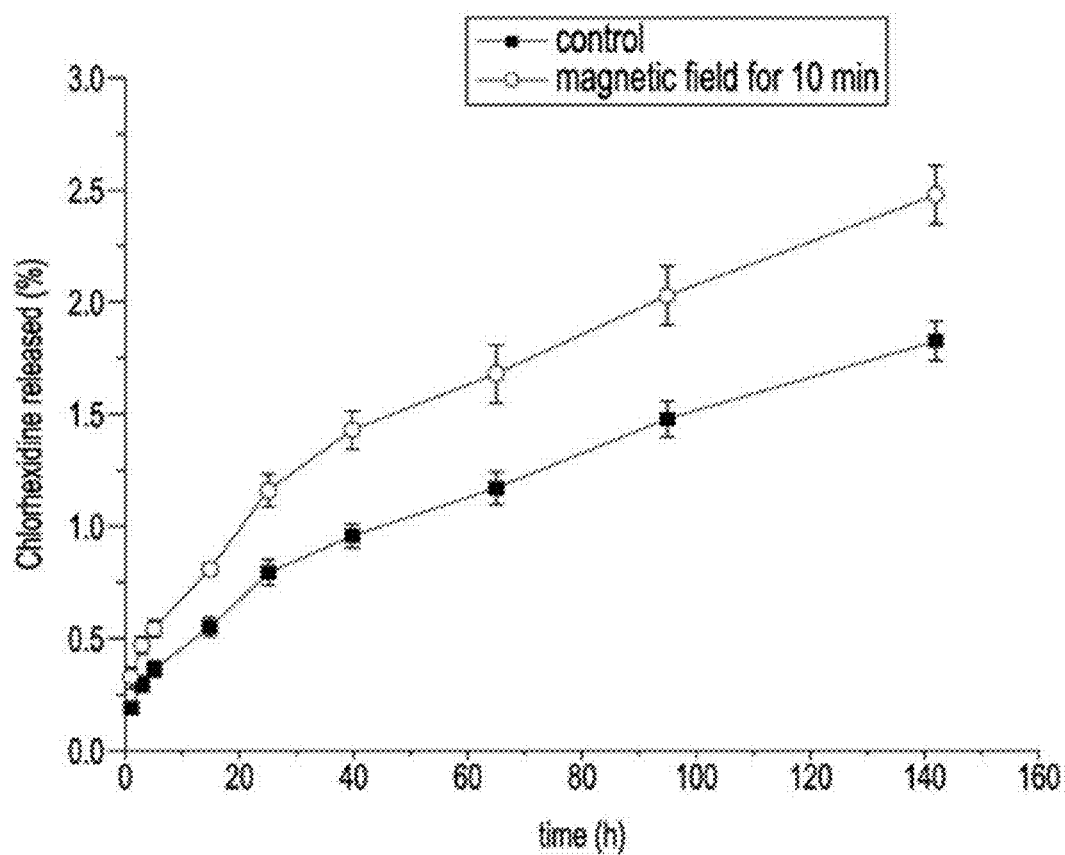
FIG. 16 shows chlorhexidine release curve of the magnetic spherical chlorhexidine chloride compound loaded resin discs.

SEM images of cross-sections of magnetic spherical chlorhexidine chloride compound doped resin are showed in FIG. 15, panels (a) and (b). Without magnetic treatment, the magnetic chlorhexidine chloride compounds had a relatively homogeneous distribution in the resin. However, when the magnetic field was exerted before curing, the magnetic spherical chlorhexidine chloride compounds moved towards the magnet (FIG. 15, panel (a)), where the compounds could be observed. On the contrary, at the opposite site, there were few magnetic spherical chlorhexidine chloride compounds seen (FIG. 15, panel (b)). This demonstrates that the magnetic field attracts the functionalized chlorhexidine chloride compounds to the surface and further alters the release kinetics. As shown in FIG. 16, after 142 hours storage in deionized water (23° C.), the control group discs released 1.8% chlorhexidine, but the magnetic field treated group discs had 2.5% chlorhexidine released.

The different distribution of chlorhexidine compounds in the resin influenced the release kinetics, with more compounds near the surface layer inducing faster release. This example illustrates the ability to move the functionalized chlorhexidine compounds through the resin to create a graduated structure and to control chlorhexidine release at the surface. These compounds can be utilised in the layering of dental or manufactured composites in order to ensure burst or slow release tailored to certain clinical conditions and treatments.

It should also be mentioned that the current invention also relates the functionalisation of dental fillers/glasses and bioactive glasses, so that a magnetic field can be utilised to create graduated microstructures to influence wear, strength and antimicrobial activity. This would also allow the reinforcing of areas after sculpting the restoration in response to a clinical condition. This may be achieved in a polymer as described or induced in a high temperature glass.

Example 9

Electrospinning was utilized to fabricate spherical chlorhexidine chloride compound doped polylactic acid (PLA) fibres. Polylactic acid (Nature works, 2002D) was dissolved in a mixed solvent of chloroform and acetone (3:1 by volume) at 7 wt %. Spherical chlorhexidine chloride compounds were added at 5% weight to the PLA and mixed using a Rotomix. Electrospinning was carried out at room temperature (25° C.), with a pumping rate set at 1 ml/h, working distance at 15 cm, and voltage at 18 kv. Electrospun PLA fibres were collected on a foil. For the chlorhexidine release test, the fibres were weighed (Salter ANDER-180A weighing scale, UK) and divided into cuvettes, and each sample was 25 mg (n=5). Deionized water was added to each cuvette and fibres were kept immersed. Three groups of chlorhexidine chloride compound doped fibres were tested at different temperatures (25, 37 and 60° C.). At each time point (1, 3, 5, 10, 20, 30, 45, 72, 96, 120 h), the solutions were collected for the UV absorption test (Lambda 35, Perkin Elmer, USA) and replaced with fresh deionized water as in Example 6.

Figure 17:
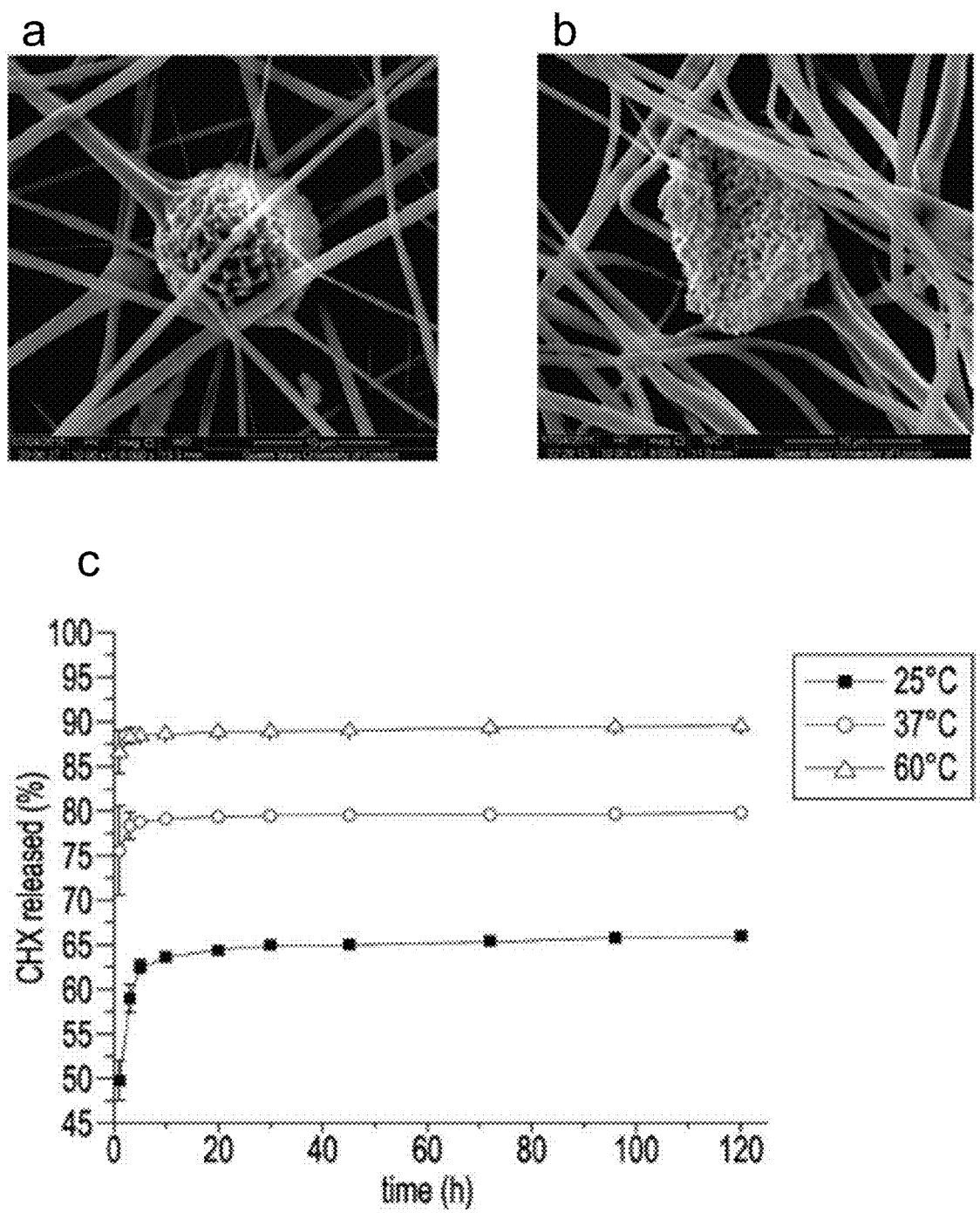
FIG. 17, panel (a) shows SEM photomicrograph of electrospun PLA fibres containing spherical chlorhexidine chloride compounds.

The spherical chlorhexidine chloride compounds were incorporated in PLA fibres and a bead-in-string structure appeared (FIG. 17, panel (a)). The average fibre diameter was much smaller than the chlorhexidine particle size. The spherical chlorhexidine chloride compounds spun in the bead-in-string structure showed the surface was covered with a thin layer of PLA film. The fibre diameter at the top of the particle was always larger than that at the bottom of the fibre. After 120 h, 65.8% (25° C. group), 79.7% (37° C. group) and 89.6% (60° C. group) of the chlorhexidine dissolved and the bead on fibre structure collapsed (FIG. 17, panel (b), 37° C. group).

There may be some residual chlorhexidine bound to the PLA. According to the release profile of chlorhexidine fibres at different temperatures, the release kinetics of chlorhexidine is affected by temperature (FIG. 17, panel (c)). It was found that increasing temperature induced a higher percentage of chlorhexidine released during 120 hours. This temperature dependent release feature may be useful in the activation of chlorhexidine in differing environments encountered globally.

A burst release could also be observed at the start of the release cycle as the chlorhexidine chloride compounds were only covered by a thin layer of PLA. Therefore the water could dissolve and diffuse easily through the thin outmost PLA layer. These types of structures delivering a burst and then a sustained release could be useful for incorporation in medical devices and specifically denture bases to treat denture stomatitis. Other applications could be bandages, surgical gloves, antibacterial fabrics, polymers and packaging. There may also be many periodontal applications for these products.

Example 10

Figure 18:
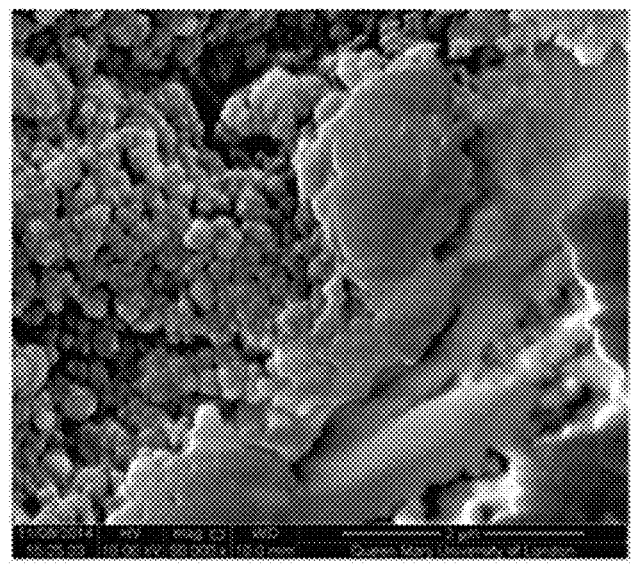
FIG. 18 shows SEM photomicrograph of the Surface of the HEMA-UDMA polymer disc containing bioglass after 28 days water storage showing the precipitation of a surface layer.

Chlorhexidine compounds described in Example 1-4 may be introduced into HEMA-UDMA, PEM or other polymer systems (Example 5) together with silanised/unsilanised pyrolytic silica fillers (from 1-90%) and/or bioactive/antibacterial glasses (Table 4). Glass particle size for the fillers is in the range of 1-5 microns ($D_{50}$). Bio-glasses in Table 4 were ground to a particle size of 3-10 microns and introduced into a HEMA-UDMA polymer system (Example 5) in the ratio of 3:2 and light cured using a blue light (3M ESPE Elipar, intensity of 900 mW/cm2 and wavelength of 430-480 nm) for 20 seconds for each side of the discs (discs=10×1 mm, n=6 per group). Storage of the discs in deionised water over 28 days and Inductive Coupled Plasma Atomic Emission Spectroscopy (ICP-AES) indicated the release of zinc, fluorine, strontium. These ions have reported antibacterial/regenerative effects, particularly on the anaerobic bacteria associated with many dental diseases including peri-implantitis, peri-mucositis and periodontal disease. Discs were also placed in an acidic environment (5 ml of 20 mmol dm-3 (1.8 g/l) lactic acid solution) for 3 weeks. There was a higher release of buffering ions through a diffusion mechanism, with bio-glass particles dissolving at a controlled rate and undergoing gradual dissolution. It was also possible to precipitate a fine surface layer on the composite following 28 days which may be silica rich (FIG. 18).

Composite discs were subjected to an X-ray radiopacity test. The X-ray (Dürr Dental, Germany) was operated at 60 kV with a 0.04 seconds exposure time for each disc. The digital radiographs were analysed using the Image J software (National Institutes of Health, Maryland, U.S.) in order to calculate the grey-scale value of the discs along with the grey-scale value for every 1 mm increment step of the step wedge. The step wedge grey-scale values were used to get a calibration curve and its corresponding line equation was used to convert the grey-scale value of the discs to mm of aluminium (mm of Al). The radiopacity results for glasses were in the range 2.44-3.681 (mm of Al) which passes the ISO 4049 standard requirement. This is due to the 3.5-4.5 mol % strontium content. Table 4 shows the bioactive glass compositions in mol %.

TABLE 4

| $SiO_2$ | CaO | $CaF_2$ | $SrF_2$ | SrO | MgO | ZnO |
|---|---|---|---|---|---|---|
| 47.32 | 7.01 | 5.52 | 5.52 | 3.4 | 31.23 | 0 |
| 47.32 | 7.01 | 5.52 | 5.52 | 3.4 | 30.23 | 1 |
| 47.32 | 5.91 | 5.52 | 5.52 | 4.5 | 29.23 | 2 |
| 47.32 | 5.2 | 5.52 | 5.52 | 5.21 | 28.23 | 3 |

Example 11

Chlorhexidine Spheres:
Functionalisation/Nucleation and Triggered Release

Chlorhexidine diacetate (99%), Poly(allylamine hydrochloride) (PAH, 56 kDa), Poly(sodium 4-styrenesulfonate) (PSS, 70 kDa), Rhodamine B Isothiocyanate dye (TRITC, 99%), Fluorescein isothiocyanate isomer I (FITC, >90%), Calcium Chloride (99.9%), Gold(III) chloride ($HAuCl_4$, >99%), Sodium borohydride (96%), Silver nitrate ($AgNO_3$, >99%) were all purchased from Sigma-Aldrich. Hexadecyltrimethylammonium bromide (CTAB, 96%) and Ascorbic acid (>99%) were purchased from Fluke. All the chemicals were used directly without further purification.

Synthesis of Gold Nanorods

Gold nanorods were synthesized according to a reported seed mediated growth protocol. Briefly, the seed solution was prepared by mixing 1 mL of 0.1 M CATB and 0.025 mL of 10 mM of $HAuCl_4$. While stirring, 0.1 mL of ice-cold 10 mM $NaBH_4$ was added. The mixture was kept at 25° C. Then 50 mL of 0.1 M CTAB, 1 mL of 4 mM $AgNO_3$, and 2.5 mL of 10 mM $HAuCl_4$ were mixed to produce the growth solution. Then 0.5 mL of 0.1 M ascorbic acid was added to the growth solution. Finally, 0.5 mL of the seed solution was finally added to the growth solution at 27° C. and the reaction was kept constant at this temperature for 6 hours. Based on the seed mediated growth method (Khanadeev et al., 2015, Colloid Journal, 77, 5, 652-660), the homogeneous gold nanorods have an average length of 85 nm and width of 20 nm. UV-vis spectroscopy of the gold nanorods displayed their absorbance peak at 840 nm.

Gold Nanorod Functionalization of the Chlorhexidine Spheres

To functionalize the chlorhexidine spheres with gold, the gold nanorod suspension was pre-mixed with 0.8 mL of 0.33 M $CaCl_2$, and then the mixture was introduced to 0.8 mL of 15 mg/mL chlorhexidine diacetate solution. Specifically, a series of gold suspensions, 5, 10, 50, 100, 200, and 400 μl (0.45 mg/mL), were premixed with $CaCl_2$ solution to determine the influence of nano particles on chlorhexidine growth. All the procedures were then the same as previous described in Example 2a and the gold nanorod functionalized chlorhexidine spheres were also freeze dried. The number of particles produced from all the mixtures was counted using a hemocytometer. Both Field Emission and back scattered SEM (FEI Inspect F, Eindhoven, The Netherlands) were used to characterize the synthesized particles, and the size of the gold-chlorhexidine composites were measured using image analysis software (Nano Measure, version 1.2). The gold nanorod functionalized chlorhexidine spheres were also characterized using Thermo-gravimetric analysis (TGA, Q50, USA) at 10° C./min under a nitrogen atmosphere and over a temperature range of 100-1000° C.

As demonstrated in FIG. 9 gold nanorod functionalized chlorhexidine spheres were synthesized by introducing the gold nanorods into the $CaCl_2$ solution. Without gold nanorods, the chlorhexidine spheres had a porous surface morphology, which were comprised of small dendrites. EDX mapping showed a homogenous and copious distribution of $Ca^{2+}$ and $Cl^-$ in the chlorhexidine spheres. In contrast, for the gold nanorods functionalized spheres (with 400 μl nanorods), at high magnification small gold nanorod clusters were present on the chlorhexidine dendrites.

Figure 20:
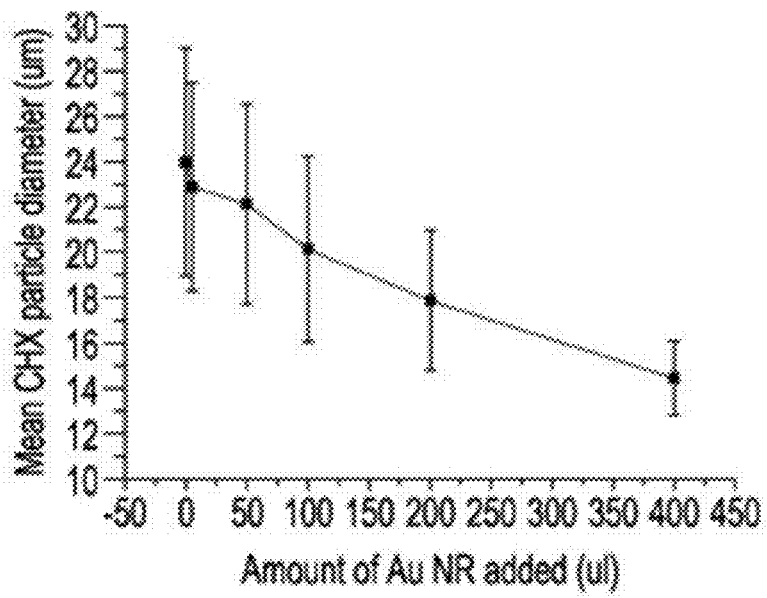
FIG. 20 shows the effect of gold nanorods on chlorhexidine crystallization. Panel (a) Mean chlorhexidine particle diameter and panel (b) chlorhexidine particle numbers as a function of gold nanorod addition (Au NR).
Figure 20:
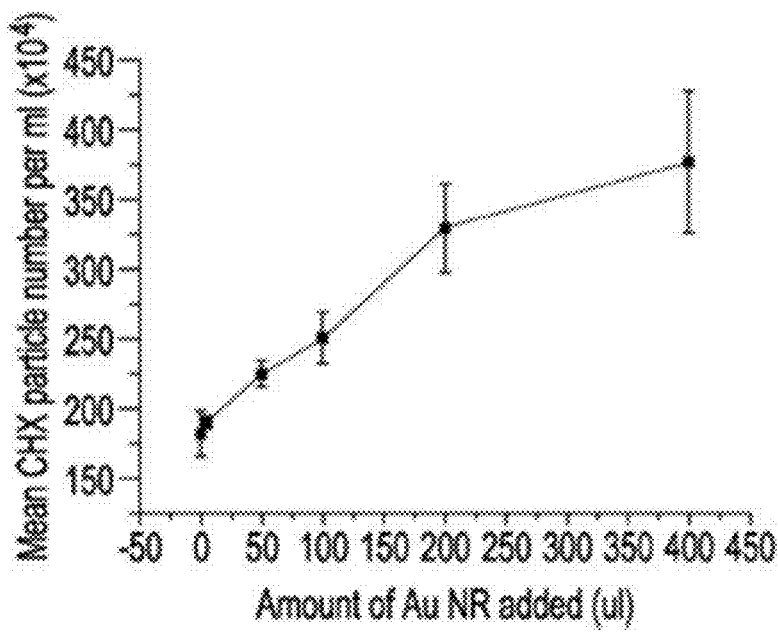

To understand the role of gold nanorods in chlorhexidine crystal growth, different amounts of gold nanorods were dispersed into $CaCl_2$) solutions. FIG. 20, panel (a) illustrates the influence of gold nanorods on the size of chlorhexidine spheres. Without the addition of gold nanorods the chlorhexidine spheres had a mean (SD) diameter of 24.0 (5.0) μm. Adding 5 μl of gold nanorods produced a slight size reduction of 22.9 (4.6) μm. The mean chlorhexidine sphere diameter and standard deviation gradually decreased on increasing addition of gold nanorods, with a 400 μl gold nanorod addition giving a mean (SD) diameter of 14.5 (1.6) μm. There was a correlation between the amount of gold nanorods added and the mean chlorhexidine particle diameter ($r^2$=0.98). SEM images indicated there was no distinct difference in the morphology of chlorhexidine spheres at different gold nanorods addition. The chlorhexidine precipitation efficiency (>98%) was also similar for all the samples. In terms of the particles size distribution, with less gold nanorods added, the size distribution was broader. When increasing the amount of gold nanorods however, the chlorhexidine spheres were more homogeneous. As for the chlorhexidine particle numbers, it was also correlated with the amount of gold nanorods added to solution ($r^2$=0.98, x from 0 to 200, FIG. 20, panel (b)). The remaining weight of functionalized chlorhexidine spheres also increased as a function of increased amount of gold nanorods which was confirmed by TGA analysis. This work illustrates the nucleation effect of introducing gold nanorods/other metals to control the size, number and distribution of chlorhexidine spheres. It is demonstrated that the surface area, size and number of crystallites can be controlled in the current invention. This gives the ability to effect the dissolution rates of the crystallites and their drug release. Structure property relations of the crystallites may therefore be tailored to different clinical applications and the treatment of infections.

Fabrication of Core-Shell Chlorhexidine Spheres

Growth of chlorhexidine spheres was also tuned and separated into two stages. The first stage involved the slow growth of small chlorhexidine crystals at low temperature and second the fast growth of chlorhexidine shells on top of the initial primary crystals. To visualize the two stages, chlorhexidine diacetate solutions were mixed with FITC and RhB accordingly. To produce small chlorhexidine primary crystals, both the chlorhexidine diacetate (15 mg/ml) and $CaCl_2$ solutions (0.33 M) were kept in an ice bath for one hour. The mixing of these solutions as described in Example 2a resulted in immediate precipitation of small chlorhexidine crystals. These pre-produced chlorhexidine crystals at 5, 50, 100, 200 and 400 µl ($1.63\times10^7$ crystallites/mL) were separately added to 0.33 M room temperature $CaCl_2$, and 15 mg/ml chlorhexidine diacetate solutions. After 1 minute, the mixtures were washed with $CaCl_2$ and characterized using confocal microscopy. The size effect induced by the chlorhexidine primary crystals was determined by analyzing the size distribution of produced chlorhexidine spheres using image analysis software (Nano Measure, version 1.2).

Figure 21:
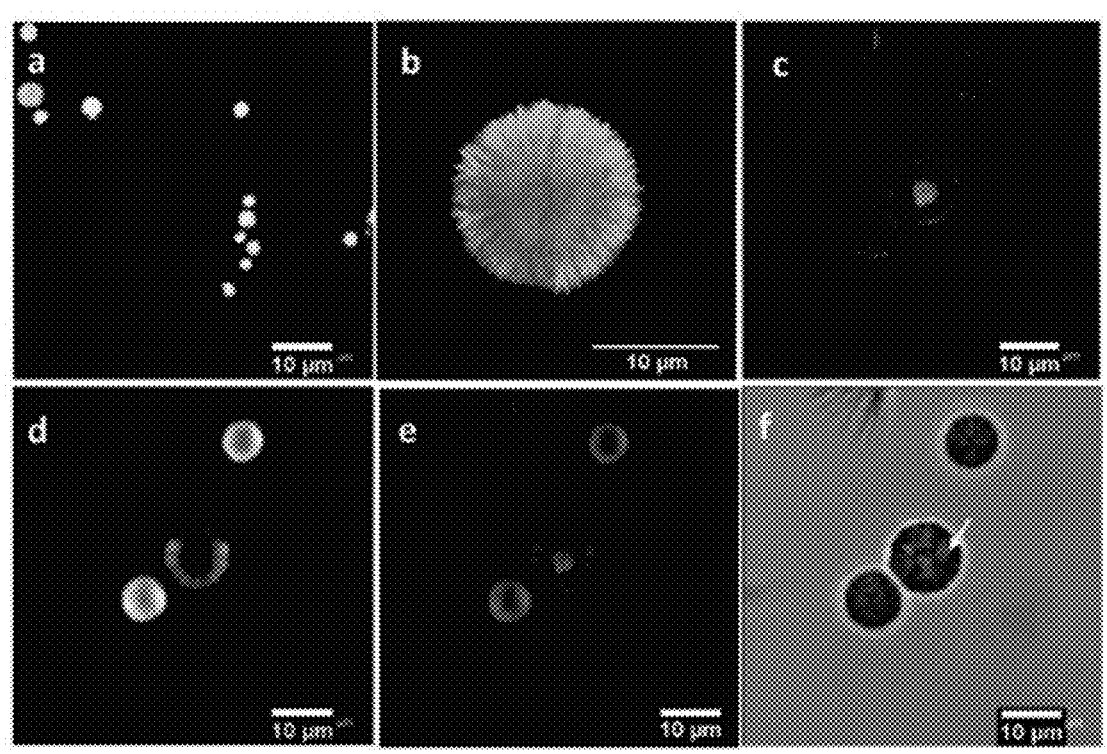
FIG. 21 shows confocal images of chlorhexidine spheres. Panel (a) chlorhexidine primary particles produced in an ice bath (labelled with FITC); panel (b) large chlorhexidine spheres produced at room temperature (labelled with RhB); core-shell chlorhexidine particles produced based on the small chlorhexidine primary particles showing panel (c) shell, panel (d) core and panel (e) merged image; panel (f) at transmitted channel.
Figure 22:
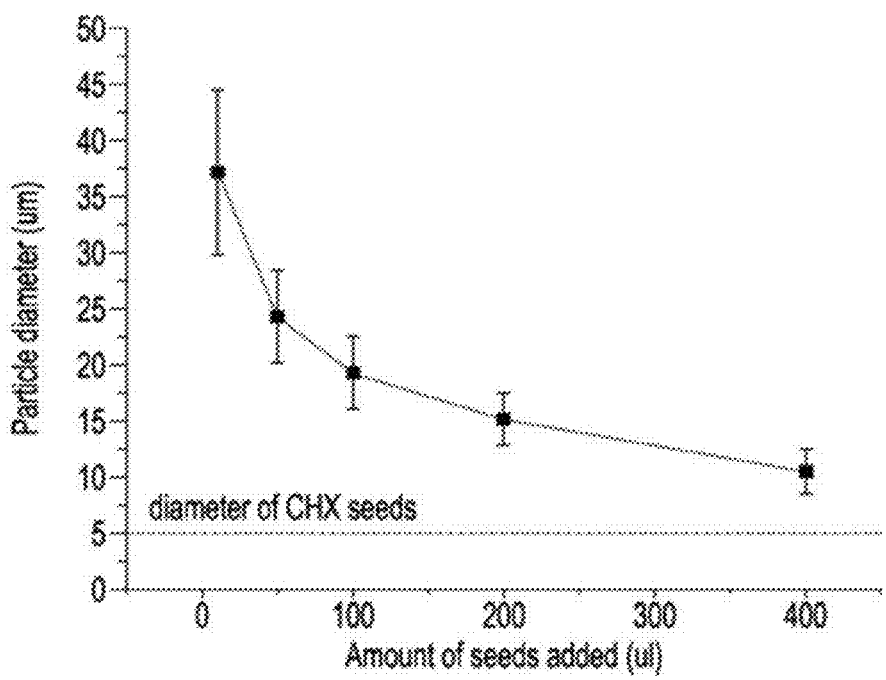
FIG. 22 shows the effect chlorhexidine seeds amount on the size of chlorhexidine spheres (dash line indicates the size of the chlorhexidine seeds).

In a parallel experiment, small chlorhexidine spheres were used as primary particles instead of gold nanorods to further reveal chlorhexidine crystallization. This was achieved by keeping the original chlorhexidine diacetate and $CaCl_2$) solutions in an ice bath and carrying out the synthesis to produce primary chlorhexidine particles with a mean (SD) diameter of 5.2 (1.7) µm (FIG. 21, panel (a)), while chlorhexidine spheres synthesized at room temperature had a mean (SD) diameter of 17.2 (1.9) µm (FIG. 21, panel (b)). By introducing the chlorhexidine primary particles into the $CaCl_2$) solution, growth of a second shell of chlorhexidine crystals were successfully achieved. FITC labelled chlorhexidine primary particles were presented as the core (FIG. 21, panel (a)) and the new shells grown from the interface around the primary particles were visible when labelled with RhB (FIG. 21, panels (d) and (e)). At the transmitted channel, a clear boundary between the chlorhexidine primary particles and outside shell was identified (FIG. 21f FIG. 21, panel (f)). Similarly, the mean particle diameter of the chlorhexidine spheres decreased as the amount of primary chlorhexidine particles increased (FIG. 22). The chlorhexidine particle size distribution also narrowed at increasing primary particle concentration. It has been demonstrated that the synthesis of primary chlorhexidine seeds can be used to control the size and distribution of the chlorhexidine spheres, with a core shell demonstrated. This structural change may be useful in controlled drug release properties of the crystallite and the ability to functionalise the chlorhexidine core via a surface crystallisation or epitaxial growth mechanisms.

LbL Assembly on Gold-Chlorhexidine Composites

Stabilization of chlorhexidine spheres was achieved by using LbL self-assembly. PAH (2 mg/mL) and PSS (2 mg/mL) were used as polyelectrolytes to be deposited on the gold-chlorhexidine composite surface. The LbL assembly procedure is described in Example 4. Successful encapsulation of the chlorhexidine spheres was achieved when polyelectrolytes were assembled in salt concentrations at which chlorhexidine particles were not dissolved (Example 4) and the chlorhexidine sphere cores remained intact after encapsulating 6 layers of polyelectrolytes. SEM images showed that the chlorhexidine capsules had completely coated the chlorhexidine structure and no dendritic structure could be identified.

Rupture of Gold Functionalized Chlorhexidine Capsules by NIR Light Irradiation

To irradiate the gold functionalized chlorhexidine capsules a customised laser setup was used (Carregal-Romero et al., *J Controlled Release*, 2012, 159, 1, 120-127). A 100 mW laser diode (840 nm) was coupled with a simple optical microscope (100× objective, Edmund Scientific, USA), and the focused laser spot was tuned by adjusting the operating laser voltage. In addition, the white light source and XYZ stages allowed samples to be easily located and focused. The laser beam passed through the objective in the Z direction and was focused at the sample to irradiate the specific site. A CCD camera was connected to a computer to capture this event. Thus, once aligned and focused, an image of sample and a laser spot could be observed on the screen. In the current work remote triggering of the gold functionalized chlorhexidine capsules was carried out using this laser setup.

Figure 23:
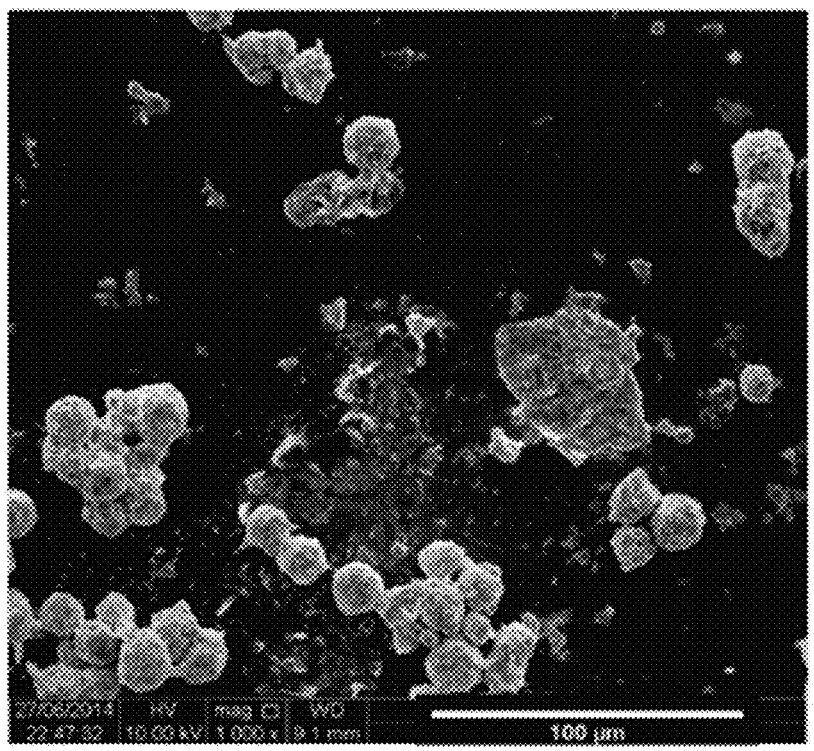
FIG. 23 shows SEM images of gold functionalized chlorhexidine capsules after laser irradiation. Untreated capsules were still intact but laser triggered ones were broken with polymer shells remaining.

The chlorhexidine capsule suspension was placed on a thin glass slide and the glass slide was marked to locate the particles. After application of the laser beam, the chlorhexidine capsules were broken which led to the dissolution of the chlorhexidine crystals and remaining polyelectrolytes shells. The sample was then dried in air and the laser triggered site was characterized using SEM and confocal microscopy. Using an 840 nm NIR light (up to 100 mW) with the laser setup, the chlorhexidine capsules could be ruptured while the others remained intact (FIG. 23). Once targeted by the laser beam, the capsule erupted and the exposed chlorhexidine spheres dissolved, as a result only polyelectrolyte shells remained as indicated in FIG. 23. Confocal analysis detected residual chlorhexidine within the residual shells.

NIR Light Controlled Release

Chlorhexidine release was performed in deionized $H_2O$ (n=3). 50 µl of gold-chlorhexidine capsules were diluted into 400 µl for each sample, and were exposed to a laser (100 mW) for 30 min (laser on) at each time point. Then the capsule suspensions were incubated at room temperature for 24 h (laser off). Supernatants (200 µl) from each sample at each time points (24, 24.5, 48, 48.5, 72, 72.5, 96, 96.5, 120, 120.5, 144, 168 h) were collected and replaced with equivalent fresh deionized $H_2O$. Chlorhexidine release was determined by UV-vis absorption (Lambda 35, Perkin Elmer, USA) at 254 nm according to the established calibration curve. Chlorhexidine release from capsules without laser treatment was used as the experimental control.

Figure 24:
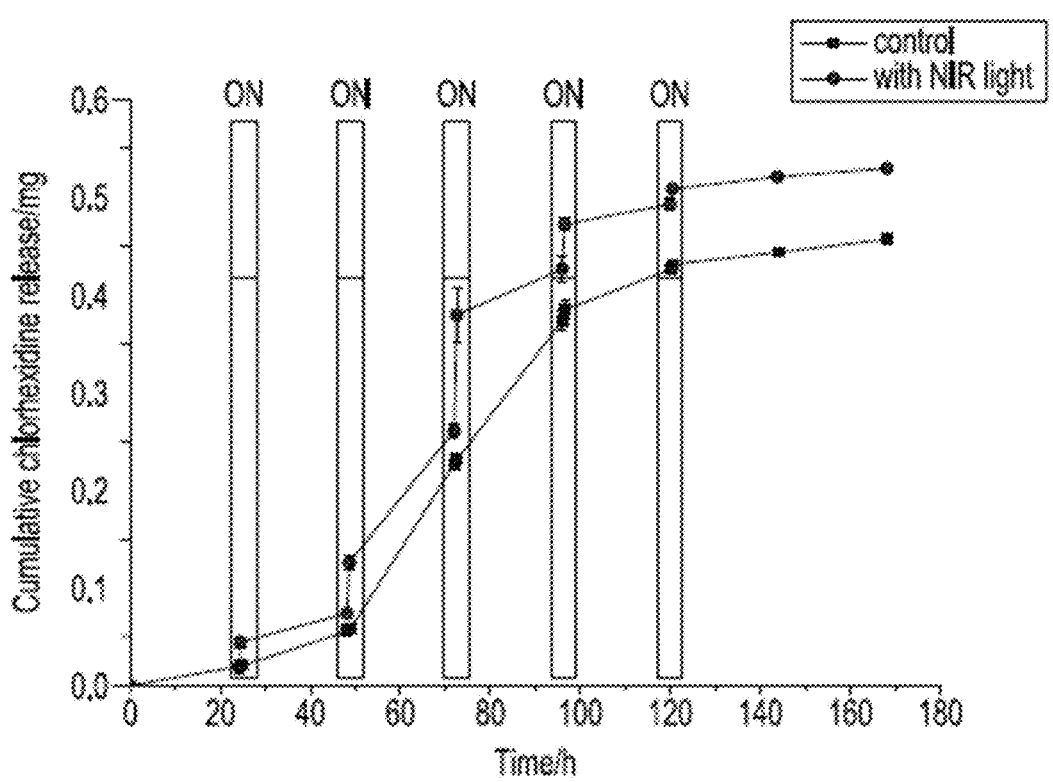
FIG. 24 shows cumulative release of chlorhexidine from capsules with (circle) and without (square) NIR light irradiation. Five cycles of NIR light on (30 min, 100 mW) are indicated by grey shades; values=Mean of 3 groups and vertical bars represent the SD.

According to the in vitro release kinetics (FIG. 24), chlorhexidine release occurred in a stepwise fashion after each cycle of laser treatment. A burst release was observed during each laser irradiation cycle. In contrast, the released chlorhexidine content during each cycle for the control was lower, although both groups exhibited a sustained release.

The proposed chlorhexidine capsules with high drug loading rate and NIR light responsive properties have advantages and promising applications. The gold nanorod functionalized chlorhexidine capsules are useful as they may be injected into sites such as periodontal pockets. A high local chlorhexidine content can be maintained and smart release to increase drug content can be achieved by simply exerting the NIR light. Photodynamic therapy using a diode laser is used in conjunction with a photosensitizer to decrease or eliminate bacteria [Haag et al., Int J Mot Sci. 2015, 16, 27327-27338.] and it may be possible to combine these therapies to increase its efficacy.

Example 12

Chlorhexidine Spheres: Cytotoxicity and Anti-Microbial Effectiveness

Preparation of Chlorhexidine Sphere Solutions

Chlorhexidine spheres were synthesized as in Examples 2. 0.5% chlorhexidine spheres stock solution was used to prepare fresh successive dilutions in sterile deionised water to obtain the final concentrations ranging from 0.0005 to 0.25%. For controls (untreated cultures), sterile deionised water was used. 25 µl of each treatment were added into respective wells to achieve final concentrations ranging from 0.00005-0.025%.

Cytotoxicity Assay

The cytotoxicity of different concentrations of chlorhexidine spheres (synthesised according to methods in Example 2-2c) solutions on cultured fibroblast-like L929 cells after different exposure times were evaluated. L929 cells, a mouse fibroblast-like cell line (ECACC 85011425) were cultured in Dulbecco's Modified Eagle's Medium (DMEM; Lonza, UK) supplemented with 10% fetal bovine serum (FBS) with 100 IU/mL penicillin, 100 µg/mL streptomycin and 2 mmol/L glutamine (all from Invitrogen, UK) in an humidified incubator with 10% $CO_2$ and 95% air at 37° C. Microscopically, the fibroblasts had a normal appearance and demonstrated a normal cell growth rate.

Cell metabolic activity was evaluated by measuring the mitochondrial activity using a method commonly known as a methyl-tetrazolium (MTT) assay. MTT assay was carried out according to the protocols outlined in ISO 1 0993-5: 2009 (Biological evaluation of medical devices—Part 5: Tests for in vitro cytotoxicity).

Trypsinisation was performed by routine methods and cell suspension was counted using a haemocytometer and seeded in 96-well microtiter plates at a concentration of 10,000 cells per well. The cells were then left overnight in the incubator to adhere to the wells. Following overnight incubation, medium was removed and cells were washed twice with PBS. The cells were then treated with different concentrations of chlorhexidine spheres (0.00005-0.025%) for 24 and 48 hours. Following treatment, culture medium containing chlorhexidine spheres was removed and 50 µL of 5 mg/mL tetrazolium salt MTT (Sigma-Aldrich, Gillingham, UK) was added to each well and incubated in 37 C for 4 h. Formazan crystals generated by mitochondrial enzyme activity were dissolved by 100 µl of isopropanol and the intensity of purple coloured reaction product quantified by measuring the absorbance spectra at 570 nm. A cell viability level below 70% of control (no treatment) was regarded as the toxic concentration according to the ISO protocol.

Figure 25:
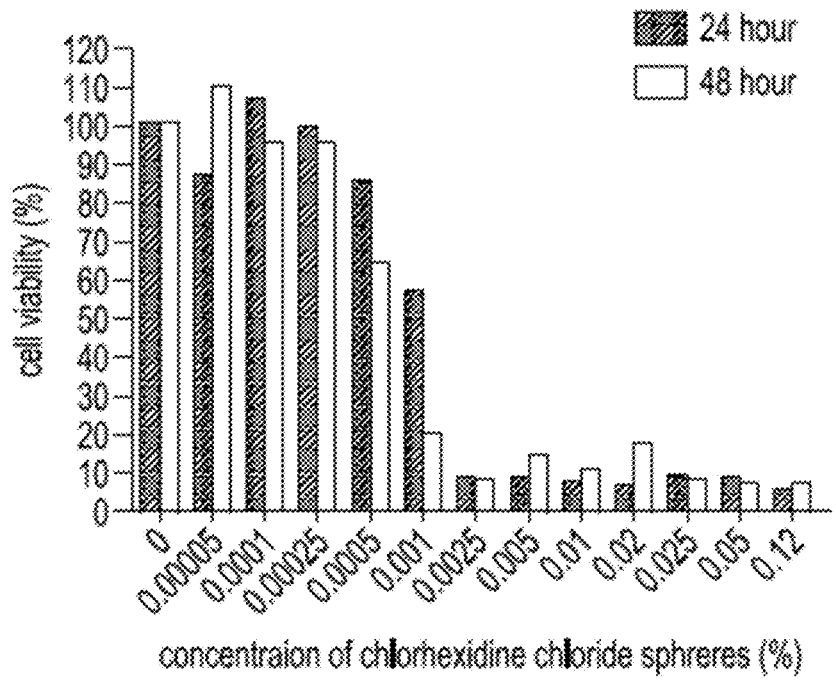
FIG. 25 shows effects of chlorhexidine spheres on the relative viability of fibroblast like L92 cells. The percentages of cellular viability in the presence of chlorhexidine relative to that in the control (0%) are shown. The results were obtained from six replicates of a single experiment.

Chlorhexidine spheres demonstrated cytotoxicity at concentrations above 0.0005%. Treatment with chlorhexidine spheres reduced the viability of the L929 cells in a dose-dependent manner (FIG. 25). Relative cellular viability was reduced to approximately 50% when 0.001% of chlorhexidine spheres were used for 24 hours which was further reduced to 20% when treated for 48 hours. Lower concentrations of chlorhexidine spheres ranging from 0.00005% to 0.00025% showed approximately 90% of cellular viability at both 24 and 48 hours' time point. Although 0.0005% chlorhexidine spheres demonstrated>80% of cellular viability at 24 hours, the viability was reduced just below 70% at 48 hours. The higher concentrations of chlorhexidine that are used for burns and wounds (0.05%) and oral rinses (0.12%) demonstrated higher cytotoxicity at both 24 and 48 hours where cellular viability was below 10% (FIG. 25)

The data from this study suggests that, the lower concentrations of chlorhexidine spheres ranging from 0.00005% to 0.0005% are relatively safe for fibroblast like cells L929 whilst the concentrations used in current practice could be highly cytotoxic to the cells if exposed for prolonged duration (24-48 hours).

Cell Proliferation Assay

To determine any increase in cell numbers over time following chlorhexidine spheres treatment, a cell proliferation assay was performed by analysing the total DNA content using a fluorimetric plate reader based assay (Hoechst dye, R. Rago analytical biochemistry, 1990, 191: 31-34). Briefly, the 96 well plates were collected at 24 and 48 hour time points, washed twice with PBS and stored at −20° C. The cells were thawed to room temperature and 100 µl distilled water was added to each well, incubated for another hour and refrozen to suspend DNA. After 24 hrs, cells were thawed again and 100 µl of the fluorochrome Hoechst 33258 (Sigma-Aldrich, UK) at the concentration 20 µg/ml in THE buffer (2M NaCl) was added to each well. The intensity of the fluorescence was then read at λ 350 nm excitation and λ 460 nm emissions.

Figure 26:
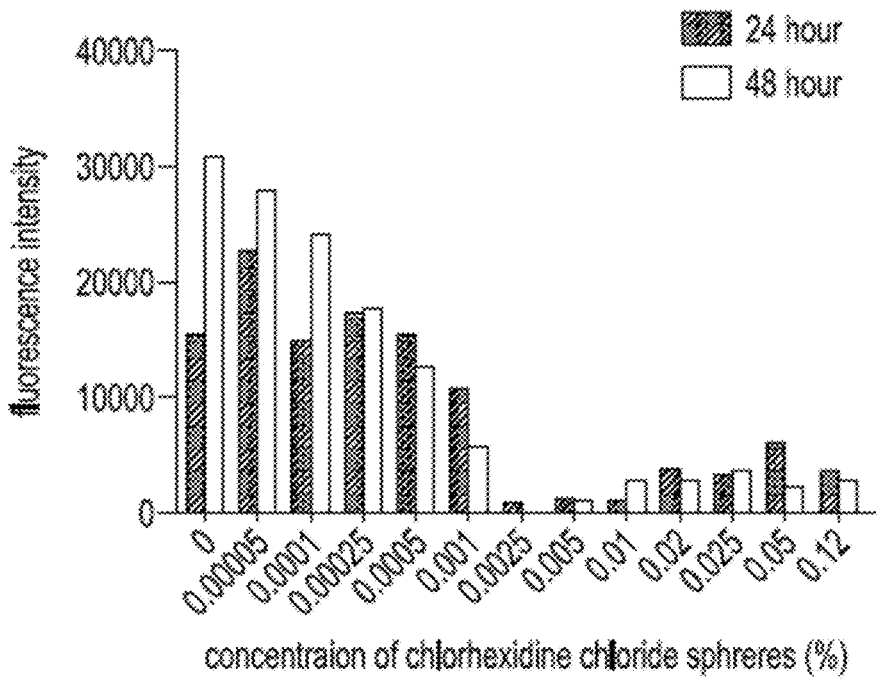
FIG. 26 shows effects of chlorhexidine spheres on the proliferation of fibroblast like L929 cells. The fluorescence intensity of L929 cells in the presence of chlorhexidine relative to that in the control (0%) is shown. The results were obtained from six replicates of a single experiment.

Chlorhexidine spheres demonstrated cytotoxicity at concentrations above 0.0005%. The effect of chlorhexidine spheres on fibroblast-like L929 cell proliferation was measured by a DNA fluorometric assay. As demonstrated in FIG. 26, chlorhexidine spheres concentrations ranging from 0.00005% to 0.00025% induces proliferation after both 24 and 48 hour treatment. However, no proliferation could be seen at 0.0005% following 24 hour treatment. Proliferation was significantly inhibited by concentrations at or above 0.001%.

Lower concentrations of chlorhexidine spheres ranging from 0.00005% to 0.0005% were found safe for fibroblast like cells L929 whilst the concentrations in current practice were highly cytotoxic to the cells over a prolonged period of exposure (24-48 h). Cell proliferation was profoundly reduced by relatively higher concentrations (>0.0005%) of chlorhexidine spheres whereas lower concentrations ranging from 0.00005% to 0.00025% induced cell proliferation.

Anti-Microbial Assay: Bacterial Strains and Growth Conditions

The effectiveness of the chlorhexidine spheres against a panel of periodontal pathogens was evaluated by measurements of the growth (optical density) of bacterial cultures. *Porphyromonas gingivalis* (strain-W50), *Fusobacterium nucleatum* sub species *polymorphum* (strain-NCTC10562) and *Aggregatibacter actinomycetemcomitans* (strain-Y4) were grown on blood agar plates and in brain heart infusion (BHI) broth in an anaerobic environment with an atmosphere of 5% $H_2$, 10% $CO_2$, and 85% $N_2$ at 37° C. for 2 days. BHI broth was pre-reduced with 5 µg/ml herein and 5 µg/ml menadione bisulphite added. Bacterial numbers in the BHI cultures were determined and standardised by serial dilution and enumeration of colony forming units (CFUs) on agar plates. After overnight incubation, the bacterial suspensions were diluted 1:20 with fresh BHI medium to achieve an optical density of 0.1 for *P. gingivalis* and *A. actinomycetemcomitans* and 0.2 for *F. nucleatum* sub sp. *polymorphum* at 595 nm ($OD_{595}$) to give approximately $6.5×10^7$ colony-forming units (CFU) per ml.

Preparation of Chlorhexidine Spheres Solutions

A 0.08% chlorhexidine spheres stock solution was used to prepare fresh successive dilutions in sterile deionised water to obtain the final concentrations ranging from 0.0000625 to 0.04%. For controls (untreated cultures), sterile deionised water was used. 25 µl of each treatment were added into respective wells to achieve a final concentration ranging from 0.0000625-0.008% in BHI.

MIC and MBC of Chlorhexidine Spheres

To determine the Minimum Inhibitory Concentration (MIC) and Minimum Bactericidal Concentration (MBC) of chlorhexidine spheres against *P. gingivalis*, *F. nucleatum* and *A. actinomycetemcomitans*, 96-well flat-bottomed microtiter plates were used with a final assay volume of 250 µl/well (225 µl/well of bacterial solution and 25 µl/well of each treatment). Negative control (bacterial inoculum only but no chlorhexidine spheres) and blank (medium only) wells were also included. The microtiter plates were incubated for 0, 24 and 48 hours in anaerobic conditions as above and the optical density (OD) was determined at 595 nm to quantify bacterial growth. The MIC was defined as the lowest concentration of chlorhexidine spheres that inhibited the growth of microorganism at each time point. The MBC was the lowest concentration of chlorhexidine spheres giving no observable bacterial growth. MBC was determined following transfer of the microtiter well contents to micro centrifuge tubes, centrifuging to pellet the bacterial cells, washing to remove any remaining chlorhexidine spheres and incubation on blood agar plates. After incubation anaerobically growth of bacteria that had survived the treatment was recorded.

Antimicrobial Assay Results

Figure 27:
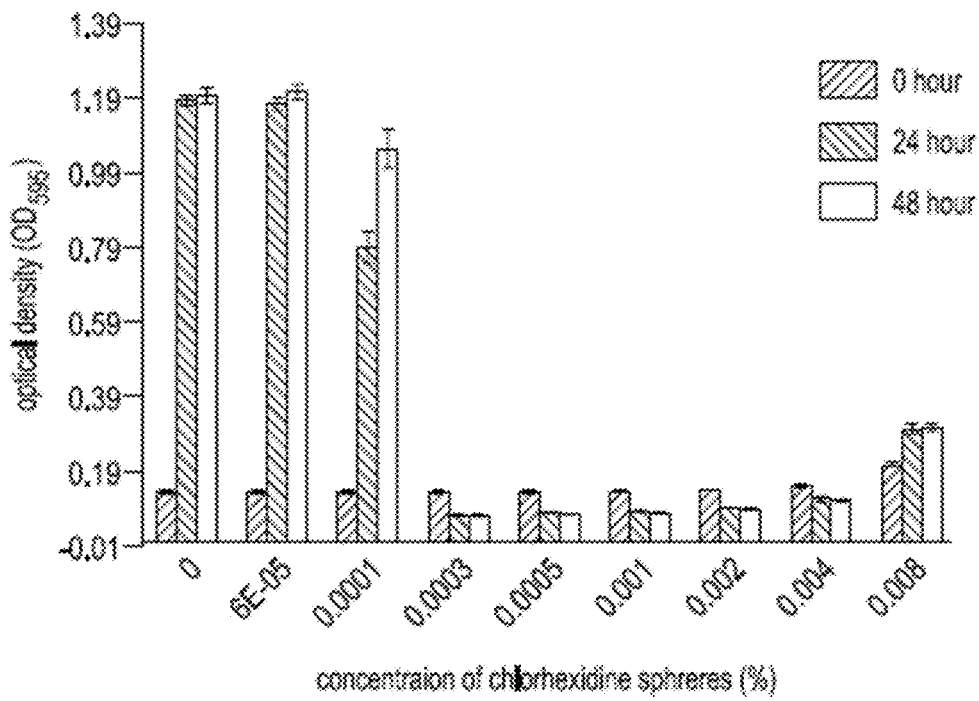
FIG. 27 shows the effects of chlorhexidine spheres on *P. gingivalis*. The optical density of chlorhexidine treated cultures relative to that in the control (0%) are shown. The results were obtained from six replicates in each of three independent experiments.

Results from three independent antimicrobial tests showed that the concentration of chlorhexidine spheres required to inhibit (MIC) planktonic *P. gingivalis* was 0.00025% at both the 24 and 48 hour time points (FIG. 27). When treated bacteria were recovered and re-incubated on agar plates to determine the MBC, no visible bacterial growth was observed at 0.0005%, 0.001% and 0.002% treated 24 hour cultures. This indicates that after 24 hours treatment. 0.0005% chlorhexidine spheres has a bactericidal effect on *P. gingivalis*. Bacterial growth was visible on 0.00025% chlorhexidine spheres treated cultures demonstrated that treatment with this concentration for 24 hours inhibits the growth of *P. gingivalis* but does not kill the organism. However, 48 hours treatment with 0.00025% chlorhexidine spheres cultures did not demonstrate any visible bacterial growth. The results demonstrate that at 24 hours, the MIC of chlorhexidine spheres is 0.00025% whilst the MBC is 0.0005%. But, for longer exposure (48 hours) the concentration of chlorhexidine spheres required to kill (MBC) planktonic *P. gingivalis* is 0.00025% (Table 5).

TABLE 5

MIC and MBC of chlorhexidine spheres against *P. gingivalis*

| Concentration of Chlorhexidine spheres (%) | 24 hours | 48 hours |
|---|---|---|
| 0.00025 | MIC | MBC |
| 0.0005 | MBC | MBC |
| 0.001 | MBC | MBC |
| 0.002 | MBC | MBC |

Figure 28:
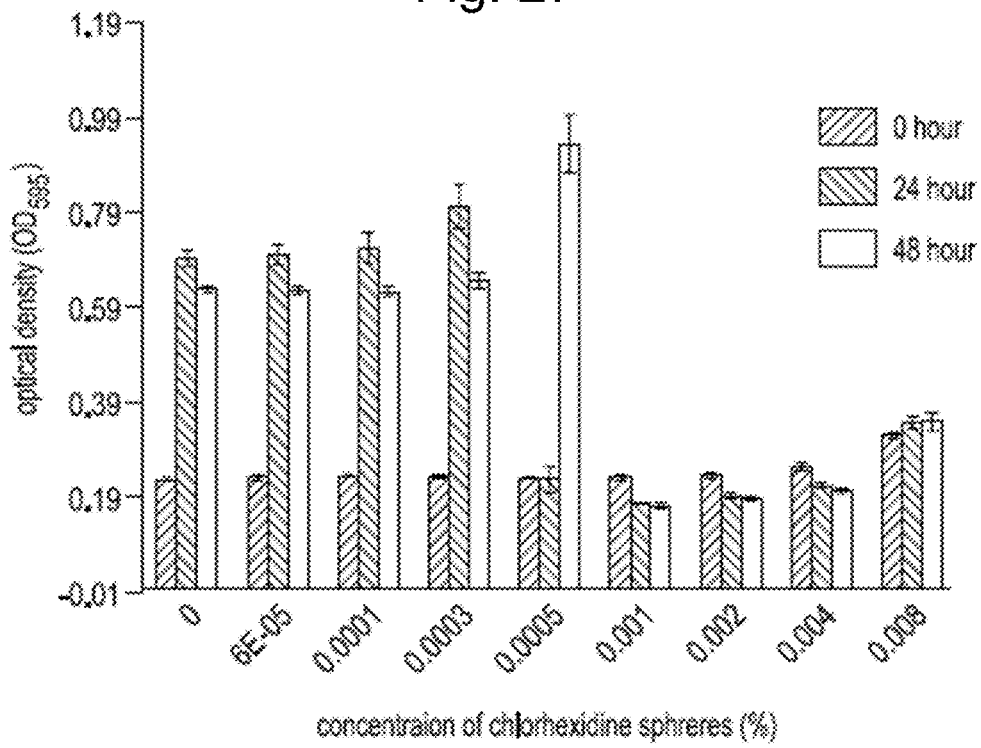
FIG. 28 the effects of chlorhexidine spheres on *F. nucleatum* sub sp. *polymorphum*. The optical density of chlorhexidine treated cultures relative to that in the control (without chlorhexidine spheres) are shown. The results were obtained from six replicates in each of three independent experiments.

Results from two independent antimicrobial tests showed that the concentration of chlorhexidine spheres required to inhibit (MIC) planktonic *F. nucleatum* sub sp. *polymorphum* was 0.0005% at 24 hour and 0.001% 48 hour time points (FIG. 28). When treated *F. nucleatum* sub sp. *polymorphum* were recovered and re-incubated on agar plates to determine the MBC, no visible bacterial growth was observed at 0.001%, 0.002% and 0.004% treated 24 hour cultures. This indicates that after 24 hours treatment, 0.001% chlorhexidine spheres has a bactericidal effect on *F. nucleatum* sub sp. *polymorphum*. Although, bacterial growth was inhibited by 0.0005% of chlorhexidine spheres at 24 hours, recovered and re-incubated bacteria from these cultures demonstrated visible growth which suggests that treatment with this concentration for 24 hours do not have bactericidal effect on *F. nucleatum* sub sp. *polymorphum*. Therefore, the results indicate that the MIC and MBC of chlorhexidine spheres are 0.001% at both 24 and 48 hours (Table 6).

TABLE 6

MIC and MBC of chlorhexidine spheres against *F. nucleatum* sub sp. *polymorphum*

| Concentration of Chlorhexidine spheres (%) | 24 hours | 48 hours |
|---|---|---|
| 0.0005 | No Inhibition | No Inhibition |
| 0.001 | MBC | MBC |
| 0.002 | MBC | MBC |
| 0.004 | MBC | MBC |

Figure 29:
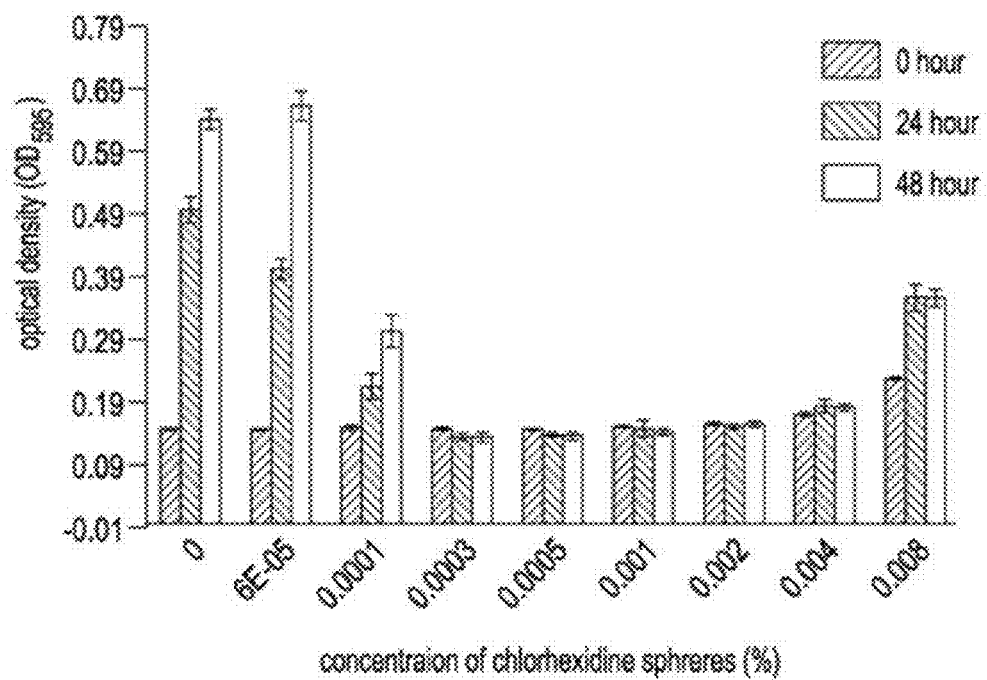
FIG. 29 shows the effects of chlorhexidine spheres on *A. actinomycetemcomitans*. The optical density of chlorhexidine treated cultures relative to that in the control (0%) are shown. The results were obtained from six replicates in each of three independent experiments.

Results from two independent antimicrobial tests showed that the concentration of chlorhexidine spheres required to inhibit (MIC) planktonic *A. actinomycetemcomitans* was 0.00025% at both 24 and 48 hour time point (FIG. 29). When treated bacteria were recovered and re-incubated on agar plates to determine the MBC, no visible bacterial growth was observed at 0.00025%, 0.0005% and 0.001% treated 24 hour cultures. This indicates that after 24 hours treatment, 0.00025% chlorhexidine spheres has a bactericidal effect on *P. gingivalis*. No bacterial growth was visible on either of these treated (0.00025%, 0.0005% and 0.001%) cultures at 48 hours. This suggests that the MBC of chlorhexidine spheres for *A. actinomycetemcomitans* is 0.00025% (Table 7).

TABLE 7

MIC and MBC of chlorhexidine spheres against *A. actinomycetemcomitans*

| Concentration of Chlorhexidine spheres (%) | 24 hours | 48 hours |
|---|---|---|
| 0.00025 | MBC | MBC |
| 0.0005 | MBC | MBC |
| 0.001 | MBC | MBC |

Lower concentrations of chlorhexidine spheres (≥0.00025%) were found to have an antimicrobial effect on *P. gingivalis* and *A. actinomycetemcomitans* whilst for *F. nucleatum*, the threshold for inhibition (MIC) was 0.001% chlorhexidine spheres. chlorhexidine spheres described in this patent provide an effective antimicrobial effect against a range of bacteria associated with periodontal disease and peri-implantitis and at a safer concentration than in current products such as oral rinses (0.12%) burns/wounds (0.05%) and intraoral chips (0.01250%). This may reduce any adverse effects such as pain, swelling, sensitivity associated with these chlorhexidine products and less risk for patients.

Example 13

Chlorhexidine Spheres: Encapsulation, Cytotoxicity and Anti-Bacterial Effectiveness Chlorhexidine diacetate (C6143, Lot 19H0417), Poly (allylamine hydrochloride) (PAH, 56 kDa, 283223, Lot MKBJ4274V), Poly(sodium 4-styrenesulfonate) (PSS, 70 kDa, 243051. Lot BCBF6120V), Rhodamine B (RhB, 283924, Lot 063K3407), Fluorescein isothiocyanate isomer I (FITC, Lot 020M5305), Calcium Chloride (C8106, Lot SLBF7416 V), Phosphate buffered Saline (PBS, Lot RNBD7772), DMEM (41966, Lot 1513243) Thiazolyl Blue Tetrazolium Bromide (MTT, M5655, Lot 052K5328) were all purchased from Sigma-Aldrich. Poly (lactic acid) (PLA, 2002D), Nature works. Agar (BP1423, Lot 127054), Tryptone (BPE9726, Lot 21012), Yeast Extract (BCE800, Lot4381720) and Sodium chloride (S3160, Lot 1333838), Fisher Bio reagents.

Chlorhexidine particles were made by precipitation of 15 mg/ml chlorhexidine diacetate with 0.33M $CaCl_2$ at a ratio of 1:1 by volume at room temperature according to Example 2. LbL self-assembly of PAH and PSS was carried out to encapsulate the chlorhexidine particles as in Example 4 (FIG. 11, panels (a) and (b)).

Electrospinning of PLA Fibres

PLA fibres were fabricated by electrospinning at room temperature, with a working distance of 15 cm, pumping rate of 1 ml/h, and a voltage of 18 kV. PLA was dissolved in a mixed solvent of chloroform and acetone (3:1 by volume) at 7% as in Example 9. Both encapsulated and uncoated chlorhexidine particles were added at 0.5, 1 and 5% (wt/wt) to the PLA and mixed using a Rotomix (ESPE RotoMix, USA). PLA fibres (mats) were collected on foil and characterized using SEM and the Mean (SD) diameter was analysed using Nano Measure software (version 1.2). Confocal microscopy and FTIR (Bruker, Billerica, Mass.) were also used to confirm the presence of chlorhexidine. Tensile tests of the electrospun fibre mats (n=3 per test group) with unencapsulated chlorhexidine particle additions were performed using the stress-strain mode on a dynamic mechanical analysis instrument (DMA Q800, TA instrument). Prior to the test, the electrospun fibre mats were cut into rectangular specimens (35×7 mm). They were mounted onto a clamp and stretched at a rate of 0.1 N/min, with 0.05 N pre-load applied.

Figure 30:
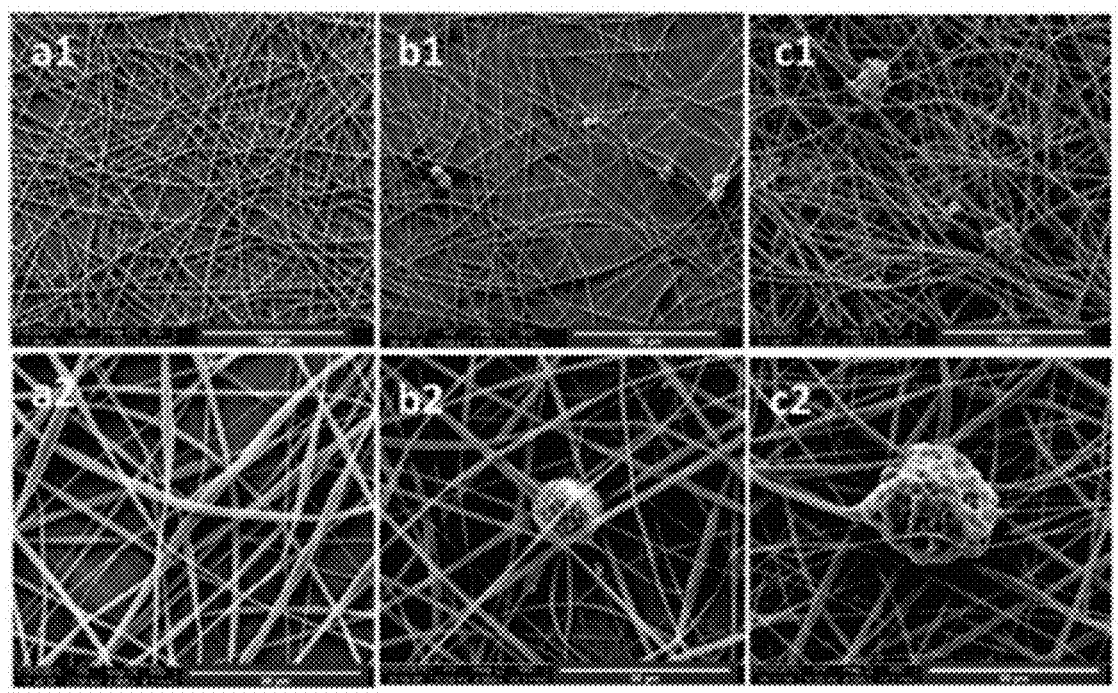
FIG. 30 shows SEM images of electrospun fibres containing 5% chlorhexidine: panel (a) PLA fibres as a control; panel (b) fibres with uncoated chlorhexidine particles; panel (c) fibres with encapsulated chlorhexidine particles at a magnification of (1) 1000× and (2) 4000×.
Figure 31:
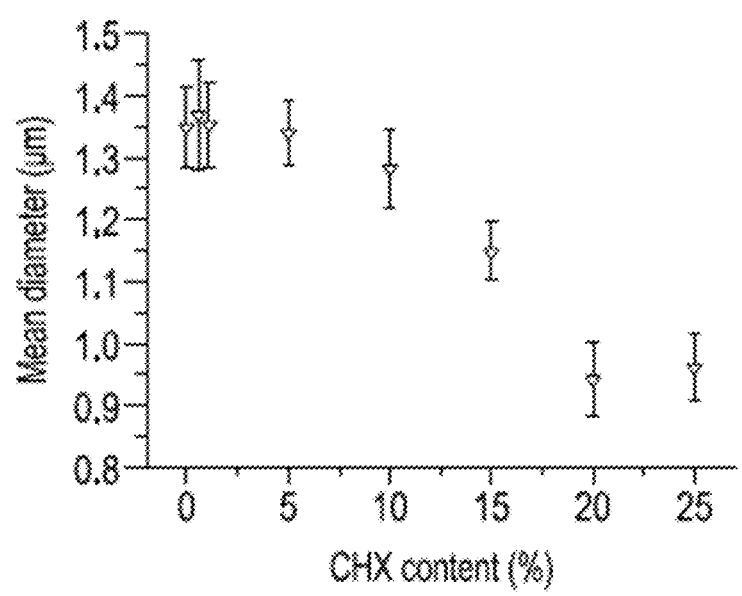
FIG. 31 shows mean (SD) diameter of the PLA fibres as a function of chlorhexidine particle content.

Chlorhexidine was incorporated into the PLA fibres by electrospinning as in Example 9. The SEM images of the fabricated fibres (FIG. 30, panel (a)) indicate a regular fibrous structure. When the chlorhexidine particles were incorporated (5%), a bead-in-string structure was demonstrated, in which the spheres were connected by two ends, with one fibre end much thicker than the other. For the fibres with chlorhexidine particles, a very thin layer of PLA covered the particle surface and the particle structure could still be seen (FIG. 30, panel (b)). In contrast, when the chlorhexidine particles were encapsulated and electrospun into fibres, a rougher appearance was observed (FIG. 30, panel (c)). The mean diameter (SD) of the PLA fibres (control) was 1.35±0.06 µm. When the content of the chlorhexidine was increased (from 0.5% to 25%) the diameter of fibres decreased, as demonstrated in FIG. 31. There was no significant difference when the chlorhexidine content was below 10%. Further increasing the ratio to 25% (wt/wt), the chlorhexidine particles significantly (p<0.01) reduced the fibre diameter to 0.96±0.06 µm. After incorporating the CHX particles, the mechanical properties of the PLA electrospun fibre mats were also decreased (Table 8). While, the contact angle test showed that wettability of fibres was not affected by particle incorporation (123.6±3.7° for control and 121.6±7.2° for 5.0% wt/wt CHX fibres).

TABLE 8

Tensile properties of PLA fibres containing different amounts of chlorhexidine particles.

| Sample Name | Young's modulus MPa (SD)* | Elongation at break % (SD) | Tensile Strength MPa (SD) |
|---|---|---|---|
| PLA fibre | 31.32 (5.85) | 30.4 (2.38) | 1.55 (0.14) |
| PLA fibre-0.5% CHXP | 25.63 (3.06) | 11.89 (1.73) | 0.70 (0.05) |
| PLA fibre-1.0% CHXP | 10.47 (1.14) | 13.84 (0.41) | 0.37 (0.02) |
| PLA fibre-5.0% CHXP | 11.75 (1.81) | 13.40 (0.63) | 0.36 (0.02) |

*Young's modulus was calculated by the slope of the stress-strain curve at 1% strain; CHXP = Chlorhexidine particle.

Release Kinetics of Chlorhexidine From the Fibres

The release of chlorhexidine from the fibres was carried out in $H_2O$ and buffer (PBS). Fibres containing 5% (wt/wt) chlorhexidine particles (coated and uncoated) were collected from the foil and weighed (Salter ANDER-180A weighing scale, UK). They were divided into cuvettes, and each sample was 25 mg (n=3). 2 ml of deionized $H_2O$ or PBS was added to each cuvette and the fibres were kept immersed at room temperature. At each time point (from 1 h to 650 h), fibres were transferred into fresh medium and the solutions were measured using UV-vis absorption (Lambda 35, Perkin Elmer, USA). The chlorhexidine released into the solutions was determined at 254 nm according to an established calibration curve. After 650 hours all the fibres were collected and characterized again with SEM and confocal microscopy.

Figure 32:
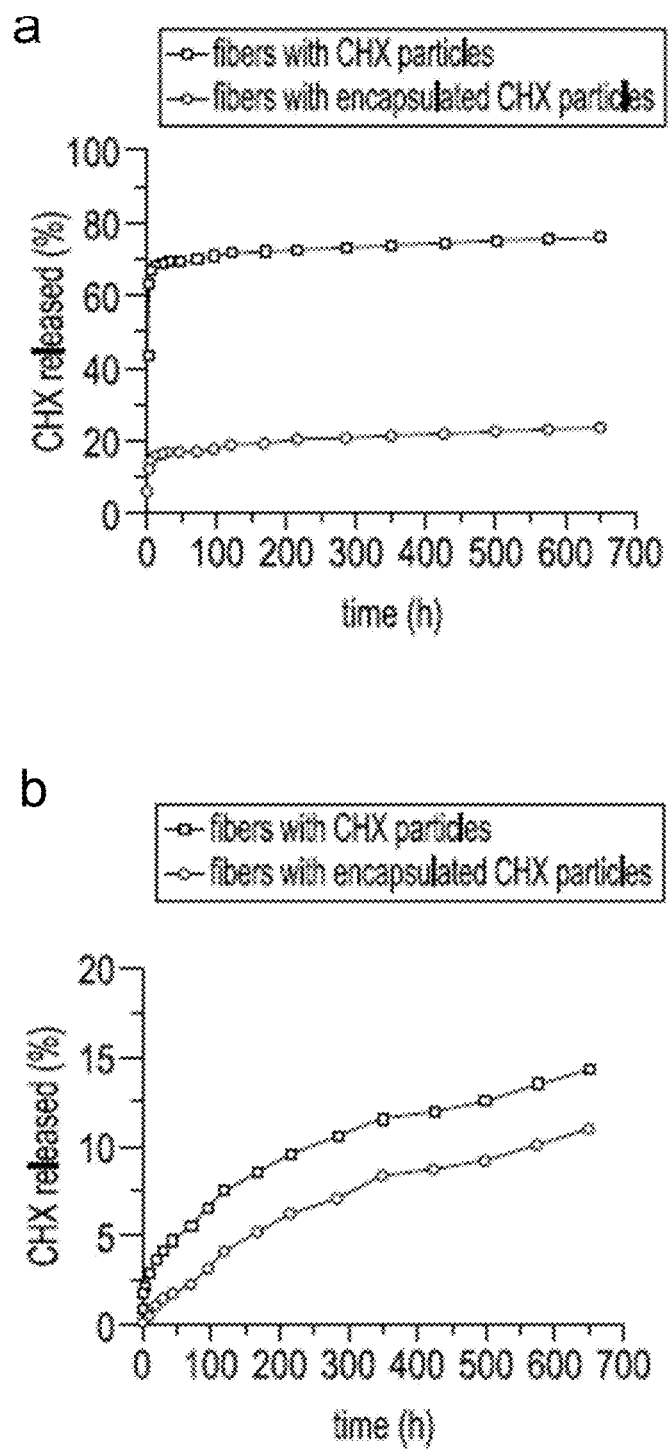
FIG. 32 shows release kinetics of chlorhexidine particle containing fibres in: panel (a) H2O and panel (b) PBS. The PLA fibres with uncoated and encapsulated chlorhexidine particles had a chlorhexidine content of 5% (wt/wt).

The release profile of chlorhexidine from the PLA fibres containing chlorhexidine particles was monitored over 650 hours (FIG. 32, panel (a)). In $H_2O$ the fibres with uncoated chlorhexidine particles showed a burst release during the first day, with over 60% of the chlorhexidine released, after which a sustained release was observed. In contrast, the fibres with encapsulated particles displayed a lower (20-25%) sustained release of chlorhexidine. In PBS, both of the fibres had much lower release rates compared to that in $H_2O$, and chlorhexidine encapsulation again produced a lower but sustained release rate (FIG. 32, panel (b)). The porous surface of the collapsed sphere revealed the original morphology, indicating that the PLA layer had been penetrated (FIG. 17, panel (b)). Fibres containing encapsulated chlorhexidine particles retained more of their surface coating and chlorhexidine content in the collapsed spheres. It was therefore possible to demonstrate that tailored release of chlorhexidine is possible via use of the novel chlorhexidine particles both encapsulated and incorporated in fibres. Tailored drug delivery and controlled release is useful in the treatment of recurrent infections and those formulations could be incorporated into membranes, textiles, gloves and medical devices.

Cytotoxicity of the Chlorhexidine Containing Fibres

The cytotoxicity of chlorhexidine containing fibres to fibroblasts (3T3 cells) was determined using the MIT assay. Both fibres with 0.5, 1 and 5% (wt/wt) chlorhexidine particles (coated and uncoated), and PLA fibres without chlorhexidine, were rinsed with 70% ethanol and sterilized by exposing to UV for 2 h. The fibres were then immersed in culture medium at 1 mg/ml and were kept in the incubator for 24 h or 48 h. The fibres were next removed and the medium used for cell culture. The 3T3 cells (William Harvey Research Institute) were seeded in 96-well plates at 1×104 per well, and cultured with fresh medium for 24 h. The medium was then removed and replaced with the chlorhexidine fibre release medium, and cells were cultured for 5 days. The medium was next removed and 20 µl of MTT solution was added to each well and cells were cultured for 4 h. Then 150 µl of MTT solvent (4 mM HCl, 0.1% Nondet P-40 in isopropanol) was added to each well. The plate was read in a Multiskan Ascent Plate Reader (Thermo Fisher Scientific, UK) with the filter at 570 nm.

Figure 33:
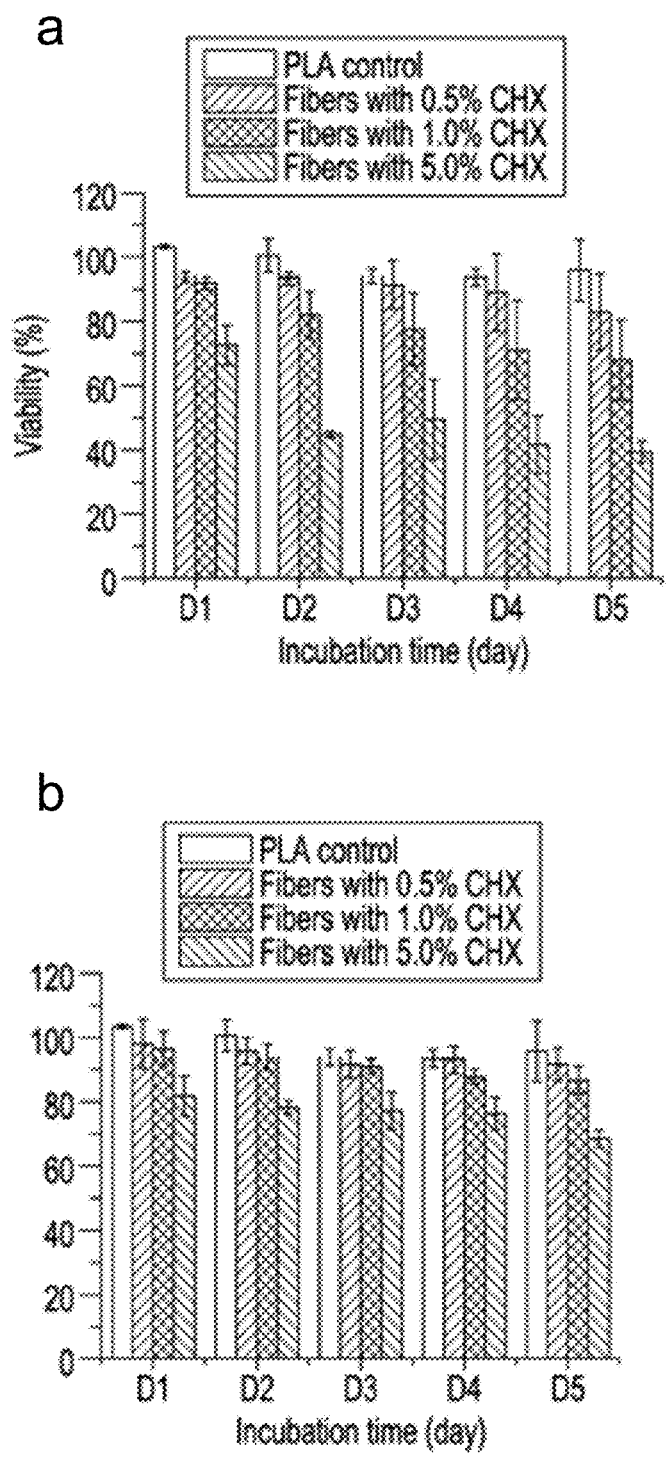
FIG. 33 shows cytotoxicity of fibres containing chlorhexidine with fibroblast cells (3T3). PLA fibres containing uncoated chlorhexidine particles panel (a) and encapsulated chlorhexidine particles panel (b). Values are the mean of 5 wells and vertical lines are SD, *p<0.05 and **p<0.01 indicate statistical differences compared to the control PLA fibre treated cells.

The cytotoxicity of the fibres (containing novel particles) to the fibroblasts is shown in FIG. 33, panels (a) and (b). The fibres containing uncoated and encapsulated chlorhexidine particles with 0.5% and 1% (wt/wt) chlorhexidine were not toxic to cells over a period of 5 days, as there was no statistical difference (p>0.05) in cell viability between the PLA control and the two test groups. When the chlorhexidine content in the fibres was increased to 5% (wt/wt), the fibres containing the uncoated chlorhexidine particles reduced the cell viability significantly over 1 day (p<0.05) and more than 2 days (p<0.01). The fibres with encapsulated particles (5% chlorhexidine loading) showed better compatibility with cells, with slight cell viability reduction at day 2 and day 5 (p<0.05).

Fibroblast Adhesion to the Fibres

Both fibres with 0.5, 1 and 5% (wt/wt) chlorhexidine particles (coated and uncoated) were cut into 0.8 cm×1 cm mesh, and sterilized using the method described above. PLA fibres without chlorhexidine particles were used as a control. Prior to cell seeding, the fibre meshes were fixed at the bottom of a removable cell culture chamber (Lab-Tek® II, Chamber Slide TM). An engineered 3T3 cell (expressing EGFP) (Gould et al., *Arthritis Res. Thor.*, 2007) suspension was added to each well at 2×104 cells per well, and then cultured for 24 h. The fibre meshes were collected and rinsed with PBS to remove any of the dead or detached cells. Confocal microscopy images were acquired with a confocal microscope using a 63×/Oil DIC (WD=0.19 mm) objective. All the fibre meshes were spread on glass slides and scanned in x-y-z mode. The interval between sections was set as 0.3 µm. All the images along the z position were stacked and three-dimensionally displayed using Imaris software (Bitplane, version 7.7).

Cell adhesion to the fibres is another indicator of potential cytotoxicity, as demonstrated in FIG. 34. The number of fluorescent cells on the PLA fibres directly reflected the influence of chlorhexidine content, with fewer cells on the 5% (wt/wt) chlorhexidine containing fibres than those on the control PLA fibres. The cells appeared less spread out on the fibres and more spherical shaped cells were observed, which may suggest toxicity at 5% (wt/wt) chlorhexidine content. Fibres with less chlorhexidine (0.5 and 1% wt/wt) in the fibres, encouraged cell adherence to the fibres, with typically elongated cell filopodia extensions. A similar observation was made for fibres with encapsulated chlorhexidine particles. The combination of the novel chlorhexidine spheres together with processing into fibres/encapsulation allows the safe use of a higher drug content (1%) which will be useful in situations such as recurrent infections where a long and sustained safe drug release is required and for medical devices.

Antibacterial Assay

The antibacterial properties of chlorhexidine particle loaded electrospun PLA fibres were tested by growth inhibition of *Escherichia coli* (*E. coli*, DH5a), using both an agar diffusion assay and broth transfer assay. The LB broth base solution was prepared (0.5 g NaCl, 10 g tryptone, 5 g yeast extract per litre). To make the LB agar plates, agar was added to the LB broth base solution at 15 g/L. Bacterial suspension in LB broth base solution was cultured at 37° C. with 200 rpm agitation, and the density of the suspensions was adjusted to that of a McFarland 0.5 turbidity, which corresponded to 1.5×108 cells/ml using a spectrophotometer (Cecil CE2021, USA) at 625 nm. 0.4 ml of the bacterial suspension was spread on the surface of LB agar plates. The sensitivity of the *E. coli* to inhibition with chlorhexidine was firstly demonstrated using filters (diameter 7 mm), treated with uncoated or encapsulated chlorhexidine particles with chlorhexidine concentrations from 5 mg/ml to 50 µg/ml and placed on agar plates pre-spread with *E. coli*. The fibres were cut into discs (diameter 7 mm, thickness 0.1 mm) and rinsed with 70% ethanol and $H_2O$, and then placed on LB agar plates which were incubated at 37° C. for 24 h and then the diameter (SD) (n=3) of zones of inhibition were measured in mm.

Antibacterial activity of the fibres against *E. coli* is presented in FIG. 35. The diameter of the clear zone is an indication of the inhibitory effect of the chlorhexidine containing fibres, with higher chlorhexidine ratio in the fibres leading to large inhibition zones. No inhibition against *E. coli* was observed for the control PLA discs. For fibres with chlorhexidine particles, large inhibition zones were observed for all the fibre discs with chlorhexidine ratio at 0.5, 1 and 5% (wt/wt), and higher chlorhexidine loading rates resulting in larger inhibition zones. In contrast, the inhibitory zones were only observed at 1 and 5% (wt/wt) for the fibres with encapsulated chlorhexidine particles, which resulted in much smaller inhibitory diameters (p<0.01). The chlorhexidine particles may be combined with encapsulation and or processed into fibres and this allows higher drug content (0.5 and 5% wt/wt) and controls drug efficacy. This allows many options to tailor the drug at higher content to the specific disease or application. Specific uses include; surgical membranes, medical devices, textiles, antibacterial food packaging, bandages and treatments for cattle and pigs who are susceptible to infections such as *E. coli*.

The sustained antibacterial effect of the chlorhexidine containing fibres was also examined in a transfer experiment. Bacterial suspensions in LB broth base, with McFarland 0.5 turbidity were diluted 200 times. Each of the fibre discs (fibres with uncoated or encapsulated chlorhexidine particles containing 0.5, 1 and 5% (wt/wt) chlorhexidine, n=3) were immersed into the bacterial suspensions (1 ml) and cultured at 37° C./200 rpm agitation. After each hour, the fibre discs were transferred into fresh bacterial suspensions. After 9 hours, all the fibre discs were discarded and all the bacterial suspensions were incubated for another 24 hours. The optical absorptions were measured at 625 nm (Cecil CE2021, USA). The Student's t test (Microsoft Excel, 2016 software) was used to analyze statistically significant differences between groups. The sustained inhibition effect against *E. coli* was demonstrated by the transfer experiment. The chlorhexidine burst release (uncoated particles) within one hour inhibited proliferation of *E. coli* in LB broth suspensions over the next 24 hours. For the control (untreated bacterial suspensions), the bacteria proliferated and a turbidity around 0.8 was found after 24 hours. However, 5% (wt/wt) chlorhexidine in both the fibre containing uncoated and encapsulated chlorhexidine particles completely inhibited bacterial growth even after nine transfers. When the chlorhexidine content in the fibres was reduced to 1% (wt/wt), no inhibition was observed for the fibres with encapsulated particles and the inhibition effect against *E. coli* depleted quickly after 4 transfers for fibres containing the uncoated chlorhexidine particles. Similar observations were displayed for the fibres with 0.5% (wt/wt) encapsulated chlorhexidine particles.

The invention claimed is:

1. A crystalline salt of chlorhexidine chloride having a spherical morphology under Scanning Electron Microscopy (SEM) comprising a chloride anion and a cation selected from the group consisting of calcium, sodium, potassium, magnesium, zinc, strontium, and iron.

2. A crystalline salt of chlorhexidine chloride according to claim 1, in which the cation comprises calcium and the crystalline salt has an X-ray diffraction pattern comprising peaks, in terms of 2-theta, at about 8.5°, about 13.4°, about 15.9°, about 20.9°, about 23.7°, and about 26.6°.

3. Monodisperse crystals of a crystalline salt of chlorhexidine chloride according to claim 1.

4. A process for the preparation of monodisperse crystals of a crystalline chlorhexidine chloride salt of claim 3, comprising
(i) mixing an aqueous solution of chlorhexidine acetate with an aqueous solution of a metal chloride of the formula ($MCl_x$), where x is equal to 1 or 2, at a concentration of 0.1M to 1.0 M;
(ii) allowing the chlorhexidine chloride salt to precipitate;
(iii) centrifuging the precipitate formed in (ii) to obtain a solid mass of precipitated salt crystals; and
(iv) washing the precipitated solid mass of (iii).

5. A process as claimed in claim 4, further comprising introducing emulsions, colloids, micro or nano-scale inorganic or metallic oxides into the aqueous solution of chlorhexidine acetate in step (i).

6. A crystalline chlorhexidine chloride salt prepared by a process according to claim 4.

7. A cement composition comprising a crystalline salt of chlorhexidine chloride according to claim 1.

8. A pharmaceutical composition comprising a crystalline chlorhexidine chloride salt according to claim 1.

9. A composition comprising a crystalline chlorhexidine chloride salt according to claim 1 encapsulated or suspended in a polyelectrolyte, or in a polymerizable monomer.

10. A composition as claimed in claim 9, in which the polymerizable monomer comprises a methacrylate.

11. A composition as claimed in claim 9, in which the polymerizable monomer comprises a dimethacrylate monomer.

12. A composition as claimed in claim 10, in which the polymerizable monomer comprises a hydrophilic monomer.

13. A composition as claimed in claim 9, in which the polyelectrolyte is polylactic acid (PLA).

14. A composition comprising a bioactive glass composed of at least two or more compounds selected from the group consisting of $SiO_2$, CaO, $CaF_2$, $SrF_2$, SrO, MgO, ZnO, $K_2O$, $B_2O_3$, ZnO, $PO_3$, $P_2O_5$, NaF, $CaCl_2$) and NaCl and a crystalline form of a chlorhexidine chloride salt according to claim 1.

15. A composition as claimed in claim 14, further comprising silica.

16. A composition comprising a metal or metal oxide particle of mean average particle diameter size 10 to 50 nm and a crystalline chlorhexidine chloride salt according to claim 1.

17. A composition of claim 16 encapsulated or suspended in a polyelectrolyte, or a polymerizable monomer.

18. A composition as claimed in claim 16, further comprising a polyelectrolyte.

19. A composition as claimed in claim 9, further comprising a photoinitiator.

20. A crystalline chlorhexidine chloride salt according to claim 1 in the form of a mouthwash, toothpaste, gel or polymer.

21. A natural or synthetic fibre further comprising a crystalline chlorhexidine chloride salt according to claim 1.

22. A natural or synthetic fibre as claimed in claim 21 selected from the group consisting of cellulose, cotton, polyurethane and nylon.

23. The composition as claimed in claim 10, in which the polymerizable monomer comprises hydroxyethyl methacrylate (HEMA), urethane dimethacrylate (UDMA), polymethylmethacrylate (PMMA), bisphenol A glycidylmethacrylate (BISGMA), and/or triethylene glycol dimethacrylate (TEGDMA).

* * * * *